United States Patent [19]
McGonigle et al.

[11] Patent Number: 6,096,504
[45] Date of Patent: Aug. 1, 2000

[54] MAIZE GLUTATHIONE-S-TRANSFERASE ENZYMES

[75] Inventors: Brian McGonigle, Wilmington, Del.; Daniel P. O'Keefe, Ridley Park, Pa.

[73] Assignee: E. I. du Pont Nemours and Company, Wilmington, Del.

[21] Appl. No.: 09/248,335

[22] Filed: Feb. 10, 1999

Related U.S. Application Data

[63] Continuation-in-part of application No. 08/924,759, Sep. 5, 1997, Pat. No. 5,962,229.

[51] Int. Cl.$^7$ .............................. C12Q 1/68; C12N 1/20; C12N 5/00; C07H 21/04

[52] U.S. Cl. .............................. 435/6; 435/193; 435/455; 435/410; 435/252.33; 435/320.1; 536/23.1; 536/23.2; 536/23.6

[58] Field of Search .............................. 435/193, 252.33, 435/410, 320.1, 6, 455; 536/23.2, 23.1, 23.6

[56] References Cited

U.S. PATENT DOCUMENTS

| | | | |
|---|---|---|---|
| 5,073,677 | 12/1991 | Helmer et al. | 800/205 |
| 5,589,614 | 12/1996 | Bridges et al. | 800/205 |

FOREIGN PATENT DOCUMENTS

| | | |
|---|---|---|
| 0 256 223 | 5/1987 | European Pat. Off. . |
| WO 93 01294 | 1/1993 | WIPO . |
| WO 96/23072 | 8/1996 | WIPO . |
| WO 97/11189 | 3/1997 | WIPO . |
| WO99/14337 | 9/1999 | WIPO . |

OTHER PUBLICATIONS

David C. Holt et al., Characterization of the Safener–Induced Glutathione S–Transferase Isoform II from Maize, *Planta*, 196, 295–302, 1995.

F. Droog, Plant Glutathione S–Transferases, a Tale of Theta and Tau, *J. Plant Growth Regul*, 16, 95–107, 1997.

Laura Rossini et al., Characterization of Glutathione S–Transferase Isoforms in Three Maise Inbred Lines Exhibiting Differential Sensitivity to Alachlor, *Plant Physiol*, 112, 1595–1600, 1996.

Kathleen A. Marrs, The Functions and Regulation of Glutathione S–Transferases in Plants, *Annu. Rev. Plant Physiol. Plant Mol. Biol.*, 47, 127–158, 1996.

Sharad S. Singhal et al., Purification and Characterization of Glutathione S–Transferase from Sugarcane Leaves, *Phytochemistry*, 30, No. 5, 1409–1414, 1991.

Robert Edwards et al., Glutathione Transferases in Wheat (Triticum) Species with Activity toward Fenoxaprop–Ethyl and Other Herbicides, *Pesticide Biochemistry and Physiology*, 54, 94–104, 1996.

Michael A. Wosnick et al., Total Chemical Synthesis and Expression in *Escherichia coli* of a Maize Glutathione–Transferase (GST) Gene, *Gene*, 76, 153–160, 1989.

Ian Jepson et al., Cloning and Characterization of Maize Herbicide Safener–induced cDNAs Encoding Subunits of Glutathione S–Transferase Isoforms I, II, and IV, *Plant Molecular Biology*, 26, 1855–1866, 1994.

Dianne A.M. van der Kop et al., Isolation and Characterization of an Auxin–Inducible Glutathione S–Transferase Gene of *Arabidopsis Thaliana*, *Plant Molecular Biology*, 30, 839–844, 1996.

Czarnecka et al. *Mol. Cell. Biol.*, 8(3), 1113–1122, 1988.

Dilip M. Shah et al., Structural Analysis of a Maize Gene Coding for Glutathione–S–Transferase Involved in Herbicide Detoxification, *Plant Molecular Biology*, 6, 203–211, 1986.

Robert E. Moore et al., Cloning and Expression of a cDNA Encoding a Maize Glutathione–S–Transferase in *E. Coli*, *Nucleic Acids Research*, 14, No. 18, 7227–7235, 1986.

Kriton K. Hatzios et al., Herbicide Safeners, *J. Environ. Sci. Health*, B31(3), 545–553, 1996.

Thomas Flury et al., A 2,4–D–Inducible Glutathione S–Transferase from Soybean (Glycine Max)., *Physiologia Plantarum*, 94, 312–318, 1995.

Robert Edwards, Characterization of Glutathione Transferases and Glutathione Peroxidases in Pea, *Physiologia Plantarum*, 98, 594–604, 1996.

McGonigle, Brian et al., Hemoglutathione selectivity by soybean, Pestic. Biochem. Physiol. (1998), 62(1), 15–25.

Koeppe et al., Role of glutathione conjugation in the detoxification of sulfonylurea herbicides in plants, Book of Abstracts, 216$^{th}$ American Chemical Society, (1998), (Abstract).

Grove et al., Characterization and Heterospecific Expression of CDNA Clones of Genes in the Maize GSH S–Transferase Multigene Family, *Nucleic Acids Research*, vol. 16, No. 2, 425–438, Jan. 1, 1988.

Dixon et al., Purification regulation and cloning of a glutathione transferase (GST) from maize resembling the auxin–inducible type–III GST's *Plant Molecular Biology*, vol. 36, 75–87, Jan., 1998.

(List continued on next page.)

Primary Examiner—Nashaat Nashed

[57] ABSTRACT

This invention relates to isolated nucleic acid fragments encoding all or a substantial portion of maize glutathione-S-transferase (GST) enzymes involved in the detoxification of xenobiotic compounds in plants and seeds. The invention also relates to the construction of chimeric genes encoding all or a substantial portion of maize GST enzymes, host cells transformed with those genes and methods of the recombinant production of maize GST enzymes. Methods of constructing transgenic plants having altered levels of GST enzymes and screens for identifying maize GST enzyme substrates and maize GST enzyme inhibitor, are also provided.

8 Claims, No Drawings

OTHER PUBLICATIONS

Wen et al., Expressed sequence tags from B73 maize seedlings, Jun. 8, 1998.

Nash et al., Bronze–2 gene from maize reconstruction of a wild–type allele and analysis of transcription and splicing, The Plant Cell, vol. 2, pp. 1039–1049 1990.

Marrs et al., A glutathione S–transferase involved in vacuolar transfer encoded by the maize gene Bronze–2, Nature, vol. 375, Jun. 1, 1995 pp. 397–400.

Dixon et al., Glutathione–mediated detoxification systems in plants, Current Opinion in Plant Biology, vol. 1, No. 3, Jun. 1998, pp. 258–266.

Timmerman, Molecular Characterization of Corn Glutathione S–Transferase isozymes involved in Herbicide Detoxification, Physiologia Plantarum, vol. 77, No. Symp.01, Jan. 1, 1989, pp. 465–471.

Neuffeind, et al., Plant glutathione S–Transferases and herbicide detoxification, Biological Chemistry, vol. 378, Mar. 1997 pp. 199–205.

MAIZE GLUTATHIONE-S-TRANSFERASE ENZYMES

This is a continuation-in-part of application Ser. No. 08/924,759 filed Sep. 5, 1997, now U.S. Pat. No. 5,962,229.

FIELD OF THE INVENTION

This intention is in the field of plant molecular biology. More specifically, this invention pertains to nucleic acid fragments encoding maize glutathione-S-transferase (GST) enzymes involved in the detoxification of xenobiotic compounds in plants and seeds.

BACKGROUND OF THE INVENTION

Glutathione-S-transferases (GST) are a family of enzymes which catalyze the conjugation of glutathione, homoglutathione (hGSH) and other glutathione-like analogs via a sulfhydryl group, to a large range of hydrophobic, electrophilic compounds. The conjugation can result in detoxification of these compounds. GST enzymes have been identified in a range of plants including maize (Wosnick et al., *Gene* (Amst) 76 (1) (1989) 153–160; Rossini et al., *Plant Physiology* (Rockville) 112 (4) (1996) 1595–1600; Holt et al., *Planta* (Heidelberg) 196 (2) (1995) 295–302), wheat (Edwards et al., *Pestic. Biochem Physiol.* (1996) 54(2), 96–104), sorghum (Hatzios et al., *J. Environ. Sci. Health*, Part B (1996), B31(3), 545–553), arabidopsis (Van Der Kop et al., *Plant Molecular Biology* 30 (4) (1996), sugarcane (Singhal et al., *Phytochemistry* (OXF) 30 (5) (1991) 1409–1414), soybean (Flury et al., *Physiologia Plantarum* 94 (1995) 594–604) and peas (Edwards R., *Physiologia Plantarum* 98 (3) (1996) 594–604). GST's can comprise a significant portion of total plant protein, for example attaining from 1 to 2% of the total soluble protein in etiolated maize seedlings (Timmermann, *Physiol Plant.* (1989) 77(3), 465–71).

Glutathione S-transferases (GSTs; EC 2.5.1.18) catalyze the nucleophilic attack of the thiol group of GSH to various electrophilic substrates. Their functions and regulation in plants has been recently reviewed (Marrs et al., *Annu Rev Plant Physiol Plant Mol Biol* 47:127–58 (1996); Droog, F. *J Plant Growth Regul* 16:95–107, (1997)). They are present at every stage of plant development from early embryogenesis to senescence and in every tissue class examined. The agents that have been shown to cause an increase in GST levels have the potential to cause oxidative destruction in plants, suggesting a role for GSTs in the protection from oxidative damage. In addition to their role in the protection from oxidative damage, GSTs have the ability to nonenzymatically bind certain small molecules, such as auxin (Zettl et al., *PNAS* 91:689–693, (1994)) and perhaps regulate their bioavailability. Furthermore the addition of GSH to a molecule serves as an "address" to send that molecule to the plant vacuole (Marrs et al., *Nature* 375:397–400, (1995)).

GSTs have also been implicated in the detoxification of certain herbicides. Maize GSTs have been well characterized in relation to herbicide metabolism. Three genes from maize have been cloned: GST 29 (Shah et al., *Plant Mol Biol* 6, 203–211(1986)), GST 27 (Jepson et al., *Plant Mol Biol* 26:1855–1866, (1994)), GST 26 (Moore et al., *Nucleic Acids Res* 14:7227–7235 (1986)). These gene products form four GST isoforms: GST I (a homodimer of GST 29), GST II (a heterodimer of GST 29 and GST 27), GST III (a homodimer of GST 26), and GST IV (a homodimer of GST 27). GST 27 is highly inducible by safener compounds (Jepson (1994) supra; Holt et al., *Planta* 196:295–302, (1995)) and over-expression of GST 27 in tobacco confers alachlor resistance to transgenic tobacco (Jepson, personal communication). Additionally, Bridges et al. (U.S. Pat. No. 5,589,614) disclose the sequence of a maize derived GST isoform II promoter useful for the expression of foreign genes in maize and wheat. In soybean, herbicide compounds conjugated to hGSH have been detected and correlated with herbicide selectivity (Frear et al., *Physiol* 20: 299–310 (1983); Brown et al., *Pest Biochem Physiol* 29:112–120, (1987)). This implies that hGSH conjugation is an important determinant in soybean herbicide selectivity although this hypothesis has not been characterized on a molecular level.

Some efforts have been made to alter plant phenotypes by the expression of either plant or mammalian foreign GST genes or their promoters in mature plant tissue. For example, Helmer et al. (U.S. Pat No. 5,073,677) teach the expression of a rat GST gene in tobacco under the control of a strong plant promoter. Similarly, Jepson et al. (WO 97/11189) disclose a chemically inducible maize GST promoter useful for the expression of foreign proteins in plants; Chilton et al. (EP 256223) discuss the construction of herbicide tolerant plants expressing a foreign plant GST gene; and Bieseler et al. (WO 96/23072) teach DNA encoding GSTIIIc, its recombinant production and transgenic plants containing the DNA having a herbicide-tolerant phenotype.

Manipulation of nucleic acid fragments encoding soybean GST to use in screening in assays, the creation of herbicide-tolerant transgenic plants, and altered production of GST enzymes depend on the heretofore unrealized isolation of nucleic acid fragments that encode all or a substantial portion of a soybean GST enzyme.

SUMMARY OF THE INVENTION

The present invention provides nucleic acid fragments isolated from maize encoding all or a substantial portion of a GST enzyme. The isolated nucleic acid fragment is selected from the group consisting of (a) an isolated nucleic acid fragment encoding all or a substantial portion of the amino acid sequence selected from the group consisting of SEQ ID NO:2, SEQ ID NO:4, SEQ ID NO:6, SEQ ID NO:8, SEQ ID NO:10, SEQ ID NO:12, SEQ ID NO: 14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:72 and SEQ ID NO:74; (b) an isolated nucleic acid fragment that is substantially similar to an isolated nucleic acid fragment encoding all or a substantial portion of the amino acid sequence sequence selected from the group consisting of SEQ ID NO:2, SEQ ID NO:4, SEQ ID NO:6, SEQ ID NO:8, SEQ ID NO:10, SEQ ID NO: 12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:72 and SEQ ID NO:74.; and (c) an isolated nucleic acid fragment that is complementary to (a) or (b). The nucleic acid fragments and corresponding polypeptides are contained in the accompanying Sequence Listing and described in the Brief Description of the Invention.

In another embodiment, the instant invention relates to chimeric genes encoding maize GST enzymes or to chimeric genes that comprise nucleic acid fragments as described above, the chimeric genes operably linked to suitable regulatory sequences, wherein expression of the chimeric genes results in altered levels of the encoded enzymes in transformed host cells.

The present invention further provides a transformed host cell comprising the above described chimeric gene. The transformed host cells can be of eukaryotic or prokaryotic origin. The invention also includes transformed plants that arise from transformed host cells of higher plants, and from seeds derived from such transformed plants, and subsequent progeny.

Additionally, the invention provides methods of altering the level of expression of a maize GST enzyme in a host cell comprising the steps of; (i) transforming a host cell with the above described chimeric gene and; (ii) growing the transformed host cell produced in step (i) under conditions that are suitable for expression of the chimeric gene wherein expression of the chimeric gene results in production of altered levels of a plant GST enzyme in the transformed host cell relative to expression levels of an untransformed host cell.

In an alternate embodiment, the present invention provides methods of obtaining a nucleic acid fragment encoding all or substantially all of the amino acid sequence encoding a maize GST enzyme comprising either hybridization or primer-directed amplification methods known in the art and using the above described nucleic acid fragment. A primer-amplification-based method uses SEQ ID NOS.:1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71 or 73. The product of these methods is also part of the invention.

Another embodiment of the invention includes a method for identifying a compound that inhibits the activity of a maize GST enzyme encoded by the nucleic acid fragment and substantially similar and complementary nucleic acid fragments of SEQ ID NOS.:1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71 and 73. The method has the steps: (a) transforming a host cell with the above described chimeric gene; (b) growing the transformed host cell under conditions that are suitable for expression of the chimeric gene wherein expression of the chimeric gene results in production of the GST enzyme; (c) optionally purifying the GST enzyme expressed by the transformed host cell; (d) contacting the GST enzyme with a chemical compound of interest; and (e) identifying the chemical compound of interest that reduces the activity of the maize GST enzyme relative to the activity of the maize GST enzyme in the absence of the chemical compound of interest.

This method may further include conducting step (d) in the presence of at least one electrophilic substrate and at least one thiol donor. The isolated nucleic acid fragments of this method are chosen from the group represented by SEQ ID NOS.:1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71 and 73 and the maize GST enzyme is selected from the group consisting of SEQ ID NOS.:2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, and 74.

The invention further provides a method for identifying a chemical compound that inhibits the activity of the maize GST enzyme as described herein, wherein the identification is based on a comparison of the phenotype of a plant transformed with the above described chimeric gene contacted with the inhibitor candidate with the phenotype of a transformed plant that is not contacted with the inhibitor candidate. The isolated nucleic acid fragment of this method is selected from the group consisting of SEQ ID NOS.:1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71 and 73 and the maize GST enzyme is selected from the group consisting of SEQ ID NOS.:2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, and 74.

In another embodiment, the invention provides a method for identifying a substrate for the maize GST enzyme. The method comprises the steps of: (a) transforming a host cell with a chimeric gene comprising the nucleic acid fragment as described herein, the chimeric gene encoding a maize GST enzyme operably linked to at least one suitable regulatory sequence; (b) growing the transformed host cell of step (a) under conditions that are suitable for expression of the chimeric gene resulting in production of the GST enzyme; (c) optionally purifying the GST enzyme expressed by the transformed host cell; (d) contacting the GST enzyme with a substrate candidate; and (e) comparing the activity of maize GST enzyme with the activity of maize GST enzyme that has been contacted with the substrate candidate and selecting substrate candidates that increase the activity of the maize GST enzyme relative to the activity of maize GST enzyme in the absence of the substrate candidate. More preferably, step (d) of this method is carried out in the presence of at least one thiol donor. The isolated nucleic acid fragment of this method is selected from the group consisting of SEQ ID NOS.:1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71 and 73 and the maize GST enzyme is selected from the group consisting of SEQ ID NOS.:2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, and 74.

Alternatively, methods are provided for identifying a maize GST substrate candidate wherein the identification of the substrate candidate is based on a comparison of the phenotype of a host cell transformed with a chimeric gene expressing a maize GST enzyme and contacted with a substrate candidate with the phenotype of a similarly transformed host cell grown without contact with a substrate candidate.

The isolated nucleic acid fragment of this method is selected from the group consisting of SEQ ID NOS.:1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71 and 73 and the maize GST enzyme is selected from the group consisting of SEQ ID NOS.:2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, and 74.

BRIEF DESCRIPTION OF SEQUENCE DESCRIPTIONS AND BIOLOGICAL DEPOSITS

The invention can be more fully understood from the following detailed description and the accompanying sequence descriptions and biological deposits which form a part of this application.

The following sequence descriptions and sequences listings attached hereto comply with the rules governing nucleotide and/or amino acid sequence disclosures in patent applications as set forth in 37 C.F.R. §1.821–1.825. The Sequence Descriptions contain the one letter code for nucleotide sequence characters and the three letter codes for amino acids as defined in conformity with the IUPAC-IYUB standards described in Nucleic Acids Research 13:3021–3030 (1985) and in the Biochemical Journal 219 (No. 2):345–373 (1984) which are herein incorporated by reference.

SEQ ID NO:1 is the nucleotide sequence comprising the cDNA insert in clone bms1.pk0023.g8 encoding a maize GST.

SEQ ID NO:2 is the deduced amino acid sequence of the nucleotide sequence comprising the cDNA insert in clone bms1.pk0023.g8.

SEQ ID NO:3 is the nucleotide sequence comprising the cDNA insert in clone cs.pk0010.c5 encoding a maize GST.

SEQ ID NO:4 is the deduced amino acid sequence of the nucleotide sequence comprising the cDNA insert in clone cs.pk0010.c5.

SEQ ID NO:5 is the nucleotide sequence comprising the cDNA insert in clone ceb1.pk0017.a5 encoding a maize GST.

SEQ ID NO:6 is the deduced amino acid sequence of the nucleotide sequence comprising the cDNA insert in clone ceb1.pk0017.a5.

SEQ ID NO:7 is the nucleotide sequence comprising the cDNA insert in clone cc71se-a.pk0001.g2 encoding a maize class III GST.

SEQ ID NO:8 is the deduced amino acid sequence of the nucleotide sequence comprising the cDNA insert in clone cc71se-a.pk0001.g2.

SEQ ID NO:9 is the nucleotide sequence comprising the cDNA insert in clone cc71se-b.pk0014.b8 encoding a maize class III GST.

SEQ ID NO:10 is the deduced amino acid sequence of the nucleotide sequence comprising the cDNA insert in clone cc71se-b.pk0014.b8.

SEQ ID NO:11 is the nucleotide sequence comprising the cDNA insert in clone ceb5.pk0051.f8 encoding a maize class III GST.

SEQ ID NO:12 is the deduced amino acid sequence of the nucleotide sequence comprising the cDNA insert in clone ceb5.pk0051.f8.

SEQ ID NO:13 is the nucleotide sequence comprising the cDNA insert in clone cr1n.pk0003.b1 encoding a maize class III GST.

SEQ ID NO:14 is the deduced amino acid sequence of the nucleotide sequence comprising the cDNA insert in clone cr1n.pk0003.b1.

SEQ ID NO:15 is the nucleotide sequence comprising the cDNA insert in clone cr1n.pk0014.g8 encoding a maize class III GST.

SEQ ID NO:16 is the deduced amino acid sequence of the nucleotide sequence comprising the cDNA insert in clone cr1n.pk0014.g8.

SEQ ID NO:17 is the nucleotide sequence comprising the cDNA insert in clone m.15.5.d06.sk20 encoding a maize class II GST.

SEQ ID NO:18 is the deduced amino acid sequence of the nucleotide sequence comprising the cDNA insert in clone m.15.5.d06.sk20.

SEQ ID NO:19 is the nucleotide sequence comprising the cDNA insert in clone cr1n.pk0040.e12 encoding a maize class II GST.

SEQ ID NO:20 is the deduced amino acid sequence of the nucleotide sequence comprising the cDNA insert in clone cr1n.pk0040.e12.

SEQ ID NO:21 is the nucleotide sequence comprising the cDNA insert in clone ceb5.pk0049.a11 encoding a maize class III GST.

SEQ ID NO:22 is the deduced amino acid sequence of the nucleotide sequence comprising the cDNA insert in clone ceb5.pk0049.a11.

SEQ ID NO:23 is the nucleotide sequence comprising the cDNA insert in clone cs1.pk0059.e2 encoding a maize class III GST.

SEQ ID NO:24 is the deduced amino acid sequence of the nucleotide sequence comprising the cDNA insert in clone cs1.pk0059.e2.

SEQ ID NO:25 is the nucleotide sequence comprising the cDNA insert in clone cbn2.pk0032.d10 encoding a maize class I GST.

SEQ ID NO:26 is the deduced amino acid sequence of the nucleotide sequence comprising the cDNA insert in clone cbn2.pk0032.d10

SEQ ID NO:27 is the nucleotide sequence comprising the cDNA insert in clone cr1n.pk0164.g7 encoding a maize class I GST.

SEQ ID NO:28 is the deduced amino acid sequence of the nucleotide sequence comprising the cDNA insert in clone cr1n.pk0164.g7

SEQ ID NO:29 is the nucleotide sequence comprising the cDNA insert in clone cdt2c.pk003.115 encoding a maize class I GST.

SEQ ID NO:30 is the deduced amino acid sequence of the nucleotide sequence comprising the cDNA insert in clone cdt2c.pk003.115

SEQ ID NO:31 is the nucleotide sequence comprising the cDNA insert in clone csc1c.pk001.h7 encoding a maize class I GST.

SEQ ID NO:32 is the deduced amino acid sequence of the nucleotide sequence comprising the cDNA insert in clone csc1c.pk001.h7

SEQ ID NO:31 is the nucleotide sequence comprising the cDNA insert in clone csc1c.pk001.h7 encoding a maize class I GST.

SEQ ID NO:32 is the deduced amino acid sequence of the nucleotide sequence comprising the cDNA insert in clone csc1c.pk001.h7

SEQ ID NO: 33 is the nucleotide sequence comprising the cDNA insert in clone p0110.cgsnt78r encoding a maize class I GST.

SEQ ID NO:34 is the deduced amino acid sequence of the nucleotide sequence comprising the cDNA insert in clone p0110.cgsnt78r.

SEQ ID NO:35 is the nucleotide sequence comprising the cDNA insert in clone p0121.cfrmz42r encoding a maize class I GST.

SEQ ID NO:36 is the deduced amino acid sequence of the nucleotide sequence comprising the cDNA insert in clone p0121.cfrmz42r.

SEQ ID NO:37 is the nucleotide sequence comprising the cDNA insert in clone csi1n.pk0034.a11 encoding a maize class III GST.

SEQ ID NO:38 is the deduced amino acid sequence of the nucleotide sequence comprising the cDNA insert in clone csi1n.pk0034.a11.

SEQ ID NO:39 is the nucleotide sequence comprising the cDNA insert in clone cepe7.pk0028.g3 encoding a maize class III GST.

SEQ ID NO:40 is the deduced amino acid sequence of the nucleotide sequence comprising the cDNA insert in clone cepe7.pk0028.g3.

SEQ ID NO:41 is the nucleotide sequence comprising the cDNA insert in clone cr1n.pk0167.d7 encoding a maize class III GST.

SEQ ID NO:42 is the deduced amino acid sequence of the nucleotide sequence comprising the cDNA insert in clone cr1n.pk0167.d7.

SEQ ID NO:43 is the nucleotide sequence comprising the cDNA insert in clone cco1.pk0027.e4 encoding a maize class III GST.

SEQ ID NO:44 is the deduced amino acid sequence of the nucleotide sequence comprising the cDNA insert in clone cco1.pk0027.e4.

SEQ ID NO:45 is the nucleotide sequence comprising the cDNA insert in clone cpj1c.pk001.d21 encoding a maize class III GST.

SEQ ID NO:46 is the deduced amino acid sequence of the nucleotide sequence comprising the cDNA insert in clone cpj1c.pk001.d21.

SEQ ID NO:47 is the nucleotide sequence comprising the cDNA insert in clone cse1c.pk001.b8 encoding a maize class III GST.

SEQ ID NO:48 is the deduced amino acid sequence of the nucleotide sequence comprising the cDNA insert in clone cse1c.pk001.b8.

SEQ ID NO:49 is the nucleotide sequence comprising the cDNA insert in clone cr1s.pk010.f1 encoding a maize class III GST.

SEQ ID NO:50 is the deduced amino acid sequence of the nucleotide sequence comprising the cDNA insert in clone cr1s.pk010.f1.

SEQ ID NO:51 is the nucleotide sequence comprising the cDNA insert in clone cpf1c.pk002.a13 encoding a maize class III GST.

SEQ ID NO:52 is the deduced amino acid sequence of the nucleotide sequence comprising the cDNA insert in clone cpf1c.pk002.a13.

SEQ ID NO:53 is the nucleotide sequence comprising the cDNA insert in clone cho1c.pk004.c15 encoding a maize class III GST.

SEQ ID NO:54 is the deduced amino acid sequence of the nucleotide sequence comprising the cDNA insert in clone cho1c.pk004.c15.

SEQ ID NO:55 is the nucleotide sequence comprising the cDNA insert in clone cpi1c.pk002.m4 encoding a maize class III GST.

SEQ ID NO:56 is the deduced amino acid sequence of the nucleotide sequence comprising the cDNA insert in clone cpi1c.pk002.m4.

SEQ ID NO:57 is the nucleotide sequence comprising the cDNA insert in clone chpc8.pk057.f10 encoding a maize class III GST.

SEQ ID NO:58 is the deduced amino acid sequence of the nucleotide sequence comprising the cDNA insert in clone chpc8.pk057.f10.

SEQ ID NO:59 is the nucleotide sequence comprising the cDNA insert in clone p0014.ctu90r encoding a maize class III GST.

SEQ ID NO:60 is the deduced amino acid sequence of the nucleotide sequence comprising the cDNA insert in clone p0014.ctu90r.

SEQ ID NO:61 is the nucleotide sequence comprising the cDNA insert in p0006.cbyvs55r encoding a maize class III GST.

SEQ ID NO:62 is the deduced amino acid sequence of the nucleotide sequence comprising the cDNA insert in clone p0006.cbyvs55r.

SEQ ID NO:63 is the nucleotide sequence comprising the cDNA insert in p0037.crwaf68r encoding a maize class III GST.

SEQ ID NO:64 is the deduced amino acid sequence of the nucleotide sequence comprising the cDNA insert in clone p0037.crwaf68r.

SEQ ID NO:65 is the nucleotide sequence comprising the cDNA insert in p0032.crcas61r encoding a maize class III GST.

SEQ ID NO:66 is the deduced amino acid sequence of the nucleotide sequence comprising the cDNA insert in clone p0032.crcas61r.

SEQ ID NO:67 is the nucleotide sequence comprising the cDNA insert in p0088.clrim45r encoding a maize class III GST.

SEQ ID NO:68 is the deduced amino acid sequence of the nucleotide sequence comprising the cDNA insert in clone p0088.clrim45r.

SEQ ID NO:69 is the nucleotide sequence comprising the cDNA insert in p0126.cnlag50r encoding a maize class III GST.

SEQ ID NO:70 is the deduced amino acid sequence of the nucleotide sequence comprising the cDNA insert in clone p0126.cnlag50r.

SEQ ID NO:71 is the nucleotide sequence comprising the cDNA insert in p0095.cwsba73r encoding a maize class III GST.

SEQ ID NO:72 is the deduced amino acid sequence of the nucleotide sequence comprising the cDNA insert in clone p0095.cwsba73r.

SEQ ID NO:73 is the nucleotide sequence comprising the cDNA insert in p0125.czaaj03r encoding a maize class III GST.

SEQ ID NO:74 is the deduced amino acid sequence of the nucleotide sequence comprising the cDNA insert in clone p0125.czaaj03r.

The transformed *E. coli* ceb5.pk0051.f8/pET30(LIC) BL21(DE3) containing the gene ceb5.pk0051.f8 in a pET30 (LIC) vector encoding a maize class III GST was deposited on Aug. 21, 1997 with the American Type Culture Collection (ATCC), 10801 University Boulevard, Manassas, Va. 20110-2209, U.S.A., under the terms of the Budapest Treaty on the International Recognition of the Deposit of Microorganisms for the Purpose of Patent Procedure. The deposit is designated as ATCC 98511.

DETAILED DESCRIPTION OF THE INVENTION

The present invention provides novel GST nucleotide sequences and encoded proteins isolated from maize. GST enzymes are known to function in the process of detoxification of a variety of xenobiotic compounds in plants, most notably, herbicides. Nucleic acid fragments encoding at least a portion of several maize GST enzymes have been isolated and identified by comparison of random plant cDNA sequences to public databases containing nucleotide and protein sequences using the BLAST algorithms well known to those skilled in the art. The sequences of the present invention are useful in the construction of herbicide-tolerant transgenic plants, in the recombinant production of GST enzymes, in the development of screening assays to identify compounds inhibitory to the GST enzymes, and in screening assays to identify chemical substrates of the GSTs.

In the context of this disclosure, a number of terms shall be utilized.

As use herein "Glutathione S-Transferase" or "GST" refers to any plant derived glutathione S-transferase (GST) enzyme capable of catalyzing the conjugation of glutathione, homoglutathione and other glutathione-like analogs via a sulfhydryl group, to hydrophobic and electrophilic compounds. The term GST includes amino acid sequences longer or shorter than the length of natural GSTs, such as functional hybrid or partial fragments of GSTs, or their analogues. As used herein "GST" is not intended to be delimited on the basis of enzyme activity but may encompass amino acid sequences that possess no measurable enzyme activity but are substantially similar in to those sequences, known in the art to possess the above mentioned glutathione conjugating activity.

The term "class" or "GST class" refers to a grouping of the various GST enzymes according to amino acid identity. Currently, four classes have been identified and are referred to as "GST class I" "GST class II", "GST class III" and "GST class IV". The grouping of plant GSTs into three classes is described by Droog et al. (*Plant Physiology* 107:1139–1146 (1995)). All available amino acid sequences were aligned using the Wisconsin Genetics Computer Group package (Wisconsin Package Version 9.0, Genetics Computer Group (GCG), Madison, Wis.), and graphically represented on a phylogenetic tree. Three groups were identified: class one including the archetypical sequences from maize GST I (X06755) and GST III (X04375); class two including the archetypical sequence from *Dianthus caryophyllus* (M64628); and class three including the archetypical sequence soybean GH2/4 (M20363). Recently, Applicants have established a further subgroup of the plant GSTs known as class IV GSTs with its archetypical sequence being In2-1 (X58573).

As used herein, an "isolated nucleic acid fragment" is a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA.

As used herein, "substantially similar" refers to nucleic acid fragments wherein changes in one or more nucleotide bases results in substitution of one or more amino acids, but do not affect the functional properties of the protein encoded by the DNA sequence. "Substantially similar" also refers to nucleic acid fragments wherein changes in one or more nucleotide bases does not affect the ability of the nucleic acid fragment to mediate alteration of gene expression by antisense or co-suppression technology. "Substantially similar" also refers to modifications of the nucleic acid fragments of the instant invention such as deletion or insertion of one or more nucleotide bases that do not substantially affect the functional properties of the resulting transcript vis-à-vis the ability to mediate alteration of gene expression by antisense or co-suppression technology or alteration of the functional properties of the resulting protein molecule. It is therefore understood that the invention encompasses more than the specific exemplary sequences.

For example, it is well known in the art that antisense suppression and co-suppression of gene expression may be accomplished using nucleic acid fragments representing less that the entire coding region of a gene, and by nucleic acid fragments that do not share 100% identity with the gene to be suppressed. Moreover, alterations in a gene which result in the production of a chemically equivalent amino acid at a given site, but do not effect the functional properties of the encoded protein, are well known in the art. Thus, a codon for the amino acid alanine, a hydrophobic amino acid, may be substituted by a codon encoding another less hydrophobic residue (such as glycine) or a more hydrophobic residue (such as valine, leucine, or isoleucine). Similarly, changes which result in substitution of one negatively charged residue for another (such as aspartic acid for glutamic acid) or one positively charged residue for another (such as lysine for arginine) can also be expected to produce a functionally equivalent product. Nucleotide changes which result in alteration of the N-terminal and C-terminal portions of the protein molecule would also not be expected to alter the activity of the protein. Each of the proposed modifications is well within the routine skill in the art, as is determination of retention of biological activity of the encoded products. Moreover, the skilled artisan recognizes that substantially similar sequences encompassed by this invention are also defined by their ability to hybridize, under stringent conditions (0.1×SSC, 0.1% SDS, 65° C.), with the sequences exemplified herein. Preferred substantially similar nucleic acid fragments of the instant invention are those nucleic acid fragments whose DNA sequences are at least 80% identical to the DNA sequence of the nucleic acid fragments reported herein. More preferred nucleic acid fragments are at least 95% identical to the DNA sequence of the nucleic acid fragments reported herein.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength. Hybridization and washing conditions are well known and exemplified in Sambrook, J., Fritsch, E. F. and Maniatis, T. *Molecular Cloning: A Laboratory Manual*, Second Edition, Cold Spring Harbor Laboratory Press, Cold Spring Harbor (1989), particularly Chapter 11 and Table 11.1 therein (entirely incorporated herein by reference). The conditions of temperature and ionic strength determine the "stringency" of the hybridization. For preliminary screening for homologous nucleic acids, low stringency hybridization conditions, corresponding to a Tm of 55°, can be used, e.g., 5×SSC, 0.1% SDS, 0.25% milk, and no formamide; or 30% formamide, 5×SSC, 0.5% SDS. Moderate stringency hybridization conditions correspond to a higher Tm, e.g., 40% formamide, with 5× or 6×SSC. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (see Sambrook et al., supra, 9.50–9.51). For hybridizations with shorter nucleic acids, i.e., oligonucleotides, the position of mismatches becomes more important, and the length of the oligonucleotide determines its specificity (see Sambrook et al., supra, 11.7–11.8). In one embodiment the length for a hybridizable nucleic acid is at least about 10 nucleotides. Preferable a minimum length for a hybridizable nucleic acid is at least about 15 nucleotides; more preferably at least about 20 nucleotides; and most preferably the length is at least 30 nucleotides. Furthermore, the skilled artisan will recognize that the temperature and wash solution salt concentration may be adjusted as necessary according to factors such as length of the probe.

A "substantial portion" of an amino acid or nucleotide sequence comprising enough of the amino acid sequence of a polypeptide or the nucleotide sequence of a gene to putatively identify that polypeptide or gene, either by manual evaluation of the sequence by one skilled in the art, or by computer-automated sequence comparison and identification using algorithms such as BLAST (Basic Local Alignment Search Tool; Altschul, S. F., et al., (1993) *J. Mol Biol.* 215:403–410; see also www.ncbi.nlm.nih.gov/BLAST/). In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene specific oligonucleotide probes comprising 20–30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12–15 bases may be used as amplification primers in PCR in order to obtain a particular nucleic acid fragment comprising the primers. Accordingly, a "substantial protion" of a nucleotide sequence comprises enough of the sequence to specifically identify and/or isolate a nucleic acid fragment comprising the sequence. The instant specification teaches partial or complete amino acid and nucleotide sequences encoding one or more particular fungal proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

The term "percent identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: *Computational Molecular Biology* (Lesk, A. M., ed.) Oxford University Press, New York (1988); *Biocomputing: Informatics and Genome Projects* (Smith, D. W., ed.) Academic Press, New York (1993); *Computer Analysis of Sequence Data, Part I* (Griffin, A. M., and Griffin, H. G., eds.) Humana Press, New Jersey (1994); *Sequence Analysis in Molecular Biology* (von Heinje, G., ed.) Academic Press (1987); and *Sequence Analysis Primer* (Gribskov, M. and Devereux, J., eds.) Stockton Press, New York (1991). Preferred methods to determine identity are designed to give the largest match between the sequences tested. Methods to determine identity and similarity are codified in publicly available computer programs. Preferred computer program methods to determine identity and similarity between two sequences include, but are not limited to, the GCG Pileup program found in the GCG program package, as used in the instant invention, using the Needleman and Wunsch algorithm with their standard default values of gap creation penalty=12 and gap extension penalty=4 (Devereux et al., *Nucleic Acids Res.* 12:387–395 (1984)), BLASTP, BLASTN, and FASTA (Pearson et al., *Proc. Natl. Acad Sci. U.S.A.* 85:2444–2448 (1988). The BLAST X program is publicly available from NCBI and other sources (*BLAST Manual*, Altschul et al., Natl. Cent. Biotechnol. Inf., Natl. Library Med. (NCBI NLM) NIH, Bethesda, Md. 20894; Altschul et al., *J. Mol. Biol* 215:403–410 (1990)). Another preferred method to determine percent identity, is by the method of DNASTAR protein alignment protocol using the Jotun-Hein algorithm (Hein et al., *Methods Enzymol.* 183:626–645 (1990)). Default parameters for the Jotun-Hein method for alignments are: for multiple alignments, gap penalty=11, gap length penalty=3; for pairwise alignments ktuple=6. As an illustration, by a polynucleotide having a nucleotide sequence having at least, for example, 95% "identity" to a reference nucleotide sequence of SEQ ID NO:1 it is intended that the nucleotide sequence of the polynucleotide is identical to the reference sequence except that the polynucleotide sequence may include up to five point mutations per each 100 nucleotides of the reference nucleotide sequence of SEQ ID NO:1. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence. Analogously, by a polypeptide having an amino acid sequence having at least, for example, 95% identity to a reference amino acid sequence of SEQ ID NO:2 is intended that the amino acid sequence of the polypeptide is identical to the reference sequence except that the polypeptide sequence may include up to five amino acid alterations per each 100 amino acids of the reference amino acid of SEQ ID NO:2. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

The term "complementary" is used to describe the relationship between nucleotide bases that are capable to hybridizing to one another. For example, with respect to DNA, adenosine is complementary to thymine and cytosine is complementary to guanine. Accordingly, the instant invention also includes isolated nucleic acid fragments that are complementary to the complete sequences as reported in the accompanying Sequence Listing as well as those substantially similar nucleic acid sequences.

"Codon degeneracy" refers to divergence in the genetic code permitting variation of the nucleotide sequence without effecting the amino acid sequence of an encoded polypeptide. Accordingly, the instant invention relates to any nucleic acid fragment that encodes all or a substantial portion of the amino acid sequence encoding the GST enzymes as set forth in SEQ ID Nos: SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:72 and SEQ ID NO:74. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

"Synthetic genes" can be assembled from oligonucleotide building blocks that are chemically synthesized using procedures known to those skilled in the art These building blocks are ligated and annealed to form gene segments which are then enzymatically assembled to construct the entire gene. "Chemically synthesized", as related to a sequence of DNA, means that the component nucleotides were assembled in vitro. Manual chemical synthesis of DNA may be accomplished using well established procedures, or automated chemical synthesis can be performed using one of a number of commercially available machines. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a DNA sequence that codes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a DNA sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a DNA sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Promoters which cause a gene to be expressed in most cell types at most times are commonly referred to as "constitutive promoters". New promoters of various types useful in plant cells are constantly being discovered; numerous examples may be found in the compilation by Okamuro and Goldberg, (1989) *Biochemistry of Plants* 15:1–82. It is further recognized that since in most cases the exact boundaries of regulatory sequences have not been completely defined, DNA fragments of different lengths may have identical promoter activity.

The "translation leader sequence" refers to a DNA sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner, R. and Foster, G. D. (1995) *Molecular Biotechnology* 3:225).

The "3' non-coding sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al. ((1989) *Plant Cell* 1:671–680).

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into protein by the cell. "cDNA" refers to a double-stranded DNA that is complementary to and derived from mRNA. "Sense" RNA refers to RNA transcript that includes the mRNA and so can be translated into protein by the cell. "Antisense RNA" refers to a RNA transcript that is complementary to all or part of a target primary transcript or mRNA and that blocks the expression of a target gene (U.S. Pat. No. 5,107,065). The complementarity of an antisense RNA may be with any part of the specific gene transcript, i.e., at the 5' non-coding sequence, 3' non-coding sequence, introns, or the coding sequence. "Functional RNA" refers to antisense RNA, ribozyme RNA, or other RNA that is not translated yet has an effect on cellular processes.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020).

"Altered levels" refers to the production of gene product (s) in transgenic organisms in amounts or proportions that differ from that of normal or non-transformed organisms.

"Mature" protein refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be but are not limited to intracellular localization signals.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels, J. J., (1991) *Ann. Rev. Plant Phys. Plant Mol. Biol.* 42:21–53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) *Plant Phys.*100:1627–1632).

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include Agrobacterium-mediated transformation (De Blaere et al. (1987) *Meth Enzymol.* 143:277) and particle-accelerated or "gene gun" transformation technology (Klein et al. (1987) *Nature* (London) 327:70–73; U.S. Pat. No. 4,945,050).

The term "herbicide-tolerant plant" as used herein is defined as a plant that survives and preferably grows normally at a usually effective dose of a herbicide. Herbicide tolerance in plants according to the present invention refers to detoxification mechanisms in a plant, although the herbicide binding or target site is still sensitive.

"Thiol donor" refers to a compound that contains the structure RSH (where R is not equal to H). Within the context of the present invention suitable thiol donors may include, but are not limited to, Glutathione and homoglutathione.

"Electrophilic substrate" refers to a compound that is amenable to conjugation with glutathione or homoglutathione via a sulfhydryl group. Electrophilic substrates include a wide variety of compounds including pesticides, anti-pathogenic compounds such as fungicides and profungicides, pheromones, and herbicides. Within the context of the present invention electrophilic substrates with herbicidal activity may include, but are not limited to, chlorimuronethyl, alachlor, and atrazine, 1-chloro-2,4-dinitrobenzene (CDNB), ethacrynic acid, t-stilbene oxide, and 1,2-epoxy-3-(p-nitrophenoxy)propane.

Standard recombinant DNA and molecular cloning techniques used herein are well known in the art and are described more fully in Sambrook, J., Fritsch, E. F. and Maniatis, T. *Molecular Cloning: A Laboratory Manual*; Cold Spring Harbor Laboratory Press: Cold Spring Harbor, 1989 (hereinafter "Maniatis").

"Thiol donor" refers to a compound that contains the structure RSH (where R is not equal to H). Within the context of the present invention suitable thiol donors may include, but are not limited to, Glutathione and homoglutathione.

"Electrophilic substrate" refers to a compound that is amenable to conjugation with glutathione or homoglutathione via a sulfhydryl group. Electrophilic substrates include a wide variety of compounds including pesticides, anti-pathogenic compounds such as fungicides and profungicides, pheromones, and herbicides. Within the context of the present invention electrophilic substrates with herbicidal activity may include, but are not limited to, chlorimuronethyl, alachlor, and atrazine, 1-chloro-2,4-dinitrobenzene (CDNB), ethacrynic acid, t-stilbene oxide, and 1,2-epoxy-3-(p-nitrophenoxy)propane.

The nucleic acid fragments of the instant invention may be used to isolate cDNAs and genes encoding homologous enzymes from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other GST enzymes, either as cDNAs or genomic DNAs, could be isolated directly by using all or a portion of the instant nucleic acid fragments as DNA hybridization probes to screen libraries from any desired plant using methodology well known to those skilled in the art. Specific oligonucleotide probes based upon the instant nucleic acid sequences can be designed and synthesized by methods known in the art (Maniatis). Moreover, the entire sequences can be used directly to synthesize DNA probes by methods known to the skilled artisan such as random primers DNA labeling, nick translation, or end-labeling techniques, or RNA probes using available in vitro transcription systems. In addition, specific primers can be designed and used to amplify a part of or full-length of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman et al., (1988) *PNAS USA* 85:8998) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al., (1989) *PNAS USA* 86:5673; Loh et al., (1989) *Science* 243:217). Products generated by the 3' and 5' RACE procedures can be combined to generate full-length cDNAs (Frohman, M. A. and Martin, G. R., (1989) *Techniques* 1:165).

Availability of the instant nucleotide and deduced amino acid sequences facilitates immunological screening cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner, R. A. (1984) *Adv. Immunol.* 36:1; Maniatis).

The nucleic acid fragments of the instant invention may be used to create transgenic plants in which the disclosed GST enzymes are present at higher or lower levels than normal or in cell types or developmental stages in which they are not normally found. This would have the effect of altering the level of GST enzyme available as well as the herbicide tolerant-phenotype of the plant.

Overexpression of the GST enzymes of the instant invention may be accomplished by first constructing chimeric genes in which the coding region are operably linked to promoters capable of directing expression of a gene in the desired tissues at the desired stage of development. For reasons of convenience, the chimeric genes may comprise promoter sequences and translation leader sequences derived from the same genes. 3' Non-coding sequences encoding transcription termination signals must also be provided. The instant chimeric genes may also comprise one or more introns in order to facilitate gene expression.

Any combination of any promoter and any terminator capable of inducing expression of a GST coding region may be used in the chimeric genetic sequence. Some suitable examples of promoters and terminators include those from nopaline synthase (nos), octopine synthase (ocs) and cauliflower mosaic virus (CaMV) genes. One type of efficient plant promoter that may be used is a high level plant promoter. Such promoters, in operable linkage with the genetic sequence for GST, should be capable of promoting expression of the GST such that the transformed plant is tolerant to an herbicide due to the presence of, or increased levels of, GST enzymatic activity. High level plant promoters that may be used in this invention include the promoter of the small subunit (ss) of the ribulose-1,5-bisphosphate carboxylase from example from soybean (Berry-Lowe et al., *J. Molecular and App. Gen.*, 1:483–498 1982)), and the promoter of the chlorophyll a/b binding protein. These two promoters are known to be light-induced in plant cells (See, for example, *Genetic Engineering of Plants, an Agricultural Perspective*, A. Cashmore, Plenum, New York (1983), pages 29–38; Coruzzi, G. et al., *The Journal of Biological Chemistry*, 258:1399 (1983), and Dunsmuir, P. et al., *Journal of Molecular and Applied Genetics*, 2:285 (1983)).

Plasmid vectors comprising the instant chimeric genes can then constructed. The choice of plasmid vector depends upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al., (1985) *EMBO J.* 4:2411–2418; De Almeida et al., (1989) *Mol. Gen. Genetics* 218:78–86), and thus that multiple events must be screened in order to obtain lines displaying the desired expression level and pattern. Such screening may be accomplished by Southern analysis of DNA blots (Southern, *J. Mol. Biol.* 98, 503, (1975)). Northern analysis of mRNA expression (Kroczek, *J. Chromatogr. Biomed Appl.*, 618 (1–2) (1993) 133–145), Western analysis of protein expression, or phenotypic analysis.

For some applications it will be useful to direct the instant GST enzymes to different cellular compartments or to facilitate enzyme secretion from a recombinant host cell. It is thus envisioned that the chimeric genes described above may be further supplemented by altering the coding sequences to encode enzymes with appropriate intracellular targeting sequences such as transit sequences (Keegstra, K., *Cell* 56:247–253 (1989)), signal sequences or sequences encoding endoplasmic reticulum localization (Chrispeels, J. J., *Ann. Rev. Plant Phys. Plant Mol. Biol.* 42:21–53 (1991)), or nuclear localization signals (Raikhel, N. *Plant Phys.* 100:1627–1632 (1992)) added and/or with targeting sequences that are already present removed. While the references cited give examples of each of these, the list is not exhaustive and more targeting signals of utility may be discovered in the future that are useful in the invention.

It may also be desirable to reduce or eliminate expression of the genes encoding the instant GST enzymes in plants for some applications. In order to accomplish this, chimeric genes designed for co-suppression of the instant GST enzymes can be constructed by linking the genes or gene fragments encoding the enzymes to plant promoter sequences. Alternatively, chimeric genes designed to express antisense RNA for all or part of the instant nucleic acid fragments can be constructed by linking the genes or gene fragment in reverse orientation to plant promoter sequences. Either the co-suppression or antisense chimeric genes could be introduced into plants via transformation wherein expression of the corresponding endogenous genes are reduced or eliminated.

Plants transformed with the present GST genes will have a variety of phenotypes corresponding to the various properties conveyed by the GST class of proteins. Glutathione conjugation catalyzed by GSTs is known to result in sequestration and detoxification of a number of herbicides and other xenobiotics (Marrs et al., *Annu. Rev. Plant Physiol.*

Plant Mol. Biol. 47:127–58 (1996)) and thus will be expected to produce transgenic plants with this phenotype. Other GST proteins are known to be induced by various environmental stresses such as salt stress (Roxas, et al., *Stress tolerance in transgenic seedlings that overexpress glutathione S-transferase*, Annual Meeting of the American Society of Plant Physiologists, (August 1997), abstract 1574, Final Program, Plant Biology and Supplement to Plant Physiology, 301), exposure to ozone (Sharma et al., *Plant Physiology*, 105 (4) (1994) 1089–1096), and exposure to industrial pollutants such as sulfur dioxide (Navari-Izzo et al., *Plant Science* 96 (1–2) (1994) 31–40). It is contemplated that transgenic plants, tolerant to a wide variety of stresses, may be produced by the present method by expressing foreign GST genes in suitable plant hosts.

The instant GST enzymes produced in heterologous host cells, particularly in the cells of microbial hosts, can be used to prepare antibodies to the enzymes by methods well known to those skilled in the art. The antibodies are useful for detecting the enzymes in situ in cells or in vitro in cell extracts. Preferred heterologous host cells for production of the instant GST enzymes are microbial hosts. Microbial expression systems and expression vectors containing regulatory sequences that direct high level expression of foreign proteins are well known to those skilled in the art. Any of these could be used to construct chimeric genes for production of the instant GST enzymes. These chimeric genes could then be introduced into appropriate microorganisms via transformation to provide high level expression of the enzymes.

Vectors or cassettes useful for the transformation of suitable host cells are well known in the art. Typically the vector or cassette contains sequences directing transcription and translation of the relevant gene, a selectable marker, and sequences allowing autonomous replication or chromosomal integration. Suitable vectors comprise a region 5' of the gene which harbors transcriptional initiation controls and a region 3' of the DNA fragment which controls transcriptional termination. It is most preferred when both control regions are derived from genes homologous to the transformed host cell, although it is to be understood that such control regions need not be derived from the genes native to the specific species chosen as a production host.

Initiation control regions or promoters, which are useful to drive expression of the genes encoding the GST enzymes in the desired host cell are numerous and familiar to those skilled in the art. Virtually any promoter capable of driving these genes is suitable for the present invention including but not limited to CYC1, HIS3, GAL1, GAL10, ADH1, PGK, PHO5, GAPDH, ADC1, TRP1, URA3, LEU2, ENO, TPI (useful for expression in Saccharomyces); AOX1 (useful for expression in Pichia); and lac, trp, $\lambda P_L$, $\lambda P_R$, T7, tac, and trc (useful for expression in *E. coli*).

Termination control regions may also be derived from various genes native to the preferred hosts. Optionally, a termination site may be unnecessary, however, it is most preferred if included.

An example of a vector for high level expression of the instant GST enzymes in a bacterial host is provided (Example 5).

Additionally, the instant maize GST enzymes can be used as a targets to facilitate design and/or identification of inhibitors of the enzymes that may be useful as herbicides or herbicide synergists. This is desirable because the enzymes described herein catalyze the sulfhydryl conjugation of glutathione to compounds toxic to the plant. Conjugation can result in detoxification of these compounds. It is likely that inhibition of the detoxification process will result in inhibition of plant growth or plant death. Thus, the instant maize GST enzymes could be appropriate for new herbicide or herbicide synergist discovery and design All or a portion of the nucleic acid fragments of the instant invention may also be used as probes for genetically and physically mapping the genes that they are a part of, and as markers for traits linked to expression of the instant enzymes. Such information may be useful in plant breeding in order to develop lines with desired phenotypes or in the identification of mutants.

For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander et at., (1987) *Genomics* 1:174–181) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein et al., (1980) *Am. J. Hum. Genet.* 32:314–331).

The production and use of plant gene-derived probes for use in genetic mapping are described by Bernatzky, R. and Tanksley, S. D. (*Plant Mol. Biol. Reporter* 4(1):37–41 (1986)). Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel et al., In: *Nonmammalian Genomic Analysis: A Practical Guide*, Academic press 1996, pp. 319–346, and references cited therein).

In another embodiment, nucleic acid probes derived from the instant nucleic acid sequences may be used in direct fluorescence in situ hybridization (FISH) mapping. Although current methods of FISH mapping favor use of large clones (several to several hundred KB), improvements in sensitivity may allow performance of FISH mapping using shorter probes.

A variety of nucleic acid amplification-based methods of genetic and physical mapping may be carried out using the instant nucleic acid sequences. Examples include allele-specific amplification, polymorphism of PCR-amplified fragments (CAPS), allele-specific ligation, nucleotide extension reactions, Radiation Hybrid Mapping and Happy Mapping. For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence.

This, however, this is generally not necessary for mapping methods. Such information may be useful in plant breeding in order to develop lines with desired starch phenotypes.

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

GENERAL METHODS

Standard recombinant DNA and molecular cloning techniques used in the Examples are well known in the art and are described by Sambrook, J., Fritsch, E. F. and Maniatis, T. *Molecular Cloning: A Laboratory Manual;* Cold Spring Harbor Laboratory Press: Cold Spring Harbor, (1989) (Maniatis) and by T. J. Silhavy, M. L. Bennan, and L. W. Enquist, Experiments with Gene Fusions, Cold Spring Harbor Laboratory, Cold Spring Harbor, N.Y. (1984) and by Ausubel, F. M. et al., Current Protocols in Molecular Biology, pub. by Greene Publishing Assoc. and Wiley-Interscience (1987).

Example 1
Composition of cDNA Libraries; Isolation and Sequencing of cDNA Clones cDNA libraries representing mRNAs from various maize tissues were prepared. The characteristics of the libraries are described in Table 1.

TABLE 1 cDNA Libraries From Corn Tissues

| Library | GST Class | Clone | Tissue |
|---|---|---|---|
| bms1 | I | bms1.pk0023.g8 | Maize BMS cell culture 1 day after subculture |
| cs1 | I | cs1.pk0010.c5 | Maize leaf, sheath 5 wk plant Stratogene #837201 |
| ceb1 | I | ceb1.pk0017.a5 | Maize embryo |
| cc71se | III | cc71se-a.pk0001.g2 | Maize class II callus tissue, somatic embryo formed, highly transformable |
| cc71se | III | cc71se-b.pk0014.b8 | Maize class II callus tissue, somatic embryo formed, highly transformable |
| ceb5 | III | ceb5.pk0051.f8 | Amplified maize embryo 30 day |
| cr1n | III | cr1n.pk0003.b1 | Maize root from 7 day seedlings grown in light normalized |
| cr1n | III | cr1n.pk0014.g8 | Maize root from 7 day seedlings grown in light normalized |
| m | II | m.15.5.d06.sk20 | Maize 15 day embryo library |
| cr1n | II | cr1n.pk0040.e12 | Maize root from 7 day seedlings grown in light normalized |
| ceb5 | III | ceb5.pk0049.a11 | Amplified maize embryo 30 day |
| cs1 | III | cs1.pk0059.e2 | Maize leaf, sheath 5 wk plant Stratogene #837201 |
| cbn2 | gst I | cbn2.pk0032.d10 | Corn (*Zea mays* L.) developing kernel two days after pollination |
| cr1n | gst I | cr1n.pk0164.g7 | Corn (*Zea mays* L.) root from 7 day seedlings grown in light normalized |

TABLE 1-continued cDNA Libraries From Corn Tissues

| Library | GST Class | Clone | Tissue |
|---|---|---|---|
| cdt2 | gst I | cdt2c.pk003.l15 | Corn (*Zea mays* L.) developing tassel 2 |
| csc1c | gst I | csc1c.pk001.h7 | Corn (*Zea mays* L., B73) 20 day seedling (germination cold stress). The seedling appeared purple. |
| p0110 | gst I | p0110.cgsnt78r | Corn (*Zea mays* L. B73) salacylic acid infiltrated V3/V4 leaf tissue (minus midrib), screened 1 pool of A63 + SA 4 h; A63 + SA 24 hr; and A63 + SA 7 days |
| . p0121 | gst I | p0121.cfrmz42r | Corn (*Zea mays* L.) shank tissue collected from ears 5DAP, Screened 1 |
| csi1n | gst III | csi1n.pk0034.a11 | Corn (*Zea mays* L.) silk; normalized from csi1 library |
| cepe7 | gst III | cepe7.pk0028.g3 | Corn (*Zea mays* L.) epicotyl from 7 day old etiolated seedling |
| cr1n | gst III | cr1n.pk0167.d7 | Corn (*Zea mays* L.) root from 7 day seedlings grown in light normalized |
| cco1 | gst III | cco1.pk0027.e4 | Corn (*Zea mays* L.) cob of 67 day old plants grown in green house |
| cpj1c | gst III | cpj1c.pk001.d21 | Corn (*Zea mays* L.) pooled black mexican sweetcorn treated with chemicals related to membrane ionic force |
| cse1c | gst III | cse1c.pk001.b8 | Corn (*Zea mays* L.) seedling at V2 stage treated with Ethylene collected at 6 hr, 23 hr, 72 hr |
| cr1s | gst III | cr1s.pk010.f1 | Corn (*Zea mays* L., Lh132) root from 7 day old etiolated seedlings |
| cpf1c | gst III | cpf1c.pk002.a13 | Corn (*Zea mays* L.) pooled black mexican sweetcorn treated with chemicals related to protein synthesis |
| cho1c | gst III | cho1c.pk004.c15 | Corn (*Zea mays* L., Alexho Synthetic High Oil) embryo 20 DAP |
| cpi1c | gst III | cpi1c.pk002.m4 | Corn (*Zea mays* L.) pooled black mexican sweetcorn treated with chemicals related to biochemical compound synthesis |
| chpc8 | gst III | chpc8.pk057.f10 | Corn (*Zea mays* L., MBS847) 8 day old shoot treated with PDO herbicide MK593 collected 8 hrs after treatment. |
| p0014 | gst III | p0014.ctu90r | Corn (*Zea mays* L.) Leaf: Gene uaz151 (G-Protein), 413-8, no genetic lesions are formed. *C. heterostrophus* resistance, plant 3 ft tall, leaf 7 and leaf 8 |
| p0006 | gst III | p0006.cbyvs55r | Corn (*Zea mays* L.) Young shoot |
| p0037 | gst III | p0037.crwaf68r | Corn (*Zea mays* L.) corn Root Worm infested V5 roots |
| p0032 | gst III | p0032.crcas61r | Corn (*Zea mays* L.) Regenernerating callus, 10 and 14 days after auxin removal. Hi-II callus 223a, 1129e 10 days. Hi-II callus 223a, 1129e 14 days |
| p0088 | gst III | p0088.c1rim45r | Corn (*Zea mays* L.) Gene M1C07 (leucine-rich repeat), family 3-B7. about one month after planting in green house |
| p0126 | gst III | p0126.cn1ag50r | Corn (*Zea mays* L.) Night harvested leaf tissue; V8–V10 |
| p0095 | gst III | p0095.cwsba73r | Corn (*Zea mays* L.) Ear leaf sheath, screened 1 Growth conditions: field; control or |

TABLE 1-continued cDNA Libraries From Corn Tissues

| Library | GST Class | Clone | Tissue |
|---|---|---|---|
| | | | untreated tissues Growth stage: 2–3 weeks after pollen shed; plants were allowed to pollinate naturally |
| p0125 | gst III | p0125.czaaj03r | Corn (*Zea mays* L.) Anther: Prophase I sceened 1 | cDNA libraries were prepared in Uni-ZAP™ XR vectors according to the manufacturer's protocol (Stratagene Cloning Systems, La Jolla, Calif.). The Uni-ZAP™ XR libraries were converted into plasmid libraries according to the protocol provided by Stratagene. Upon conversion, cDNA inserts were contained in the plasmid vector pBluescript. cDNA inserts from randomly picked bacterial colonies containing recombinant pBluescript plasmids were amplified via polymerase chain reaction using primers specific for vector sequences flanking the inserted cDNA sequences. Amplified insert DNAs were sequenced in dye-primer sequencing reactions to generate partial cDNA sequences (expressed sequence tags or "ESTs"; see Adams, M. D. et al., (1991) *Science* 252:1651). The resulting ESTs were analyzed using a Perkin Elmer Model 377 fluorescent sequencer.

Example 2
Identification and Characterization of cDNA Clones cDNAs encoding maize GST enzymes were identified by conducting BLAST (Basic Local Alignment Search Tool; Altschul, S. F., et al., (1993) *J. Mol. Biol.* 215:403–410; see also www.ncbi.nlm.nih.gov/BLAST/) searches for similarity to sequences contained in the BLAST "nr" database (comprising all non-redundant GenBank CDS translations, sequences derived from the 3-dimensional structure Brookhaven Protein Data Bank, SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish, W. and States, D. J. (1993) *Nature Genetics* 3:266–272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

All comparisons were done using either the BLASTNnr or BLASTXnr algorithms. The results of the BLAST comparisons are given in Table 2 and summarize the clones and the sequences to which they have the most similarity. Table 2 displays data based on the BLASTNnr or BLASTXnr algorithm with values reported in pLogs or Exprect values. The Expect value estimates the statistical significance of the match, specifying the number of matches, with a given score, that are expected in a search of a database of this size absolutely by chance. Each cDNA identified encodes at least a portion of either a GST class I, II, or III. All isolated clones contain a fill length open reading frame (ORF) with the exception of cc71se-a.pk0001.g2 which is only a partial clone. Example 5 describes the sequencing strategy for the above described clones.

TABLE 2

BLAST Results For Clones
SEQ ID NO.

| Clone | GST Class | Similarity Identified | Base | Peptide | Blast Algorithm | pLog Score*/E-Value** | Citation |
|---|---|---|---|---|---|---|---|
| bms1.pk0023.g8 | I | X79515\|ZMGST27 *Z. mays* GST-27 mRNA for glutathione-S-transferase | 1 | 2 | Nnr | 122.086 | |
| cs1.pk0010.c5 | I | D17673\|ATHERD13 *Arabidopsis thaliana* mRNA for glutathione S-transferase | 3 | 4 | Nnr | 8.16 | |
| ceb1.pk0017.a5 | I | X78203\|HMGST *H. muticus* mRNA for glutathione S-transferase | 5 | 6 | Nnr | 21.51 | |
| cc71se-a.pk0001.g2 | III | (AF004358) glutathione S-transferase TSI-1 (*Aegilops squarrosa*) | 7 | 8 | Nnr | 16.48 | |
| cc71se-b.pk0014.b8 | III | D10861\|RICORFC Rice mRNA for a protein related to chilling tolerance. | 9 | 10 | Nnr | 14.96 | |
| ceb5.pk0051.f8 | III | D1086T\|RICORFC Rice mRNA for a protein related to chilling tolerance. | 11 | 12 | Nnr | 40.44 | |
| cr1n.pk0003.b1 | III | U80615\|EGU80615 *Eucalyptus globulus* auxin-induced protein (EgPar) mRNA, complete cds | 13 | 14 | Nnr | 24.70 | |
| cr1n.pk0014.g8 | III | M16901\|MZEGSTIB Maize glutathione S-transferase (GST-I) mRNA, complete cds | 15 | 16 | Nnr | 5.85 | |
| m.15.5.d06.sk20 | II | \|M97702\|DROGLUSTD *Drosophila melanogaster* glutathione S-transferase gene. | 17 | 18 | Nnr | 3.63 | |
| cr1n.pk0040.e12 | II | 167970 (L05915) (GST1) gene | 19 | 20 | Xnr | 42.03 | |

TABLE 2-continued

BLAST Results For Clones
SEQ ID NO.

| Clone | GST Class | Similarity Identified | Base | Peptide | Blast Algorithm | pLog Score*/E-Value** | Citation |
|---|---|---|---|---|---|---|---|
| ceb5.pk0049.a11 | III | product (*Dianthus caryophyllus*) \|Y12862\|ZYMY12862 Zea Maize mRNA for glutathione S-transferase | 21 | 22 | Nnr | 0.0 | |
| cs1.pk0059.e2 | III | D10861\|RICORFC Rice mRNA for a protein related to chilling tolerance. | 24 | 25 | Nnr | 41.03 | |
| cbn2.pk0032.d10 | gst I | (AC005309) glutathione s-transferase, GST6 [*Arabidopsis thaliana*] | 25 | 26 | Xnr | 4e–27 | unpublished |
| cr1n.pk0164.g7 | gst I | (AC005309) glutathione s-transferase, GST6 [*Arabidopsis thaliana*] | 27 | 28 | Xnr | 7e–37 | unpublished |
| cdec.pk003.115 | gst I | (AC005309) glutathione s-transferase, GST6 [*Arabidopsis thaliana*] | 29 | 30 | Xnr | 4e–36 | unpublished |
| csc1c.pk001.h7 | gst I | (U70672) glutathione S–transferase [*Arabidopsis thaliana*] | 31 | 32 | Xnr | 8e–34 | unpublished |
| p0110.cgsnt78r | gst I | P46420\|GTH4_MAIZE GLUTSTHION S-TRANSFERASE IV (GST-IV) (GS-27) | 33 | 34 | Xnr | 1e–97 | Plant Mol. Biol. 26 (6), 1855–1866 (1994) |
| p0121.cfrmz42r. | gst I | P42761\|GTH3_ARATH GLUTETHIONE S-TRANSFERASE ERD13 (CLASS PHI) | 35 | 36 | Xnr | 3e–28 | FEBS Lett. 335 (2), 189–192 (1993) |
| csi1n.pk0034.a11 | gst III | Q03664\|GTX3_TOBAC PROBABLE GLUTATHIONE S-TRANSFERASE (AUXIN-INDUCED PROTEIN PCNT103) | 37 | 38 | Xnr | 2e–51 | Plant Mol. Biol. 16 (6), 983–998 (1991) |
| cepe7.pk0028.g3 | gst III | (AF004358) glutathione S-transferase TSI-1 [*Aegilops squarrosa*] | 39 | 40 | Xnr | 9e–50 | Plant Physiol. 114, 1461–1470 (1997) |
| cr1n.pk0167.d7 | gst III | (AF004358) glutathione S-transferase TSI-1 [*Aegilops squarrosa*] | 41 | 42 | Xnr | 8e–58 | Plant Physiol. 114, 1461–1470 (1997) |
| cco1.pk0027.e4 | gst III | (Y12862) glutathione transferase [*Zea mays*] | 43 | 44 | Xnr | 2e–77 | JOURNAL Plant Mol. Biol. 36, 75–87 (1998) |
| cpj1c.pk001.d21 | gst III | \|Q03662\|GTX1_TOBAC PROBABLE GLUTATHIONE S-TRANSFERASE (AUXIN-INDUCED PROTEIN PGNT1/PCNT110) | 45 | 46 | Xnr | 1e–53 | Plant Mol. Biol. 16 (6), 983–998 (1991) |
| cse1c.pk001.b8 | gst III | (AF004358) glutathione S-transferase TSI-1 [*Aegilops squarrosa*] | 47 | 48 | Xnr | 3e–62 | Plant Physiol. 114, 1461–1470 (1997) |
| cr1s.pk010.f1 | gst III | P32110\|GTX6_SOYBN PROBABLE GLUTATHIONE S-TRANSFERASE (HEAT SHOCK PROTEIN 26A) | 49 | 50 | Xnr | 4e–49 | Mol. Cell. Biol. 8 (3), 1113–1122 (1988) |
| cpf1c.pk002.a13 | gst III | Q03662\|GTX1_TOBAC PROBABLE GLUTATHIONE S-TRANSFERASE (AUXIN-INDUCED PROTEIN PGNT1/PCNT110) | 51 | 52 | Xnr | 6e–47 | Plant Mol. Biol. 16 (6), 983–998 (1991) |
| cho1c.pk004.c15 | gst III | (AF004358) glutathione S-transferase TSI-1 [*Aegilops squarrosa*] | 53 | 54 | Xnr | 1e–59 | Plant Physiol. 114, 1461–1470 (1997) |
| cpi1c.pk002.m4 | gst III | (AF051214) probable glutathione S-transferase [*Picea mariana*] | 55 | 56 | Xnr | 7e–45 | Genetics 149 (2), 1089–1098 (1998) |
| chpc8.pk057.f10 | gst III | (AJ010449) glutathione transferase [*Alopecurus myosuroides*] | 57 | 58 | Xnr | 1e–62 | unpublished |
| p0014.ctu90r | gst III | (AJ010448) glutathione transferase [*Alopecurus myosuroides*] | 59 | 60 | Xnr | 8e–55 | unpublished |
| p0006.cbyvs55r | gst III | (AF051214) probable glutathione S-transferase [*Picea mariana*] | 61 | 62 | Xnr | 4e–51 | Genetics 149 (2), 1089–1098 (1998) |
| p0037.crwaf68r | gst III | (AF004358) glutathione S-transferase TSI-1 [*Aegilops squrrosa*] | 63 | 64 | Xnr | 2e–77 | Plant Physiol. 114, 1461–1470 (1997) |
| p0032.crcas61r | gst III | P32110 GTX6_SOYBN PROBABLE GLUTATHIONE S-TRANSFERASE (HEAT SHOCK PROTEIN 26A) | 65 | 66 | Xnr | 3e–48 | Mol. Cell. Biol. 8 (3), 1113–1122 (1988) |
| p0088.c1rim45r | gst III | (AF004358) glutathione S-transferase TSI-1 [*Aegilops squarrosa*] | 67 | 68 | Xnr | 3e–53 | Plant Physiol. 114, 1461–1470 (1997) |
| p0126.cn1ag50r | gst III | (AF004358) glutathione S-transferase TSI-1 [*Aegilops squarrosa*] | 69 | 70 | Xnr | 4e–52 | Plant Physiol. 114, 1461–1470 (1997) |
| p0095.cwsba73r | gst III | (AF004358) glutathione S-transferase TSI-1 [*Aegilops squarrosa*] | 71 | 72 | Xnr | 2e–57 | Plant Physiol. 114, 1461–1470 (1997) |
| p0125.czaaj03r | gst III | (AF004358) glutathione S-transferase TSI-1 [*Aegilops squarrosa*] | 73 | 74 | Xnr | 7E–63 | Plant Physiol. 114, 1461–1470 (1997) |

*Plog represents the negative of the logarithm of the reported P-value
**Expect value estimates the statistical significance of the match, specifying the number of matches, with a given score, that are expected in a search of a database of this size absolutely by chance.

Example 3
Expression of Chimeric Genes Encoding Maize GST Enzymes in Maize Cells (Monocotyledon)

A chimeric gene comprising a cDNA encoding a maize GST enzyme in sense orientation can be constructed by polymerase chain reaction (PCR) of the cDNA clone using appropriate oligonucleotide primers. Cloning sites (NcoI or SmaI) can be incorporated into the oligonucleotides to provide proper orientation of the DNA fragment when inserted into the digested vector pML103 as described below. Amplification is then performed in a 100 µL volume in a standard PCR mix consisting of 0.4 mM of each oligonucleotide and 0.3 pM of target DNA in 10 mM Tris-HCl, pH 8.3, 50 mM KCl, 1.5 mM $MgCl_2$, 200 mM dGTP, 200 mM dATP, 200 mM dTTP, 200 mM dCTP and 0.025 unit DNA polymerase. Reactions are carried out in a Perkin-Elmer Cetus Thermocycler™ for 30 cycles comprising 1 min at 95° C., 2 min at 55° C. and 3 min at 72° C., with a final 7 min extension at 72° C. after the last cycle. The amplified DNA is then digested with restriction enzymes NcoI and SmaI and fractionated on a 0.7% low melting point agarose gel in 40 mM Tris-acetate, pH 8.5, 1 mM EDTA. The appropriate band can be excised from the gel, melted at 68° C. and combined with a 4.9 kb NcoI-SmaI fragment of the plasmid pML103. Plasmid pML103 has been deposited under the terms of the Budapest Treaty at ATCC (American Type Culture Collection, 12301 Parklawn Drive, Rockville, Md. 20852), and bears accession number ATCC 97366. The DNA segment from pML103 contains a 1.05 kb SalI-NcoI promoter fragment of the maize 27 kD zein gene and a 0.96 kb SmaI-SalI fragment from the 3' end of the maize 10 kD zein gene in the vector pGem9Zf(+) (Promega Corp 7113 Benhart Dr, Raleigh, N.C.). Vector and insert DNA can be ligated at 15° C. overnight, essentially as described (Maniatis). The ligated DNA may then be used to transform *E. coli* XL1-Blue (*Epicurian Coli* XL-1; Stratagene). Bacterial transformants can be screened by restriction enzyme digestion of plasmid DNA and limited nucleotide sequence analysis using the dideoxy chain termination method DNA Sequencing Kit; U.S. Biochemical). The resulting plasmid construct would comprise a chimeric gene encoding, in the 5' to 3' direction, the maize 27 kD zein promoter, a cDNA fragment encoding a plant GST enzyme, and the 10 kD zein 3' region. The chimeric gene described above can then be introduced into corn cells by the following procedure. Immature corn embryos can be dissected from developing caryopses derived from crosses of the inbred corn lines H99 and LH132 (Indiana Agric. Exp. Station, Ind., USA). The embryos are isolated 10 to 11 days after pollination when they are 1.0 to 1.5 mm long. The embryos are then placed with the axis-side facing down and in contact with agarose-solidified N6 medium (Chu et al., (1975) *Sci. Sin.* Peking 18:659–668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks. The plasmid, p35S/Ac (obtained from Dr. Peter Eckes, Hoechst Ag, v Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell et al. (1985) Nature 313:810–812) and the 3M region of the nopaline synthase gene from the T-DNA of the Ti plasmid of Agrobacterium tumefaciens. The particle bombardment method (Klein et al., (1987) Nature 327:70–73) may be used to transfer genes to the callus culture cells. According to this method, gold particles ((1 µm in diameter) are coated with DNA using the following technique. Ten ug of plasmid DNAs are added to 50 uL of a suspension of gold particles (60 mg per mL). Calcium chloride (50 µL of a 2.5 M solution) and spermidine free base (20 µL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 µL of absolute ethanol, centrifuged again and the supernatant removed. The ethanol rinse is performed again and the particles resuspended in a final volume of 30 uL of ethanol. An aliquot (5 µL) of the DNA-coated gold particles can be placed in the center of a flying disc (Bio-Rad Labs, 861 Ridgeview Dr, Medina, Ohio). The particles are then accelerated into the corn tissue with a PDS-1000/He (Bio-Rad Labs, 861 Ridgeview Dr, Medina, Ohio), using a helium pressure of 1000 psi, a gap distance of 0.5 cm and a flying distance of 1.0 cm. For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi. Seven days after bombardment the tissue can be transferred to N6 medium that contains gluphosinate (2 mg per liter) and lacks casein or proline. The tissue continues to grow slowly on this medium. After an additional 2 weeks the tissue can be transferred to fresh N6 medium containing gluphosinate. After 6 weeks, areas of about 1 cm in diameter of actively growing callus can be identified on some of the plates containing the glufosinate-supplemented medium. These calli may continue to grow when sub-cultured on the selective medium. Plants can be regenerated from tie transgenic callus by first transferring clusters of tissue to N6 medium supplemented with 0.2 mg per liter of 2,4-D. After two weeks the tissue can be transferred to regeneration medium (Fromm et al., (1990) *Bio/Technology* 8:833–839).

Example 4
Expression of Chimeric Genes in Tobacco Cells (Dicotyledon)

Cloning sites (XbaI or SmaI) can be incorporated into the oligonucleotides to provide proper orientation of the DNA fragment when inserted into the digested vector pBI121 (Clonetech Inc., 6500 Donlon Rd, Somis, Calif.) or other appropriate transformation vector. Amplification could be performed as described above and the amplified DNA would then be digested with restriction enzymes XbaI and SmaI and fractionated on a 0.7% low melting point agarose gel in 40 mM-Tris-acetate, pH 8.5, 1 mM EDTA. The appropriate band can be excised from the gel, melted at 68° C. and combined with a 13 kb XbaI-SmaI fragment of the plasmid pBI121 and handled as in Example 3. The resulting plasmid construct would comprise a chimeric gene encoding, in the 5' to 3' direction, right border region, the nos promoter linked to the NPT II gene and a nos terminator region followed by a cauliflower mosaic virus 35S promoter linked to a cDNA fragment encoding a plant GST enzyme and the nos terminator 3' region flanked by the left border region. The resulting plasmid could be mobilized into the Agrobacterium strain LBA4404/pAL4404 (Hoekema et al. *Nature* 303:179–180, (1983) using triparental matings (Ruvkin and Ausubel, *Nature* 289:85–88, (1981)). The resulting Agrobacterium strains could be then cocultivated with protoplasts (van den Elzen et al. *Plant Mol. Biol,* 5:149–154 (1985)) or leaf disks (Horsch et al. *Science* 227:1229–1231, (1985)) of *Nicotiana tabacum* cv Wisconsin 38 and kanamycin-resistant transformants would be selected. Kanamycin-resistant transformed tobacco plants would be regenerated.

Example 5
Expression of Chimeric Genes in Microbial Cells and Purification of Gene Product Example 5 illustrates the expression of isolated full length genes encoding either class I, II or III GST proteins in *E. coli.*

All clones listed in Table 2 were selected on the basis of homology to known GSTs using the BLAST algorithm as described in Example 2. Plasmid DNA was purified using QIAFilter cartridges (Qiagen. Inc., 9600 De Soto Ave, Chatsworth, Calif.) according to the manufacturer's instructions. Sequence was generated on an ABI Automatic sequencer using dye terminator technology (U.S. Pat. No. 5,366,860; EP 272007) using a combination of vector and insert-specific primers. Sequence editing was performed in either DNAStar (DNA, Star Inc.) or the Wisconsin GCG program (Wisconsin Package Version 9.0, Genetics Computer Group (GCG), Madison, Wis.). All sequences represent coverage at least two times in both directions.

cDNA from the clones bms1.pk0023.g8, cs1.pk0010.c5, ceb1.pk0017.a5, m.15.5.d06.sk20, ceb5.pk0049.a11, ceb5.pk0051.f8, and cs1.pk0059.e2, encoding the instant maize GST enzymes were inserted into the ligation independent cloning (LIC) pET30 vector (Novagen, Inc., 597 Science Dr, Madison, Wis.) under the control of the T7 promoter, according to the manufacturer's instructions (see Novagen publications "LIC Vector Kits", publication number TB163 and U.S. Pat. No. 4,952,496). The vector was then used to transform BL21(DE3) competent *E. coli* hosts. Primers with a specific 3' extension designed for ligation independent cloning were designed to amplify the GST gene Maniatis). Amplification products were gel-purified and annealed into the LIC vector after treatment with T4 DNA polymerase (Novagen). Insert-containing vectors were then used to transform NovaBlue competent *E. coli* cells and transformants were screened for the presence of viable inserts. Clones in the correct orientation with respect to the T7 promoter were transformed into BL21(DE3) competent cells (Novagen) and selected on LB agar plates containing 50 μg/mL kanamycin. Colonies arising from this transformation were grown overnight at 37° C. in Lauria Broth to OD 600=0.6 and induced with 1 mM IPTG and allowed to grow for an additional two hours. The culture was harvested, resuspended in binding buffer, lysed with a French press and cleared by centrifugation.

Expressed protein was purified using the HIS binding kit (Novagen) according to the manufacturer's instructions. Purified protein was examined on 15–20% SDS Phast Gels (Bio-Rad Laboratories, 861 Ridgeview Dr, Medina, Ohio) and quantitated spectrophotometrically using BSA as a standard. Protein data is tabulated below in Table 3.

TABLE 3

| Protein Expression Data | |
|---|---|
| CLONE | OD.280 |
| bms1.pk0023.g8 | 0.57 |
| cs1.pk0010.c5 | 0.53 |
| ceb1.pk0017.a5 | 0.50 |
| m.15.5.d06.sk20 | 0.39 |
| ceb5.pk0049.a11 | 2.06 |
| ceb5.pk0051.f8 | 1.30 |
| cs1.pk0059.e2 | 1.45 |

Example 6
Screening of Expressed GST Enzymes for Substrate Metabolism

The GST enzymes, expressed and purified as described in Example 5 were screened for their ability to metabolize a variety of substrates. Substrates tested included the three herbicide electrophilic substrates chlorimuron ethyl, alachlor, and Atrazine, and four model electrophilic substrates, 1-chloro-2,4-dinitrobenzene (CDNB), ethacrynic acid, t-stilbene oxide, and 1,2-epoxy-3-(p-nitrophenoxy) propane. The enzymes were purified as described in Example 5 and used in the following assay.

For each enzyme, the conjugation reaction with each electrophilic substrate was performed by incubating 0.3 to 30 μg enzyme in 0.1 M MOPS (pH 7.0) containing 0.4 mM of the electrophilic substrate. The reaction was inititated by the addition of glutathione to a final concentration of 4 mM. After 5 to 30 min, the reaction was terminated by the addition of 45 μL acetonitrile, microfuged for 10 min to remove precipitated protein, and then the supernatent was removed and added to 65 μl of water. This sample was chromatographed on a Zorbax C8 reverse phase HPLC column (3 μm particle size, 6.2 mm×8 cm) using a combination of linear gradients (flow=1.5 mL/min) of 1% $H_3PO_4$ in water (solvent A) and 1% $H_3PO_4$ in acetonitrile. The gradient started with 5% solvent B, progressing from 5% to 75% solvent B between 1 and 10 min, and from 75% to 95% solvent B between 10 and 12 min. Control reactions without enzyme were performed to correct for uncatalyzed reaction. Quantitation of metabolites were based on an assumption that the extinction coefficient of the conjugate was identical to that of the electrophilic substrate.

Table 4 shows the activity of each enzyme measured in $nmol.min^{-1}.mg^{-1}$ with the seven different substrates. Activities are related to the activities of the known and previously isolated and purified GST enzymes, BZ-II (Marrs et al., *Nature* 375:397–400 (1995)), pIN2-1 (Hershey et al., *Plant Molecular Biology* 17:679–690, (1991)), GST-I, GST-III, and GST-IV, collectively described in Shah et al., *Plant Mol Biol* 6, 203–211(1986); Jepson et al., *Plant Mol Biol* 26:1855–1866, (1994); Moore et al., *Nucleic Acids Res* 14:7227–7235 (1986); and Holt et al., *Planta* 196:295–302, (1995).

TABLE 4

| GST Name | GST Class | Chlor-Imuron-Ethyl | Alachlor | Atrazine | CDNB | Ethacrynic Acid | t-Stilbene Oxide | 1,2-epoxy-3-(p-nitrophenoxy) propane |
|---|---|---|---|---|---|---|---|---|
| cs1.pk0059.e2 | III | 0.1 | 8 | 0.02 | 1348 | 20 | 1.25 | 43 |
| ceb5.pk0049.a11 | III | 0.4 | 18 | 0.01 | 3939 | 102 | 0.01 | 30 |
| ceb5.pk0051.f8 | III | 1.9 | 27 | 0.08 | 2136 | 117 | 0.02 | 14 |
| BZ-II | lII | 0.2 | 0 | 0.00 | 15 | 23 | 0.05 | 0 |
| ceb1.pk0017.a5 | I | 0.1 | 0 | 0.00 | 15 | 5 | 0.00 | 0 |
| cs1.pk0010.c5 | I | 0.1 | 0 | 0.00 | 30 | 9 | 0.00 | 0 |
| bms1.pk0023.g8 | I | 0.2 | 0 | 0.00 | 15 | 13 | 0.00 | 0 |
| GST-IV | i | 0.3 | 1 | 0.00 | 15 | 13 | 0.00 | 0 |
| GST-I | I | 0.4 | 77 | 0.60 | 46485 | 32 | 0.98 | 92 |
| GST-III | I | 0.3 | 3 | 0.05 | 1803 | 1 | 0.31 | 28 |
| m.15.5.d06.sk20 | II | 0.1 | 0 | 0.00 | 45 | 17 | 0.00 | 1 |
| pIN2-1 | IV | 0 | 0 | — | 15 | — | — | — |

---

What is claimed is:

1. An isolated nucleic acid fragment encoding a GST enzyme selected from the group consisting of:
   (a) an isolated nucleic acid fragment encoding the amino acid sequence selected from the group consisting of SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:72 and SEQ ID NO:74; and
   (b) an isolated nucleic acid fragment that is complementary to (a).

2. The isolated nucleic acid fragment of claim 1 selected from the group consisting of SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71 and SEQ ID NO:73.

3. A chimeric gene comprising the isolated nucleic acid fragment of claim 1 operably linked to suitable regulatory sequences.

4. A transformed host cell comprising the chimeric gene of claim 3.

5. The transformed host cell of claim 4 wherein the host cell is a plant cell.

6. The transformed host cell of claim 4 wherein the host cell is E. coli.

7. A method of altering the level of expression of a GST enzyme in a host cell comprising:
   (a) transforming a host cell with the chimeric gene of claim 3 and;
   (b) growing the transformed host cell produced in step (a) under conditions that are suitable for expression of the chimeric gene resulting in production of altered levels of a GST enzyme in the transformed host cell relative to expression levels of an untransformed host cell.

8. A method of obtaining a nucleic acid fragment encoding all or a substantial portion of the amino acid sequence encoding a GST enzyme comprising:

(a) probing a cDNA or genomic library with a nucleic acid fragment selected from the group consisting of SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEO ID NO:65, SEQ ID NO:67, SEQ ID NO:69, SEQ ID NO:71 and SEQ ID NO:73, under the following hybridization conditions: 0.1×SSC, 0.1% SDS at 65 degrees C.;

(b) identifying a DNA clone that hybridizes with the nucleic acid fragment of step (a); and (c) sequencing the cDNA or genomic fragment that comprises the clone identified in step (b), wherein the sequenced cDNA or genomic fragment encodes all or substantially all of the amino acid sequence encoding a GST enzyme.

* * * * *

SEQUENCE LISTING

<160> NUMBER OF SEQ ID NOS: 74

<210> SEQ ID NO 1
<211> LENGTH: 844
<212> TYPE: DNA
<213> ORGANISM: maize

<400> SEQUENCE: 1

```
cggcacgagc aatggcgccg ccgatgaagg tgtacgggtg ggccgtgtcg ccgtggatgg      60
cgcgcgcgct ggtgtgtctg gaggaggccg gcgccgacta cgagatcgtc cccatgagca     120
ggtgtggcgg cgaccaccgc cggccggagc acctcgccaa aaacccgttc ggtgaaatcc     180
cagttttaga ggacggtgat ctcacgctct accaatcacg cgccatcgca cggtacgtcc     240
tccgcaagct caagccagag ctcctccgcg aaggcgacct cgaggggtcg gcgatggtgg     300
acgcgtggat ggaggtggaa gcccaccaca tggagccggc cctgtggccc atcatccgcc     360
acagcatcat cggccagtac gtcggccgcg agcgcgacca ccaggccgtc atcgacgaga     420
acctcgacag gctgaggaag gtgctgccgg cgtacgaggc gaggctgtcc gtctgcaagt     480
acctggtggg ggacgacatc agcgccgccg acctctgcca cttcggcttc atgcgctact     540
tcatggccac ggagtacgcc ggcttggtgg acgcgtaccc gcacgtcaag gcctggtggg     600
acgcgctgct ggcgaggccc tcggtgcaga aggtcatggc aggcatgccg ccggattttg     660
ggtacgccag cgggaacata ccataggcta gaagcggtgg gcgtccgtca ttctgcagat     720
ctgaggtctc tgaacctcag cgtttccgat aaacatgcat gctttatgta ctgtttaaaa     780
aacaaacctg attggtgcag ggtattttag tcctcttaaa aaaaaaaaaa aaaaaaaaaa     840
aaaa                                                                  844
```

<210> SEQ ID NO 2
<211> LENGTH: 224
<212> TYPE: PRT
<213> ORGANISM: maize

<400> SEQUENCE: 2

```
Met Ala Pro Pro Met Lys Val Tyr Gly Trp Ala Val Ser Pro Trp Met
  1               5                  10                  15

Ala Arg Ala Leu Val Cys Leu Glu Glu Ala Gly Ala Asp Tyr Glu Ile
             20                  25                  30

Val Pro Met Ser Arg Cys Gly Gly Asp His Arg Arg Pro Glu His Leu
```

```
                    35                  40                  45
        Ala Lys Asn Pro Phe Gly Glu Ile Pro Val Leu Glu Asp Gly Asp Leu
                50                  55                  60

Thr Leu Tyr Gln Ser Arg Ala Ile Ala Arg Tyr Val Leu Arg Lys Leu
        65                  70                  75                  80

Lys Pro Glu Leu Leu Arg Glu Gly Asp Leu Glu Gly Ser Ala Met Val
                        85                  90                  95

Asp Ala Trp Met Glu Val Glu Ala His His Met Glu Pro Ala Leu Trp
                        100                 105                 110

Pro Ile Ile Arg His Ser Ile Ile Gly Gln Tyr Val Gly Arg Glu Arg
                        115                 120                 125

Asp His Gln Ala Val Ile Asp Glu Asn Leu Asp Arg Leu Arg Lys Val
                    130                 135                 140

Leu Pro Ala Tyr Glu Ala Arg Leu Ser Val Cys Lys Tyr Leu Val Gly
        145                 150                 155                 160

Asp Asp Ile Ser Ala Ala Asp Leu Cys His Phe Gly Phe Met Arg Tyr
                            165                 170                 175

Phe Met Ala Thr Glu Tyr Ala Gly Leu Val Asp Ala Tyr Pro His Val
                        180                 185                 190

Lys Ala Trp Trp Asp Ala Leu Leu Ala Arg Pro Ser Val Gln Lys Val
                        195                 200                 205

Met Ala Gly Met Pro Pro Asp Phe Gly Tyr Ala Ser Gly Asn Ile Pro
                    210                 215                 220

<210> SEQ ID NO 3
<211> LENGTH: 999
<212> TYPE: DNA
<213> ORGANISM: maize

<400> SEQUENCE: 3
atcaccattc ttcatccctc gttgtcatct cacagcttgg gctagagacc aaacaaacca      60
aagggaagca tggcagcagg cctgcaagtg tttggccagc cggcgtctac tgatgttgcc     120
agggttctga cgtgcctgtt tgagaagaaa ttggagtttg agcttgtccg cattgataca     180
tttaagacac atcacaggct tcctgagttc atcaggctgc gggatccgaa tgggcaagtg     240
accttcaagc atggcgacaa acccttgtt gattcaaggg acatatgccg gtacgtttgc     300
aaccagtttc caaattacgg aaacaagagc ctctatggat ctggtgctct agaacgggca     360
tcgatagaac agtggctcca ggcagaagcc agaactttg ccctcccag ctctgcgctt      420 gtgtttcagc tggcgttcgt tccgcacctc agtcacctgg gcgttcgtca ggaccctgct     480
gttattgctg aaaacgagga caaactgaag caggttcttg atgtttacga cgaaatactc     540
tccaagaacg agtacctggc tggtgatgag ttcaccctgg ccgacctgtc tcaccttccg     600
aactcgcact acatcgtaaa caccgagaga ggaaggaagc tcttcaccaa caagaagaat     660
gtggcgaaat ggtatgacag gctctcgaag cgcgagacat gggtgcaggt cgtcaagatg     720
cagaaggaac atcctggtgc gttcaagtaa tggcttgtct tggggagttg tgagtatggc     780
ttcatcgtcc gtgttggtct ggctcatcag tgttaaaagc ccatcagtgt cgtcaaccag     840
aataatgtga agcccaactg tgatgtatgg tcttttttttt ttaaaagcgc atttgtaaac     900
tattggctat ttcttgcacg tgccaattca tcgtcacata taaataaac tgtatctttg      960 acctttgtgtc atgtacgcaa aaaaaaaaa aaaaaaaa                              999

<210> SEQ ID NO 4
```

<211> LENGTH: 226
<212> TYPE: PRT
<213> ORGANISM: maize

<400> SEQUENCE: 4

```
Met Ala Ala Gly Leu Gln Val Phe Gly Gln Pro Ala Ser Thr Asp Val
 1               5                  10                  15
Ala Arg Val Leu Thr Cys Leu Phe Glu Lys Lys Leu Glu Phe Glu Leu
            20                  25                  30
Val Arg Ile Asp Thr Phe Lys Thr His His Arg Leu Pro Glu Phe Ile
        35                  40                  45
Arg Leu Arg Asp Pro Asn Gly Gln Val Thr Phe Lys His Gly Asp Lys
    50                  55                  60
Thr Leu Val Asp Ser Arg Asp Ile Cys Arg Tyr Val Cys Asn Gln Phe
65                  70                  75                  80
Pro Asn Tyr Gly Asn Lys Ser Leu Tyr Gly Ser Gly Ala Leu Glu Arg
                85                  90                  95
Ala Ser Ile Glu Gln Trp Leu Gln Ala Glu Ala Gln Asn Phe Gly Pro
            100                 105                 110
Pro Ser Ser Ala Leu Val Phe Gln Leu Ala Phe Val Pro His Leu Ser
        115                 120                 125
His Leu Gly Val Arg Gln Asp Pro Ala Val Ile Ala Glu Asn Glu Asp
    130                 135                 140
Lys Leu Lys Gln Val Leu Asp Val Tyr Asp Glu Ile Leu Ser Lys Asn
145                 150                 155                 160
Glu Tyr Leu Ala Gly Asp Glu Phe Thr Leu Ala Asp Leu Ser His Leu
                165                 170                 175
Pro Asn Ser His Tyr Ile Val Asn Thr Glu Arg Gly Arg Lys Leu Phe
            180                 185                 190
Thr Asn Lys Lys Asn Val Ala Lys Trp Tyr Asp Arg Leu Ser Lys Arg
        195                 200                 205
Glu Thr Trp Val Gln Val Val Lys Met Gln Lys Glu His Pro Gly Ala
    210                 215                 220
Phe Lys
225
```

<210> SEQ ID NO 5
<211> LENGTH: 901
<212> TYPE: DNA
<213> ORGANISM: maize

<400> SEQUENCE: 5

```
ccccagcggc ggcgaggcga tggcggcgcc tgtgacggtg tacggaccga tgctctcacc      60
agctgtggcc cgcgtggcgg cctgcctcct ggagaaggac gtgccgttcc agatcgagcc     120
ggtggacatg tccaagggcg agcacaagtc gccgtccttc ctcaagctcc agcccttcgg     180
acaggtccct gccttcaagg accacctcac aaccgtcttt gagtcaaggg ctatttgccg     240
ttacatatgc gaccagtatg cggactctgg taatcaggcc ctcttcggca agaaagaaga     300
cggcgcggtt ggccgcgctg ccattgaaca gtggatagag tctgaaggcc agagctttaa     360
cccaccgagc ttggctatta tcttccagct cgcatttgca ccgatgatgg gccggaccac     420
tgacctggct gtggttgagc araatgaagc gaagcttgcg aaggtgcttg atgtgtatga     480
ccaacggctg ggggagagcc agtattttgc tggtgatgat ttctcccctg ccgaccttg     540
tgcacttgcc caatgcagat tccttgtgaa acagaaccag caaggctggc ttgatcaccg     600
```

```
agagaaagaa tcttgctaga tggtgggatg atgtctcgtc ccgacctgca tggaaaaagg    660
tcactgagat gcagagcacg ccgaggccct cttagagctt ttttttgggt ttctttgagc    720
agcttctgat ggcaattagt tgcattctcc ttgttttgtc atcaagtcct tgtctgtacc    780
gtttcctgtt ctcttattta tcggtcttaa ttcttgatct atgtatggtt tggatctgtt    840
cttctggtcc tttagtttat ataagtacct acaattcttc aaaaaaaaaa aaaaaaaaa     900 a                                                                    901

<210> SEQ ID NO 6
<211> LENGTH: 199
<212> TYPE: PRT
<213> ORGANISM: maize

<400> SEQUENCE: 6

Met Ala Ala Pro Val Thr Val Tyr Gly Pro Met Leu Ser Pro Ala Val
 1               5                  10                  15

Ala Arg Val Ala Ala Cys Leu Leu Glu Lys Asp Val Pro Phe Gln Ile
            20                  25                  30

Glu Pro Val Asp Met Ser Lys Gly Glu His Lys Ser Pro Ser Phe Leu
        35                  40                  45

Lys Leu Gln Pro Phe Gly Gln Val Pro Ala Phe Lys Asp His Leu Thr
    50                  55                  60

Thr Val Phe Glu Ser Arg Ala Ile Cys Arg Tyr Ile Cys Asp Gln Tyr
65                  70                  75                  80

Ala Asp Ser Gly Asn Gln Ala Leu Phe Gly Lys Lys Glu Asp Gly Ala
                85                  90                  95

Val Gly Arg Ala Ala Ile Glu Gln Trp Ile Glu Ser Glu Gly Gln Ser
            100                 105                 110

Phe Asn Pro Pro Ser Leu Ala Ile Ile Phe Gln Leu Ala Phe Ala Pro
        115                 120                 125

Met Met Gly Arg Thr Thr Asp Leu Ala Val Val Glu Gln Asn Glu Ala
    130                 135                 140

Lys Leu Ala Lys Val Leu Asp Val Tyr Asp Gln Arg Leu Gly Glu Ser
145                 150                 155                 160

Gln Tyr Phe Ala Gly Asp Asp Phe Ser Pro Gly Arg Pro Cys Ala Leu
                165                 170                 175

Ala Gln Cys Arg Phe Pro Cys Glu Gln Asn Gln Gln Gly Trp Leu Asp
            180                 185                 190

His Arg Glu Lys Glu Ser Cys
        195

<210> SEQ ID NO 7
<211> LENGTH: 458
<212> TYPE: DNA
<213> ORGANISM: maize

<400> SEQUENCE: 7
gcgcgtcgga ggagctccac ggcgtcaggc ccttcgaccc cgagcggact ccgctgctgg     60
cggcgtggtc ggagcgcttc ggcgcgctgg atgccgtcca cggtgatg cccgacgtcg    120 gcaggctgct cgagttcggc aaggcgttga tggcacgtct gcggctgcg gccgccgccg    180 gtgcaagcaa taactgaaga gggcatggtg tatccgtcat gtgtttcagg ttttcgtata    240
gtgaacaaaa aaggaaaaaa taatgctagc tacgcatcgg aacgcggctt tgtgctttgc    300
cgtctcgccg ttagttcagc ttatgtgatg tgagtgttgc cgtgcatgtg tgtgttactt    360
```

```
cagatgtatc ctgttcggtt cagtgattat atggaacatt ttattttggt tggataaaaa    420
aaaaaaaaaa aaaaaaaaaa aaaaaaaaaa aaaaaaaa                            458

<210> SEQ ID NO 8
<211> LENGTH: 64
<212> TYPE: PRT
<213> ORGANISM: maize

<400> SEQUENCE: 8

Ala Ser Glu Glu Leu His Gly Val Arg Pro Phe Asp Pro Glu Arg Thr
  1               5                  10                  15

Pro Leu Leu Ala Ala Trp Ser Glu Arg Phe Gly Ala Leu Asp Ala Val
             20                  25                  30

Gln Thr Val Met Pro Asp Val Gly Arg Leu Leu Glu Phe Gly Lys Ala
         35                  40                  45

Leu Met Ala Arg Leu Ala Ala Ala Ala Ala Gly Ala Ser Asn Asn
     50                  55                  60

<210> SEQ ID NO 9
<211> LENGTH: 911
<212> TYPE: DNA
<213> ORGANISM: maize

<400> SEQUENCE: 9
gcaaggtcga catgtcgtct ccgccgccgg tgaagctgat cggcttcttc ggcagcccgt     60
acgcgttccg cgcggaggcg cgcgctgtgcc tgaaaggcgt gccgtacgag ctgatcctgg   120
aggacctgtt cggcagcaag agcgagctcc tgctccacca caaccccgtg cacaagaagg   180
tgcccgtgct cctccacggc gacggccggg ccatctccga gtccctcgtc atcgccgagt   240
acgtcgacga ggccttcgac gggccgccgc tgctccccgc cgaccctac gcgcgcgccg   300 ccgcccgctt ctgggccgac ttcatcgaga ccaggctcac caagcccttc ttcatggcga   360
tctgggtgga ggagcgcgac gcgcggctgc ggttcgagga ggaggccaag gagctcgtgg   420
cgctgctgga ggcgcagctc gagggaaaga ggttcttcgc cggcgacagg ccggggtacc   480
tcgacgtggc cgcgtccgcg ctcgggccct ggcgcagcgt catcgaggag ctcaacggtg   540
tggcgctgct cagcgaggat gaccaccca acctgtgccg gtggaccagg gactactgcg   600
ccttcgaggc tctcaagccg tgcatgccgg atcgggagaa gctcctcgcc tacttcacta   660
agaacttcga caggtacaag gcggccgtca atgcgacgct atcgcagtcg cagcagtaat   720
aactgcccaa ctgggtacgc ctctgcccgg ccgtatggcg ggcgtttctt ttttctttc   780 ttcagaataa cgtagctgtg cccagtactc atgttttcaa ttctgcaaag tgcaaaccaa   840
caagtcgctg tgtggtttac tcttttaaa aaaaaaaaa aaaaaaaaa aaaaaaaaa    900 aaaaaaaaaa a                                                          911

<210> SEQ ID NO 10
<211> LENGTH: 235
<212> TYPE: PRT
<213> ORGANISM: maize

<400> SEQUENCE: 10

Met Ser Ser Pro Pro Pro Val Lys Leu Ile Gly Phe Phe Gly Ser Pro
  1               5                  10                  15

Tyr Ala Phe Arg Ala Glu Ala Ala Leu Cys Leu Lys Gly Val Pro Tyr
             20                  25                  30

Glu Leu Ile Leu Glu Asp Leu Phe Gly Ser Lys Ser Glu Leu Leu Leu
```

|     |     |     |     | 35  |     |     |     | 40  |     |     |     | 45  |     |     |
| --- | --- | --- | --- | --- | --- | --- | --- | --- | --- | --- | --- | --- | --- | --- |
| His | His | Asn | Pro | Val | His | Lys | Lys | Val | Pro | Val | Leu | Leu | His | Gly | Asp |
|     |     |     |     | 50  |     |     |     | 55  |     |     |     | 60  |     |     |

Gly Arg Ala Ile Ser Glu Ser Leu Val Ile Ala Glu Tyr Val Asp Glu
65                  70                  75                  80

Ala Phe Asp Gly Pro Leu Leu Pro Ala Asp Pro Tyr Ala Arg Ala
                85                  90                  95

Ala Ala Arg Phe Trp Ala Asp Phe Ile Glu Thr Arg Leu Thr Lys Pro
            100                 105                 110

Phe Phe Met Ala Ile Trp Val Glu Arg Asp Ala Arg Leu Arg Phe
        115                 120                 125

Glu Glu Glu Ala Lys Glu Leu Val Ala Leu Leu Glu Ala Gln Leu Glu
130                 135                 140

Gly Lys Arg Phe Phe Ala Gly Asp Arg Pro Gly Tyr Leu Asp Val Ala
145                 150                 155                 160

Ala Ser Ala Leu Gly Pro Trp Arg Ser Val Ile Glu Glu Leu Asn Gly
                165                 170                 175

Val Ala Leu Leu Ser Glu Asp Asp His Pro Asn Leu Cys Arg Trp Thr
            180                 185                 190

Arg Asp Tyr Cys Ala Phe Glu Ala Leu Lys Pro Cys Met Pro Asp Arg
        195                 200                 205

Glu Lys Leu Leu Ala Tyr Phe Thr Lys Asn Phe Asp Arg Tyr Lys Ala
    210                 215                 220

Ala Val Asn Ala Thr Leu Ser Gln Ser Gln Gln
225                 230                 235

<210> SEQ ID NO 11
<211> LENGTH: 948
<212> TYPE: DNA
<213> ORGANISM: maize

<400> SEQUENCE: 11

```
agcgcatgca ggtagcaatg gcgggggaga cgaagaaggg cctggtgctg ctggacttct     60
gggtgagccc gttcgggcag cgctgccgca tcgcgctggc ggagaagggc atcgcctacg    120
agtactcgga gcaggagctg ctgggcggcg ccaagagcga catcctcctc cgctccaacc    180
cggtgcacaa gaagatcccc gtgctcctcc acgacggccg ccccgtctgc gagtccctcg    240
tcatcctcga gtacctcgag gaggccttcc ggaggcctc ccccaggctg ctccccgacg    300
ccgcctacgc gcgcgcgcag gcccgcttct gggcggccta ctccgacaag gtctacaagg    360
ccggcacgcg gctgtggaag ctcaggggcg acgcgcgggc gcaggcgcgc gccgagatcg    420
tgcaggtggt ccggaacctc gacggcgagc taggggacaa ggccttcttc ggcggcgagg    480
cgttcgggtt cgtggacgtg gcgctcgtgc ccttcgtgcc gtggctcccc agctacgagc    540
ggtacgggga cttcagcgtg gcggagatcg cgcccaggct ggcggcgtgg gcgcgccggt    600
gcgcgcagcg ggagagcgtg gccaggaccc ttcacccgcc ggaaaaggtg gacgagttca    660
tcaacctgct caagaagacc tacggcatcg agtagtagag cggactacta ctagcagagg    720
agatggtacc ggccgtacgt acgtggctgc catgcagttt ttgtttcggt ttgtttaaac    780
gggactccat gaatggatgg aactcttctt gggctccgtg tgctacatac acatctgtaa    840
aggtgaacta aaatcacggt aaaaactcgg aaattagttt gtaaagggtc cagcccccct    900
cctttataaa tagagaggta tacggctgat aaaaaaaaaa aaaaaaa                 948
```

<210> SEQ ID NO 12
<211> LENGTH: 225
<212> TYPE: PRT
<213> ORGANISM: maize

<400> SEQUENCE: 12

```
Met Ala Gly Glu Thr Lys Lys Gly Leu Val Leu Leu Asp Phe Trp Val
 1               5                  10                  15

Ser Pro Phe Gly Gln Arg Cys Arg Ile Ala Leu Ala Glu Lys Gly Ile
                20                  25                  30

Ala Tyr Glu Tyr Ser Glu Gln Glu Leu Leu Gly Ala Lys Ser Asp
         35                  40                  45

Ile Leu Leu Arg Ser Asn Pro Val His Lys Ile Pro Val Leu Leu
    50                  55                  60

His Asp Gly Arg Pro Val Cys Glu Ser Leu Val Ile Leu Glu Tyr Leu
 65                  70                  75                  80

Glu Glu Ala Phe Pro Glu Ala Ser Pro Arg Leu Leu Pro Asp Ala Ala
                85                  90                  95

Tyr Ala Arg Ala Gln Ala Arg Phe Trp Ala Ala Tyr Ser Asp Lys Val
                100                 105                 110

Tyr Lys Ala Gly Thr Arg Leu Trp Lys Leu Arg Gly Asp Ala Arg Ala
            115                 120                 125

Gln Ala Arg Ala Glu Ile Val Gln Val Val Arg Asn Leu Asp Gly Glu
130                 135                 140

Leu Gly Asp Lys Ala Phe Phe Gly Gly Glu Ala Phe Gly Phe Val Asp
145                 150                 155                 160

Val Ala Leu Val Pro Phe Val Pro Trp Leu Pro Ser Tyr Glu Arg Tyr
                165                 170                 175

Gly Asp Phe Ser Val Ala Glu Ile Ala Pro Arg Leu Ala Ala Trp Ala
            180                 185                 190

Arg Arg Cys Ala Gln Arg Glu Ser Val Ala Arg Thr Leu His Pro Pro
        195                 200                 205

Glu Lys Val Asp Glu Phe Ile Asn Leu Leu Lys Lys Thr Tyr Gly Ile
    210                 215                 220

Glu
225
```

<210> SEQ ID NO 13
<211> LENGTH: 840
<212> TYPE: DNA
<213> ORGANISM: maize

<400> SEQUENCE: 13

| | | | | | |
|---|---|---|---|---|---|
| gttggggatg | tgggcgagcc | ctatggtgat | cagggtggag | tgggcgctgc | ggctgaaggg | 60 |
| cgtcgagtac | gagtacgtcg | acgaggacct | cgccaacaag | agcgccgacc | tgctccgcca | 120 |
| caacccggtg | accaagaagg | tgcccgtgct | cgtccacgac | ggcaagccgg | tcgcggagtc | 180 |
| caccatcatc | gtcgagtaca | tcgacgaggt | ctggaagggc | ggctacccca | tcatgccggg | 240 |
| cgaccectac | gagcgtgccc | aggcaaggtt | ctgggccagg | ttcgctgaag | acaagtgcaa | 300 |
| cgctgctctg | tacccgatct | tcaccgcgac | cggcgaggcg | cagcgcaagg | cggtgcacga | 360 |
| ggcccagcag | tgcctcaaga | ccctggagac | ggccttggac | gggaagaagt | tcttcggcgg | 420 |
| ggacgccgtg | ggctacctcg | acatcgtcgt | cgggtggttc | gcgcactggc | tccccgtcat | 480 |
| cgaggaggtg | accggcgcca | gcgtcgtcac | cgacgaggag | ctgccgctga | tgaaggcctg | 540 |
| gttcggccgg | ttcctcgccg | ttgacgtggt | gaaggcggcc | ctgcccgaca | gggacaggct | 600 |

-continued

```
cctcgccgcc aacaaggccc gccgtgagca gctcctctcc gcgtagatgg ctagtaattc    660
tggagcagct agtttcaccg ccgacgctca tatattgctg aataaggact ggttgcactt    720
ttgcacgttg tgcagtgcag ccgaggtttg gatgacctct gccctctgt tccatttcag     780 aatggtagtc ccataataat gcatatacat catgcataaa aaaaaaaaaa aaaaaaaaa     840
```

<210> SEQ ID NO 14
<211> LENGTH: 212
<212> TYPE: PRT
<213> ORGANISM: maize

<400> SEQUENCE: 14

```
Met Trp Ala Ser Pro Met Val Ile Arg Val Glu Trp Ala Leu Arg Leu
 1               5                  10                  15

Lys Gly Val Glu Tyr Glu Tyr Val Asp Glu Asp Leu Ala Asn Lys Ser
            20                  25                  30

Ala Asp Leu Leu Arg His Asn Pro Val Thr Lys Val Pro Val Leu
        35                  40                  45

Val His Asp Gly Lys Pro Val Ala Glu Ser Thr Ile Ile Val Glu Tyr
    50                  55                  60

Ile Asp Glu Val Trp Lys Gly Gly Tyr Pro Ile Met Pro Gly Asp Pro
65                  70                  75                  80

Tyr Glu Arg Ala Gln Ala Arg Phe Trp Ala Arg Phe Ala Glu Asp Lys
                85                  90                  95

Cys Asn Ala Ala Leu Tyr Pro Ile Phe Thr Ala Thr Gly Glu Ala Gln
           100                 105                 110

Arg Lys Ala Val His Glu Ala Gln Gln Cys Leu Lys Thr Leu Glu Thr
       115                 120                 125

Ala Leu Asp Gly Lys Lys Phe Phe Gly Gly Asp Ala Val Gly Tyr Leu
    130                 135                 140

Asp Ile Val Val Gly Trp Phe Ala His Trp Leu Pro Val Ile Glu Glu
145                 150                 155                 160

Val Thr Gly Ala Ser Val Val Thr Asp Glu Glu Leu Pro Leu Met Lys
                165                 170                 175

Ala Trp Phe Gly Arg Phe Leu Ala Val Asp Val Val Lys Ala Ala Leu
           180                 185                 190

Pro Asp Arg Asp Arg Leu Leu Ala Ala Asn Lys Ala Arg Arg Glu Gln
       195                 200                 205

Leu Leu Ser Ala
    210
```

<210> SEQ ID NO 15
<211> LENGTH: 861
<212> TYPE: DNA
<213> ORGANISM: maize

<400> SEQUENCE: 15

```
cggaggcgca gagcttcgac gcgcccagcg ccgagatggt ctacagcctc gccttcctgc    60
cgcccaccct gcccaagcag aacgacaacg caacggcgg cgcgttcaac gccagggacg    120
ccaccgtagg cagcaacgcc gacgcgtcca gcggcaagcg cggtgtggcc gggtcacagc    180
cggcggcgag ccagaccaag gtgagcgcgc agaaggagga ggagatgctg aagctgttcg    240
agcagaggaa gaaggacctg gagaagctgc tggacatcta cgagcagcgc ctggaggag    300 ccacgttcct ggccggcgac aacttcacca tcgccgacct gtcgcacctg ccctacgcgg    360
```

-continued

```
accacctcgt ctccgacccg cgctcccgcc gcatgttcga gtcccgcaag aacgtcagca      420
ggtggtggca cgacgtctcc ggccgcgaca cctggaagta cgtcaagacc ctgcagcgcc      480
cgccgtccac gtccaccgac gccagcgcca agaacggcca gctgggccag cagcagcacc      540
tgccgtcgtc caccgacggc cacggcgtga agacccaacg gctggtccag aacgagcggc      600
acttctagct gttgccgtcc cttcccgccg acgaataaac tacctgcgcc gccgccaccg      660
ccgccatcca tcaacatggt tccttgtgct gttcgtgtcg ttttcatacg tcatacgtgt      720
cttgctgctt tgaagctcc gttcccgggt gcagggacct acgagtccat tccgtcgttt       780
gctgattctg ttcgtcgtgt aataaaatga aaccccacc ccgttttgaa tgaaaaaaaa       840
aaaaaaaaaa aaaaaaaaaa a                                                861
```

<210> SEQ ID NO 16
<211> LENGTH: 190
<212> TYPE: PRT
<213> ORGANISM: maize

<400> SEQUENCE: 16

```
Met Val Tyr Ser Leu Ala Phe Leu Pro Pro Thr Leu Pro Lys Gln Asn
 1               5                  10                  15

Asp Asn Gly Asn Gly Gly Ala Phe Asn Ala Arg Asp Ala Thr Val Gly
            20                  25                  30

Ser Asn Ala Asp Ala Ser Ser Gly Lys Arg Gly Val Ala Gly Ser Gln
        35                  40                  45

Pro Ala Ala Ser Gln Thr Lys Val Ser Ala Gln Lys Glu Glu Glu Met
    50                  55                  60

Leu Lys Leu Phe Glu Gln Arg Lys Lys Asp Leu Glu Lys Leu Leu Asp
65                  70                  75                  80

Ile Tyr Glu Gln Arg Leu Glu Glu Ala Thr Phe Leu Ala Gly Asp Asn
                85                  90                  95

Phe Thr Ile Ala Asp Leu Ser His Leu Pro Tyr Ala Asp His Leu Val
           100                 105                 110

Ser Asp Pro Arg Ser Arg Arg Met Phe Glu Ser Arg Lys Asn Val Ser
       115                 120                 125

Arg Trp Trp His Asp Val Ser Gly Arg Asp Thr Trp Lys Tyr Val Lys
   130                 135                 140

Thr Leu Gln Arg Pro Pro Ser Thr Ser Thr Asp Ala Ser Ala Lys Asn
145                 150                 155                 160

Gly Gln Leu Gly Gln Gln His Leu Pro Ser Ser Thr Asp Gly His
                165                 170                 175

Gly Val Lys Thr Gln Arg Leu Val Gln Asn Glu Arg His Phe
            180                 185                 190
```

<210> SEQ ID NO 17
<211> LENGTH: 917
<212> TYPE: DNA
<213> ORGANISM: maize

<400> SEQUENCE: 17

```
atggcggagg tggaggcgac ggtggggcga ctgatgctgt actcgtactg gcgcagctcg       60
tgctcccacc gtgcccgcat cgctctcaat ctcaaggtg tggattacga gtacaaggcg       120 gtgaacttc tcaagggcga gcagtctgat ccagaattcg tcaagcttaa tcctatgaag      180
ttcgtccctg cgttggttga tggcagttct gtaataggtg actcttacgc gataacactg      240
tatttggagg acaagtaccc agagcctcct cttctacctc aagaccttca aaagaaagct      300
```

```
ttgaatcacc agattgcaag cattgtagct tctggtattc aacctctcca taacctcaca    360
gtgttgaggt tcattgacca gaaggttggt gcaggggaga gtgtgttgtg gactcaacaa    420
caaatcgaga gaggtttcac agctattgag aacctgatac aactaaaagg atgcgccggg    480
aagtatgcaa caggagatga agtccaactg gcagatgtat tccttgcacc ccagatctat    540
gcagccattg aacgcactaa aattgacatg tcaaactacc tcactcttgc taggctccac    600
tcggagtaca tgtcacaccc tgcgtttgaa gcagcgctcc ctggcaagca accggacgcc    660
ccttcatcct cctaggaact gcaccctagt gtgttgttcc tctgaatata tatatatata    720
tatgtatact tctgtaagaa ttaataatta cagagtttcg tctgctatgt cgaaaaatgt    780
caaaagtttt tgtgatttca gagactagcg gcatgaagcg tcgttgtgga tctggccgtc    840
gtcctcatgt ggcatctgtg atttcagggc atgcacttcg tcttagaagg gaaaaaaaaa    900
aaaaaaaaaa aaaaaaa                                                    917
```

<210> SEQ ID NO 18
<211> LENGTH: 224
<212> TYPE: PRT
<213> ORGANISM: maize

<400> SEQUENCE: 18

```
Met Ala Glu Val Glu Ala Thr Val Gly Arg Leu Met Leu Tyr Ser Tyr
  1               5                  10                  15

Trp Arg Ser Ser Cys Ser His Arg Ala Arg Ile Ala Leu Asn Leu Lys
                 20                  25                  30

Gly Val Asp Tyr Glu Tyr Lys Ala Val Asn Leu Leu Lys Gly Glu Gln
             35                  40                  45

Ser Asp Pro Glu Phe Val Lys Leu Asn Pro Met Lys Phe Val Pro Ala
         50                  55                  60

Leu Val Asp Gly Ser Ser Val Ile Gly Asp Ser Tyr Ala Ile Thr Leu
 65                  70                  75                  80

Tyr Leu Glu Asp Lys Tyr Pro Glu Pro Pro Leu Leu Pro Gln Asp Leu
                 85                  90                  95

Gln Lys Lys Ala Leu Asn His Gln Ile Ala Ser Ile Val Ala Ser Gly
            100                 105                 110

Ile Gln Pro Leu His Asn Leu Thr Val Leu Arg Phe Ile Asp Gln Lys
        115                 120                 125

Val Gly Ala Gly Glu Ser Val Leu Trp Thr Gln Gln Ile Glu Arg
    130                 135                 140

Gly Phe Thr Ala Ile Glu Asn Leu Ile Gln Leu Lys Gly Cys Ala Gly
145                 150                 155                 160

Lys Tyr Ala Thr Gly Asp Glu Val Gln Leu Ala Asp Val Phe Leu Ala
                165                 170                 175

Pro Gln Ile Tyr Ala Ala Ile Glu Arg Thr Lys Ile Asp Met Ser Asn
            180                 185                 190

Tyr Leu Thr Leu Ala Arg Leu His Ser Glu Tyr Met Ser His Pro Ala
        195                 200                 205

Phe Glu Ala Ala Leu Pro Gly Lys Gln Pro Asp Ala Pro Ser Ser Ser
    210                 215                 220
```

<210> SEQ ID NO 19
<211> LENGTH: 919
<212> TYPE: DNA
<213> ORGANISM: maize

-continued

```
<400> SEQUENCE: 19
cacctgctgt atctcattac catctgcatc tggttgcccg ttgattgaga aggaggagct      60
gagggccatg gcgaccgaga agcccatcct gtacaacgcc tggatcagct cctgctccca    120
ccgtgttcgc atcgcactca acctcaaagg tgtggattac gagtacaagt cggtaaaccc    180
taggacagat ccagattatg aaaaaatcaa tccaatcaaa tatattccag cattagtaga    240
tggggacata gtcgtttctg attctcttgc catctcattg tatttggaag ataagtatcc    300
tgagcatcca ctcctgccta agatctcaa gaggaaagct cttaatcttc agattgcaaa    360
cattgtttgt tcaagcattc aacctcttca aggctatgct gttattggtc tgcacgaggg    420
taggatgagc ccagatgagg gccttcatat tgttcaaagt tatattgaca agggattcag    480
agcgatcgaa aagctgttgg aaggatgtga gagtaaatat gctactggag atgatgtcca    540
attggcagat gtgttccttg aaccacagat acatgccggc ataaatcgct tccaaatcga    600
tatgtcgatg tacccaatct tggagaggct ccatgatgca tacatgcaaa ttcccgcatt    660
ccaagccgcg cttcctaaaa atcaaccaga cgcaccttca tcataatcat caagattatc    720
tcaataattt gcatgtcatt ttgtaataat ttggataggg agccactgct tcctccatcc    780
cgttgtggat caaagggtg aacgattggc acttacctgc atggtccaat acctattata    840
tttcttaaac agatactatt tacggctatt gtaatttaag cccaaaaaaa aaaaaaaaaa    900
aaaaaaaaaa aaaaaaaa                                                 919

<210> SEQ ID NO 20
<211> LENGTH: 212
<212> TYPE: PRT
<213> ORGANISM: maize

<400> SEQUENCE: 20

Met Ala Thr Glu Lys Pro Ile Leu Tyr Asn Ala Trp Ile Ser Ser Cys
  1               5                  10                  15

Ser His Arg Val Arg Ile Ala Leu Asn Leu Lys Gly Val Asp Tyr Glu
                 20                  25                  30

Tyr Lys Ser Val Asn Pro Arg Thr Asp Pro Asp Tyr Glu Lys Ile Asn
             35                  40                  45

Pro Ile Lys Tyr Ile Pro Ala Leu Val Asp Gly Asp Ile Val Val Ser
         50                  55                  60

Asp Ser Leu Ala Ile Ser Leu Tyr Leu Glu Asp Lys Tyr Pro Glu His
 65                  70                  75                  80

Pro Leu Leu Pro Lys Asp Leu Lys Arg Lys Ala Leu Asn Leu Gln Ile
                 85                  90                  95

Ala Asn Ile Val Cys Ser Ser Ile Gln Pro Leu Gln Gly Tyr Ala Val
                100                 105                 110

Ile Gly Leu His Glu Gly Arg Met Ser Pro Asp Glu Gly Leu His Ile
            115                 120                 125

Val Gln Ser Tyr Ile Asp Lys Gly Phe Arg Ala Ile Glu Lys Leu Leu
        130                 135                 140

Glu Gly Cys Glu Ser Lys Tyr Ala Thr Gly Asp Asp Val Gln Leu Ala
145                 150                 155                 160

Asp Val Phe Leu Glu Pro Gln Ile His Ala Gly Ile Asn Arg Phe Gln
                165                 170                 175

Ile Asp Met Ser Met Tyr Pro Ile Leu Glu Arg Leu His Asp Ala Tyr
            180                 185                 190

Met Gln Ile Pro Ala Phe Gln Ala Ala Leu Pro Lys Asn Gln Pro Asp
```

```
            195                 200                 205

Ala Pro Ser Ser
    210

<210> SEQ ID NO 21
<211> LENGTH: 996
<212> TYPE: DNA
<213> ORGANISM: maize

<400> SEQUENCE: 21
catcgatccg ccattgctca ccgcacaagt gcacgctcac ctcacacacg cagctaagta      60
gctaacgccg taggcgagaa caagaaaagg ctcgacatgg ccgaggagaa gaagcagggc     120
ctgcagctgc tggacttctg ggtgagccca ttcgggcagc gctgccgcat cgcgctggac     180
gagaagggcc tggcctacga gtacctggag caggacctga ggaacaagag cgagctgctc     240
ctccgcgcca acccggtgca caagaagatc cccgtgctgc tgcacgacgg ccgccccgtc     300
tgcgagtccc tcgtcatcgt gcagtacctc gacgaggcgt tcccggaggc ggcgccggcg     360
ctgctccccg ccgacccta cgcgcgcgcg caggcccgct tctgggcgga ctacgtcgac     420
aagaagctgt acgactgcgg cacccggctg tggaagctca aggggacgg ccaggcgcag     480 gcgcgcgcca agatggtcga gatcctccgc acgctggagg gcgcgctcgg cgacgggccc     540
ttcttcggtg gcgacgccct cggcttcgtc gacgtcgcgc tcgtgcccttt cacgtcctgg     600 ttcctcgcct acgaccgctt cggcggcgtc agcgtggaga aggagtgccc gaggctggcc     660
gcctgggcca agcgctgcgc cgagcgcccc agcgtcgcca agaacctcta cccgcccgag     720
aaggtctacg acttcgtctg cgggatgaag aagaggctgg gcatcgagta gagcatccat     780
cggtcggccg gtggctggcc gggagtaata atgacgaacc aataatctag ttttggtttt     840
agtgtgctca gcagagcagt tcgtgttcat gagttcgtcg tcgttgtatt ttctattgtc     900
agcggtggca gcgccgtacg tgttgcctcg tacaccacaa ccgaataaat ggttatgaat     960
ttcttcttgt tgtcttaaaa aaaaaaaaaa aaaaaa                              996

<210> SEQ ID NO 22
<211> LENGTH: 224
<212> TYPE: PRT
<213> ORGANISM: maize

<400> SEQUENCE: 22

Met Ala Glu Glu Lys Lys Gln Gly Leu Gln Leu Leu Asp Phe Trp Val
  1               5                  10                  15

Ser Pro Phe Gly Gln Arg Cys Arg Ile Ala Leu Asp Glu Lys Gly Leu
                 20                  25                  30

Ala Tyr Glu Tyr Leu Glu Gln Asp Leu Arg Asn Lys Ser Glu Leu Leu
             35                  40                  45

Leu Arg Ala Asn Pro Val His Lys Lys Ile Pro Val Leu Leu His Asp
         50                  55                  60

Gly Arg Pro Val Cys Glu Ser Leu Val Ile Val Gln Tyr Leu Asp Glu
 65                  70                  75                  80

Ala Phe Pro Glu Ala Ala Pro Ala Leu Leu Pro Ala Asp Pro Tyr Ala
                 85                  90                  95

Arg Ala Gln Ala Arg Phe Trp Ala Asp Tyr Val Asp Lys Lys Leu Tyr
            100                 105                 110

Asp Cys Gly Thr Arg Leu Trp Lys Leu Lys Gly Asp Gly Gln Ala Gln
        115                 120                 125
```

```
Ala Arg Ala Glu Met Val Glu Ile Leu Arg Thr Leu Glu Gly Ala Leu
        130                 135                 140

Gly Asp Gly Pro Phe Phe Gly Asp Ala Leu Gly Phe Val Asp Val
145                 150                 155                 160

Ala Leu Val Pro Phe Thr Ser Trp Phe Leu Ala Tyr Asp Arg Phe Gly
                165                 170                 175

Gly Val Ser Val Glu Lys Glu Cys Pro Arg Leu Ala Ala Trp Ala Lys
            180                 185                 190

Arg Cys Ala Glu Arg Pro Ser Val Ala Lys Asn Leu Tyr Pro Pro Glu
        195                 200                 205

Lys Val Tyr Asp Phe Val Cys Gly Met Lys Lys Arg Leu Gly Ile Glu
    210                 215                 220
```

<210> SEQ ID NO 23
<211> LENGTH: 895
<212> TYPE: DNA
<213> ORGANISM: maize

<400> SEQUENCE: 23

```
ggcacgagac gacatcgaag gagcctgcga agcgagcgag agtctataat ggcggacgga     60
ggcgagctgc agctgctggg ctcatggtac agcccctacg tgatccgcgc caaggtggcg    120
ctggggctga aggggctcag ctacgagttc gtcgaggagg acctctcccg caagagcgac    180
ctgctgctga agctcaaccc ggtgcacagg aaggtgcccg tgctggtcca cggcggccgc    240
cccgtgtgcg agtcgctcgt catcctgcag tacgtcgacg agacctgggc aggcaccggg    300
accccctctc ccccgccga cgcctacgac cgcgccatgg ctcgcttctg ggcagcctac    360
gtcgacgaca agttctacaa ggagtggaac cggctgttct ggtcgacgac ggcggagaag    420
gcggcggagg cgctcggcgt cgtcgtcccc gtggtggaga cgctggagca ggcgttcagg    480
gagtgctcca agggaaaacc ttcttcggcg gcgacgccgt cgggctcgtg gacatcgcgc    540
tcgggagctt cgtggtgtgg atcagggtgg tggacgaggc ggccggcgta aagcttctgg    600
acgaggccaa gttcccggcc ttgacggcgt gggcggagcg cttcttggcg gtggacgccg    660
tgaaggaggt gatgccggac gccggaaggc tgttggagca ctacaagggg tttctggcta    720
aacggtctcc acctgctggt tactgaacgc tgtaactgta agcctgtaac agcaagctca    780
gtgttcgtgt acttttccgt gcgttaacgt gtactagagt tcaggaaagg ctttgattct    840
gtccagagtc cagacgaata aacgaatgtt ttttataaaa aaaaaaaaaa aaaaa         895
```

<210> SEQ ID NO 24
<211> LENGTH: 180
<212> TYPE: PRT
<213> ORGANISM: maize

<400> SEQUENCE: 24

```
Met Ala Asp Gly Gly Glu Leu Gln Leu Leu Gly Ser Trp Tyr Ser Pro
1               5                   10                  15

Tyr Val Ile Arg Ala Lys Val Ala Leu Gly Leu Lys Gly Leu Ser Tyr
            20                  25                  30

Glu Phe Val Glu Glu Asp Leu Ser Arg Lys Ser Asp Leu Leu Leu Lys
        35                  40                  45

Leu Asn Pro Val His Arg Lys Val Pro Val Leu Val His Gly Gly Arg
    50                  55                  60

Pro Val Cys Glu Ser Leu Val Ile Leu Gln Tyr Val Asp Glu Thr Trp
65                  70                  75                  80
```

```
Ala Gly Thr Gly Thr Pro Leu Leu Pro Ala Asp Ala Tyr Asp Arg Ala
            85                  90                  95

Met Ala Arg Phe Trp Ala Ala Tyr Val Asp Asp Lys Phe Tyr Lys Glu
            100                 105                 110

Trp Asn Arg Leu Phe Trp Ser Thr Thr Ala Glu Lys Ala Ala Glu Ala
            115                 120                 125

Leu Gly Val Val Val Pro Val Val Glu Thr Leu Glu Gln Ala Phe Arg
        130                 135                 140

Glu Cys Ser Lys Gly Lys Pro Ser Ser Ala Ala Thr Pro Ser Gly Ser
145                 150                 155                 160

Trp Thr Ser Arg Ser Gly Ala Ser Trp Cys Gly Ser Gly Trp Trp Thr
                165                 170                 175

Arg Arg Pro Ala
            180

<210> SEQ ID NO 25
<211> LENGTH: 1279
<212> TYPE: DNA
<213> ORGANISM: maize

<400> SEQUENCE: 25
ctgcaggttc agttcagtag tgtgctctga cagtgagatg gcgagcgtga aggttttcgg        60
gtcacccacc tcggcggagg tcgcccgcgt gctcatgtgc ctcttcgaga aggaggtgga      120
gttccagctg atccgcgtcg acgcctaccg gggcaccaag cgcatgcccc agtacctcaa      180
gctgcagccg caaggcgagg cgctcacctt cgaggacgag agcctcaccc tctccgactc      240 caggggatc ctccgccaca tctcccacaa gtacgcgaag cagggcaacc cgttacctga      300
ttggcacggg cgcgctggag cgggcgtcca tcgagcagtg gctgcagacg gaggcgcaga      360
gcttcgacgc gcccagcgcc gagatggtct acagcctcgc cttcctgccg cccaccctgc      420
ccaagcagaa cgacaacggc aacggcggcg cgttcaacgc cagggacgcc accgtaggca      480
gcaacgccga cgcgtccagc ggcaagcgcg cgtgtggccgg tcacagccg gcggcgagcc      540 agaccaaggt gagcgcgcag aaggaggagg agatgctgaa gctgttcgag cagaggaaga      600
aggacctgga gaagctgctg gacatctacg agcagcgcct ggaggaggcc acgttcctgg      660
ccggcgacaa cttcaccatc gccgacctgt cgcacctgcc ctacgcggac cacctcgtct      720
ccgacccgcg ctcccgccgc atgttcgagt cccgcaagaa cgtcagcagg tggtggcacg      780
acgtctccgg ccgcgacacc tggaagtacg tcaagaccct gcagcgcccg ccgtccacgt      840
ccaccgacgc cagcgccaag aacgccagc tgggccagca gcagcacctg ccgtcgtcca      900
ccgacggcca cggcgtgaag acccaacggc tggtccagaa cgagcggcac ttctagctgt      960
tgccgtccct tcccgccgac gaataaacta cctgcgccgc cgccaccgcc gccatccatc     1020
aacatggttc cttgtgctgt tcgtgtcgtt ttcatacgtc atacgtgtct tgctgctttt     1080
gaagctccgt tcccgggtgc agggacctac gagtccattc cgtcgtttgc tgattctgtt     1140
cgtcgtgtaa taaatgaaa accccacccc gttttgaatg aaattcaatt ctcagtgtcg     1200
tgtgaaaaaa aaaaaaaaaa aaaaaaaaaa aaaaaaaaaa aaaaaaaaaa aaaaaaaaaa     1260
aaaaaaaaaa aaaaaaaaa                                                   1279

<210> SEQ ID NO 26
<211> LENGTH: 370
<212> TYPE: PRT
<213> ORGANISM: maize
```

```
<400> SEQUENCE: 26

Met Ala Ser Val Lys Val Phe Gly Ser Pro Thr Ser Ala Glu Val Ala
 1               5                  10                  15

Arg Val Leu Met Cys Leu Phe Glu Lys Glu Val Glu Phe Gln Leu Ile
                20                  25                  30

Arg Val Asp Ala Tyr Arg Gly Thr Lys Arg Met Pro Gln Tyr Leu Lys
            35                  40                  45

Leu Gln Pro Gln Gly Glu Ala Leu Thr Phe Glu Asp Glu Ser Leu Thr
        50                  55                  60

Leu Ser Asp Ser Arg Gly Ile Leu Arg His Ile Ser His Lys Tyr Ala
 65                  70                  75                  80

Lys Gln Gly Asn Pro Leu Pro Asp Trp His Gly Arg Ala Gly Ala Gly
                85                  90                  95

Val His Arg Ala Val Ala Ala Asp Gly Gly Ala Glu Leu Arg Arg Ala
            100                 105                 110

Gln Arg Arg Asp Gly Leu Gln Pro Arg Leu Pro Ala Ala His Pro Ala
        115                 120                 125

Gln Ala Glu Arg Gln Arg Gln Arg Arg Val Gln Arg Gln Gly Arg
130                 135                 140

His Arg Arg Gln Gln Arg Arg Val Gln Arg Gln Ala Arg Cys Gly
145                 150                 155                 160

Arg Val Thr Ala Gly Gly Glu Pro Asp Gln Gly Glu Arg Ala Glu Gly
                165                 170                 175

Gly Gly Asp Ala Glu Ala Val Arg Ala Glu Glu Gly Pro Gly Glu
            180                 185                 190

Ala Ala Gly His Leu Arg Ala Ala Pro Gly Gly His Val Pro Gly
        195                 200                 205

Arg Arg Gln Leu His His Arg Arg Pro Val Ala Pro Ala Leu Arg Gly
                210                 215                 220

Pro Pro Arg Leu Arg Pro Ala Leu Pro Pro His Val Arg Val Pro Gln
225                 230                 235                 240

Glu Arg Gln Gln Val Val Ala Arg Arg Leu Arg Pro Arg His Leu Glu
                245                 250                 255

Val Arg Gln Asp Pro Ala Ala Pro Ala Val His Val His Arg Arg Gln
            260                 265                 270

Arg Gln Glu Arg Pro Ala Gly Pro Ala Ala Pro Ala Val Val His
        275                 280                 285

Arg Arg Pro Arg Arg Glu Asp Pro Thr Ala Gly Pro Glu Arg Ala Ala
290                 295                 300

Leu Leu Ala Val Ala Val Pro Ser Arg Arg Ile Asn Tyr Leu Arg
305                 310                 315                 320

Arg Arg His Arg Arg His Pro Ser Thr Trp Phe Leu Val Leu Phe Val
                325                 330                 335

Ser Phe Ser Tyr Val Ile Arg Val Leu Leu Leu Lys Leu Arg Ser
            340                 345                 350

Arg Val Gln Gly Pro Thr Ser Pro Phe Arg Arg Leu Leu Ile Leu Phe
        355                 360                 365

Val Val
370

<210> SEQ ID NO 27
<211> LENGTH: 1198
<212> TYPE: DNA
<213> ORGANISM: maize
```

-continued

<400> SEQUENCE: 27

```
ctggctcacc tcacctgcag caggcctcgt ctcggtcatc cagcgcattg ctctcaatcg     60
ctgcagcgca tccagtccaa acacacaccg gtcgaatcga gcaatggccg cggggctgca    120
ggtgttcgga cagccggctt ccaccgacgt cgccagggtg ctgacctgcc tcttcgagaa    180
gaacctcgag ttcgagctcg tccgcaccga caccttcaag aagtcgcaca agctccccga    240
gttcatcaag ctgagggatc ctaccgggca ggtgactttc aagcacggtg acaagacaat    300
cgttgattcc aggactatct gccggtacct gtgcacgcag ttcccggacg acgggtacaa    360
gaagctgtac ggcacggggt cgctggagcg ggcgtccata gagcagtggc tgcaggcgga    420
ggcgcagagc ttcgacgcgc cgagctcgga gctggcgttc cagctggcgt cgcgccgca    480
cctcaaggac gtgcggcccg acgaggcccg cgtcgcggag aacgagaaga agctgcacag    540
catgctgggc gtctacgacg acatcctctc caagaacgag tacctcgccg gcgacgactt    600
cacactggcc gacctctccc acctgccaaa ctcccactac atcgtcaact cctccgacag    660
gggcaggaag ctcttcaccg ccaggaagca cgtggccagg tggtacgaca agatctccac    720
ccgcgactcc tggaggcagg tcatgaagat gcagagggag caccccggcg cgttcgagtg    780
atgcgtcgtg cttccttctc tctgcatgca tgcgcgcgtc gcggcgtgtt cctcgtcgtc    840
gccggcttcg tggtcgtcag gcttcacacc gtggtgtgtg gttgtcgagt tcgtcgtatt    900
tcgtatcgta tcgtatcgta tcgtacgtac gtcctgtggg ctaaaataac gtggagcctg    960
cgcctgccta cggtgtctct cgtgtcttcc tttcgctgca tatataagca gtgtcttttt   1020
ctgggtattg tatggtgacc taatcatcaa ctccttttgc aatattggcc aattcaataa   1080
aaatatgtcc gggcattttg ctcgttcgca ctaaaaaaaa aaaaaaaaa aaaaaaaaa   1140
aaaaaaaaaa aaaaaaaaaa aaaaaaaaaa aaaaaaaaaa aaaaaaaaaa aaaaaaa     1198
```

<210> SEQ ID NO 28
<211> LENGTH: 225
<212> TYPE: PRT
<213> ORGANISM: maize

<400> SEQUENCE: 28

```
Met Ala Ala Gly Leu Gln Val Phe Gly Gln Pro Ala Ser Thr Asp Val
  1               5                  10                  15

Ala Arg Val Leu Thr Cys Leu Phe Glu Lys Asn Leu Glu Phe Glu Leu
             20                  25                  30

Val Arg Thr Asp Thr Phe Lys Lys Ser His Lys Leu Pro Glu Phe Ile
         35                  40                  45

Lys Leu Arg Asp Pro Thr Gly Gln Val Thr Phe Lys His Gly Asp Lys
     50                  55                  60

Thr Ile Val Asp Ser Arg Thr Ile Cys Arg Tyr Leu Cys Thr Gln Phe
 65                  70                  75                  80

Pro Asp Asp Gly Tyr Lys Lys Leu Tyr Gly Thr Gly Ser Leu Glu Arg
                 85                  90                  95

Ala Ser Ile Glu Gln Trp Leu Gln Ala Glu Ala Gln Ser Phe Asp Ala
            100                 105                 110

Pro Ser Ser Glu Leu Ala Phe Gln Leu Ala Phe Ala Pro His Leu Lys
        115                 120                 125

Asp Val Arg Pro Asp Glu Ala Arg Val Ala Glu Asn Glu Lys Lys Leu
    130                 135                 140

His Ser Met Leu Gly Val Tyr Asp Asp Ile Leu Ser Lys Asn Glu Tyr
```

```
145                 150                 155                 160
Leu Ala Gly Asp Asp Phe Thr Leu Ala Asp Leu Ser His Leu Pro Asn
                165                 170                 175

Ser His Tyr Ile Val Asn Ser Ser Asp Arg Gly Arg Lys Leu Phe Thr
                180                 185                 190

Ala Arg Lys His Val Ala Arg Trp Tyr Asp Lys Ile Ser Thr Arg Asp
            195                 200                 205

Ser Trp Arg Gln Val Met Lys Met Gln Arg Glu His Pro Gly Ala Phe
        210                 215                 220

Glu
225

<210> SEQ ID NO 29
<211> LENGTH: 1134
<212> TYPE: DNA
<213> ORGANISM: maize

<400> SEQUENCE: 29
tcatcatcca ggcgccgcag tgtaggtcta gatcatccaa tccaacacac cggtcgagca      60
atggcggcag gactgcaggt gttcggacag ccggcgtcca ccgacgtcgc gagggtgctg     120
acctgcctct tcgagaagaa cctcgagttc gagctcatcc gcaccgacac cttcaagaag     180
tcccacaagc tccccgagtt catcaagcta agggatccta ctgggcaggt gactttcaag     240
cacggtgaca aaacaatcgt tgattccagg gccatttgcc ggtacctgtg cacgcagttc     300
ccggacgacg ggtacaagaa gctgtacggg acggggtcgc tggagcgggc gtccatagag     360
cagtggctgc aggcggaggc ccagagcttc gacgcgccga gctcggagct ggcgttccag     420
ctggcgttcg cgccgcacct caagaacgtg cggcccgacg aggcccgcgc cgcggagaac     480
gagaggaagc tgcacggcat gctgggcgtc tacgacgaca tcctctccaa gaacgagtac     540
ctcgccggcg acgacttcac cctggccgac ctctcccacc tgcccaactc ccactacatc     600
gtcaactcct ccgacagggg cagaaagctc ttcaccgcca ggaagcacgt cgccaggtgg     660
tacgacaaga tctccacccg cgactcgtgg aggcaggtca tcaagatgca gagggagcac     720
cccggcgcgt tcgagtgatc ggtcggtggt ctacgcggtg atgcatgcat gcatgcatgc     780
gccgcggcgt gttcctcgat cgccgccagc caccggcggc ttcgtcgtcg tcaggcttcg     840
taccttgacg gggttgtcga cttcgtcgta cgtccctgtg gcctgtgggc taaaataacg     900
tgaagcctgc ctacgcggtg tctcgtgtct taccttttaa atttgcacca tatatacgca     960
ctgtcttttc tgggtatttg ttgtattgtg atgtacggag tattcatcaa ctccttttgc    1020
aagattggtc aattattcag gcaaaaaaaa aaaaaaaaaa aaaaaaaaaa aaaaaaaaaa    1080
aaaaaaaaaa agaaaaaaaa aaaanaaaaa aaaaaaaaaa aaaaaaaaaa aana          1134

<210> SEQ ID NO 30
<211> LENGTH: 225
<212> TYPE: PRT
<213> ORGANISM: maize

<400> SEQUENCE: 30

Met Ala Ala Gly Leu Gln Val Phe Gly Gln Pro Ala Ser Thr Asp Val
  1               5                  10                  15

Ala Arg Val Leu Thr Cys Leu Phe Glu Lys Asn Leu Glu Phe Glu Leu
                20                  25                  30

Ile Arg Thr Asp Thr Phe Lys Lys Ser His Lys Leu Pro Glu Phe Ile
            35                  40                  45
```

```
Lys Leu Arg Asp Pro Thr Gly Gln Val Thr Phe Lys His Gly Asp Lys
         50                  55                  60

Thr Ile Val Asp Ser Arg Ala Ile Cys Arg Tyr Leu Cys Thr Gln Phe
 65                  70                  75                  80

Pro Asp Asp Gly Tyr Lys Lys Leu Tyr Gly Thr Gly Ser Leu Glu Arg
                 85                  90                  95

Ala Ser Ile Glu Gln Trp Leu Gln Ala Glu Ala Gln Ser Phe Asp Ala
            100                 105                 110

Pro Ser Ser Glu Leu Ala Phe Gln Leu Ala Phe Ala Pro His Leu Lys
        115                 120                 125

Asn Val Arg Pro Asp Glu Ala Arg Ala Ala Glu Asn Glu Arg Lys Leu
    130                 135                 140

His Gly Met Leu Gly Val Tyr Asp Asp Ile Leu Ser Lys Asn Glu Tyr
145                 150                 155                 160

Leu Ala Gly Asp Asp Phe Thr Leu Ala Asp Leu Ser His Leu Pro Asn
                165                 170                 175

Ser His Tyr Ile Val Asn Ser Ser Asp Arg Gly Arg Lys Leu Phe Thr
            180                 185                 190

Ala Arg Lys His Val Ala Arg Trp Tyr Asp Lys Ile Ser Thr Arg Asp
        195                 200                 205

Ser Trp Arg Gln Val Ile Lys Met Gln Arg Glu His Pro Gly Ala Phe
    210                 215                 220

Glu
225

<210> SEQ ID NO 31
<211> LENGTH: 1007
<212> TYPE: DNA
<213> ORGANISM: maize

<400> SEQUENCE: 31
aacacaggct gttgtttgct tcttttggta aaggctttag ctgcggcaga tccaccggcg      60
gcgccccgag aatcgaagat gccggtgaag gtgttcggat cgccgacgtc ggcggaggtc     120
gcccgcgtcc tggcctgcct gttcgagaag gacgtcgagt tccagctcat ccgcgtcgac     180
tccttccgcg gcaccaagcg cctgccccag tacctcaagc tccagccgca cggcgaggcg     240
ctcaccttcg aggacggcaa cgtcaccctc gtcgagtcga ggaagatcct cgccacatc      300
gccgacaagt acaagaacca ggggtacagg gacctgttcg gccgggcgc gctggagcgg     360
gcctccatcg agcagtggct gcagacggag gcgcagagct tcgacgtccc cagcgccgac     420
atggtctaca gcctcgccta cctgccgccc gacatgcagc tcgacggcag gggcgtcggc     480
ggcctcccgg cggcgacggg gacgatgaac ccggcgcacc ggcagaaggt ggaggagatg     540
ctgcagctgt tcgagaagag ccgcaggcag ctgggcaagc tgctggacat ctacgagcag     600
cgccttggcg aggaggcctt cctggccgga ggcaagttca cgctcgccga cctgtcccac     660
ctgcccaacg ccgaccgcct cgccggcgac ccgcggtccg cacgcctcat ggagtcgcgc     720
aggaacgtca gcaagtggtg ggacaccgta tcccgccgcg actcttgggt cagggtcaag     780
gagttgcagc gccgccgtc cgcggaggcg cccttctgat gtcgatcgat cgcaaattaa     840
ggcggtggcc tttgctcaag cctacgtgtt cggtttctgc ataatttttt aataaataaa     900
cgccactggc ccctctacgt cattggcgat tgttcattgt gtaataaatc gttcaagagc     960
atatgatgct tcttgccgtg aaaaaaaaaa aaaaaaaaa aaaaaaa                    1007
```

<210> SEQ ID NO 32
<211> LENGTH: 246
<212> TYPE: PRT
<213> ORGANISM: maize

<400> SEQUENCE: 32

```
Met Pro Val Lys Val Phe Gly Ser Pro Thr Ser Ala Glu Val Ala Arg
  1               5                  10                  15

Val Leu Ala Cys Leu Phe Glu Lys Asp Val Glu Phe Gln Leu Ile Arg
             20                  25                  30

Val Asp Ser Phe Arg Gly Thr Lys Arg Leu Pro Gln Tyr Leu Lys Leu
         35                  40                  45

Gln Pro His Gly Glu Ala Leu Thr Phe Glu Asp Gly Asn Val Thr Leu
     50                  55                  60

Val Glu Ser Arg Lys Ile Leu Arg His Ile Ala Asp Lys Tyr Lys Asn
 65                  70                  75                  80

Gln Gly Tyr Arg Asp Leu Phe Gly Pro Gly Ala Leu Glu Arg Ala Ser
                 85                  90                  95

Ile Glu Gln Trp Leu Gln Thr Glu Ala Gln Ser Phe Asp Val Pro Ser
            100                 105                 110

Ala Asp Met Val Tyr Ser Leu Ala Tyr Leu Pro Pro Asp Met Gln Leu
        115                 120                 125

Asp Gly Arg Gly Val Gly Gly Leu Pro Ala Ala Thr Gly Thr Met Asn
    130                 135                 140

Pro Ala His Arg Gln Lys Val Glu Glu Met Leu Gln Leu Phe Glu Lys
145                 150                 155                 160

Ser Arg Arg Gln Leu Gly Lys Leu Leu Asp Ile Tyr Glu Gln Arg Leu
                165                 170                 175

Gly Glu Glu Ala Phe Leu Ala Gly Gly Lys Phe Thr Leu Ala Asp Leu
            180                 185                 190

Ser His Leu Pro Asn Ala Asp Arg Leu Ala Gly Asp Pro Arg Ser Ala
        195                 200                 205

Arg Leu Met Glu Ser Arg Arg Asn Val Ser Lys Trp Trp Asp Thr Val
    210                 215                 220

Ser Arg Arg Asp Ser Trp Val Arg Val Lys Glu Leu Gln Arg Pro Pro
225                 230                 235                 240

Ser Ala Glu Ala Pro Phe
                245
```

<210> SEQ ID NO 33
<211> LENGTH: 911
<212> TYPE: DNA
<213> ORGANISM: maize

<400> SEQUENCE: 33

| | |
|---|---|
| cggagcaaga ggaaagccat ggctacgccg gcggcggtga tgaagttgta cgggtgggct | 60 |
| atctcgccgt tcgtgtcgcg ggctctgctg gccctgaggg aggccggcgt cgactacgag | 120 |
| ctcgtcccca tgagccccca ggccggcgac caccggcgcc cggagcacct cgccaggaac | 180 |
| cctttcgcca tggtgccggt gctcgaggac ggcgacctca cgctctttga atcccgggcg | 240 |
| atcgcgaggc acgttctccg caagcacagg ccggagctcc tgggcgccgg cgccggcggc | 300 |
| agcctcgagc gggcggcgat ggtggacgtg tggctcgagg tggaggcgca ccagctgagc | 360 |
| ccgccagcgg tcgccatcgt ggtggagtgc ttcgctgcgc gctgctcgg ccgcgagcgc | 420 |
| gaccagacgg tcgtcgacga gaacgtggag aagctcagga aggtgctcga ggtgtacgag | 480 |

```
gcgcggcttg gcgagtgcag gtacctcgcc ggcgacttcc tcagcctcgc cgacctcagc       540
cccttcacca tcatgcactg catcatggcc accgagtacg ccgccgccct ggtcgaggcg       600
ctcccgcgcg tcagcgcctg gtgggagggc ctcgccgcgc gccccgcggc caagaaggtg       660
gcggagttca taccggtcgg cgcggccgga ctgctggagc accctcccaa acaacaggat       720
tgatgcatga tgaagcaagc ctgcctaatg tgcctgttgc gcttaatact ttcccacgtg       780
tactttccca caacgttgac agaagttatt caataactag tctctatgta acgtaatggt       840
gtggtgtgca cttcaatgaa taccatgagg tggctggttc aaaaaaaaaa aaaaaaaaaa       900
aaaaaaaaaa a                                                            911
```

<210> SEQ ID NO 34
<211> LENGTH: 234
<212> TYPE: PRT
<213> ORGANISM: maize

<400> SEQUENCE: 34

```
Met Ala Thr Pro Ala Ala Val Met Lys Leu Tyr Gly Trp Ala Ile Ser
 1               5                  10                  15

Pro Phe Val Ser Arg Ala Leu Leu Ala Leu Glu Glu Ala Gly Val Asp
            20                  25                  30

Tyr Glu Leu Val Pro Met Ser Pro Gln Ala Gly Asp His Arg Arg Pro
        35                  40                  45

Glu His Leu Ala Arg Asn Pro Phe Ala Met Val Pro Val Leu Glu Asp
    50                  55                  60

Gly Asp Leu Thr Leu Phe Glu Ser Arg Ala Ile Ala Arg His Val Leu
65                  70                  75                  80

Arg Lys His Arg Pro Glu Leu Leu Gly Ala Gly Ala Gly Ser Leu
                85                  90                  95

Glu Arg Ala Ala Met Val Asp Val Trp Leu Glu Val Glu Ala His Gln
            100                 105                 110

Leu Ser Pro Pro Ala Val Ala Ile Val Val Glu Cys Phe Ala Ala Pro
        115                 120                 125

Leu Leu Gly Arg Glu Arg Asp Gln Thr Val Val Asp Glu Asn Val Glu
    130                 135                 140

Lys Leu Arg Lys Val Leu Glu Val Tyr Glu Ala Arg Leu Gly Glu Cys
145                 150                 155                 160

Arg Tyr Leu Ala Gly Asp Phe Leu Ser Leu Ala Asp Leu Ser Pro Phe
                165                 170                 175

Thr Ile Met His Cys Ile Met Ala Thr Glu Tyr Ala Ala Ala Leu Val
            180                 185                 190

Glu Ala Leu Pro Arg Val Ser Ala Trp Trp Glu Gly Leu Ala Ala Arg
        195                 200                 205

Pro Ala Ala Lys Lys Val Ala Glu Phe Ile Pro Val Gly Ala Ala Gly
    210                 215                 220

Leu Leu Glu His Pro Pro Lys Gln Gln Asp
225                 230
```

<210> SEQ ID NO 35
<211> LENGTH: 1098
<212> TYPE: DNA
<213> ORGANISM: maize

<400> SEQUENCE: 35

```
gcagcattgt accctatgtt catgccacca tggaagggct tcgtattgga gcaccgatta       60
```

-continued

```
tgcaggttta tcatgagaaa tcttttatct tacctgatgt ttcaagggtg cttgcttgcc      120
tttatgagaa ggatgtcaag tttgagactc acacagcctc atacaggagc ctactcggat      180
tgcaggcatc atctcatgct ccagttccat tctatgaagg ccctactttt ctagaagaat      240
ccagagaaat ctgccgttat atagcagaaa agtatgaaaa tcaaggatat ccgttcctcc      300
ttggaaagga tgcccttgag agggcttcaa ttgaacaatg gctccacaac gaggagcatg      360
ctttcaaccc tccgagccgg gccttgttct ttcatttggc ctttcccctg ggtgaaggag      420
aagatgatga tattgatgtt catacaagga agctagaaga ggttctggaa gtttatgagc      480
aaaggctcag tgacagcgaa ttccttgttg gaaacaagtt cactcttgcc gaccttgttc      540
acctgccaaa ttcccactat atcaaagcat ctaacaagtt tctttacctt tatgattcga      600
ggaaaaatgt aaggaggtgg tgggatgcta tttctgaccg gagttcttgg aagaaagtgc      660
tgaggtatat gaagagcgtg gaggagaaga acaaacaaga gaactcaag aagcagcagc      720 agcagcagga gaggctcct agaacctcca ccgacccaac tcgggtagac tcgagaaagc      780
agagcagaac agagcctcgg acaatattgg ttcctcctgc tgataacgag tcatcagctt      840
cgatagttcc tcgaacaaag aagcctcttc ctggtgatca cttagtgtct actcaacaaa      900
ttgatggtgt tggtatgcca gccacaaatt gatggtgatg gtcgtcttag tggtgtttgt      960
cttgtctttt attgtttggt tctttaacaa gagttatatt tttaccatca aaaaaaaaa     1020 aaaaaaaaaa aaaaaaaaaa aaaaaaaaaa aaaaaaaaaa aaaaaaaaaa aaaaaaaaaa     1080
aaaaaaaaaa aaaaaaaa                                                    1098
```

<210> SEQ ID NO 36
<211> LENGTH: 300
<212> TYPE: PRT
<213> ORGANISM: maize

<400> SEQUENCE: 36

```
Met Glu Gly Leu Arg Ile Gly Ala Pro Ile Met Gln Val Tyr His Glu
 1               5                  10                  15

Lys Ser Phe Ile Leu Pro Asp Val Ser Arg Val Leu Ala Cys Leu Tyr
            20                  25                  30

Glu Lys Asp Val Lys Phe Glu Thr His Thr Ala Ser Tyr Arg Ser Leu
        35                  40                  45

Leu Gly Leu Gln Ala Ser Ser His Ala Pro Val Pro Phe Tyr Glu Gly
    50                  55                  60

Pro Thr Phe Leu Glu Glu Ser Arg Glu Ile Cys Arg Tyr Ile Ala Glu
65                  70                  75                  80

Lys Tyr Glu Asn Gln Gly Tyr Pro Phe Leu Leu Gly Lys Asp Ala Leu
                85                  90                  95

Glu Arg Ala Ser Ile Glu Gln Trp Leu His Asn Glu Glu His Ala Phe
            100                 105                 110

Asn Pro Pro Ser Arg Ala Leu Phe Phe His Leu Ala Phe Pro Leu Gly
        115                 120                 125

Glu Gly Glu Asp Asp Asp Ile Asp Val His Thr Arg Lys Leu Glu Glu
    130                 135                 140

Val Leu Glu Val Tyr Glu Gln Arg Leu Ser Asp Ser Glu Phe Leu Val
145                 150                 155                 160

Gly Asn Lys Phe Thr Leu Ala Asp Leu Val His Leu Pro Asn Ser His
                165                 170                 175

Tyr Ile Lys Ala Ser Asn Lys Phe Leu Tyr Leu Tyr Asp Ser Arg Lys
```

-continued

```
                    180                 185                 190
Asn Val Arg Arg Trp Trp Asp Ala Ile Ser Asp Arg Ser Trp Lys
                195                 200                 205
Lys Val Leu Arg Tyr Met Lys Ser Val Glu Glu Lys Asn Lys Gln Glu
            210                 215                 220
Glu Leu Lys Lys Gln Gln Gln Gln Glu Glu Ala Pro Arg Thr Ser
225                 230                 235                 240
Thr Asp Pro Thr Arg Val Asp Ser Arg Lys Gln Ser Arg Thr Glu Pro
                245                 250                 255
Arg Thr Ile Leu Val Pro Pro Ala Asp Asn Glu Ser Ser Ala Ser Ile
                260                 265                 270
Val Pro Arg Thr Lys Lys Pro Leu Pro Gly Asp His Leu Val Ser Thr
                275                 280                 285
Gln Gln Ile Asp Gly Val Gly Met Pro Ala Thr Asn
        290                 295                 300
```

<210> SEQ ID NO 37
<211> LENGTH: 937
<212> TYPE: DNA
<213> ORGANISM: maize

<400> SEQUENCE: 37

| | |
|---|---|
| gttccgctcc gccacaccaa aaagaaacaa aagcctacgg cgatcgatcg agaagctggt | 60 |
| catcgtcagg atgtcatcgc cgcagtcagc agcgccgccc gtgaagctga tcacggcgtt | 120 |
| cggcagcccg ttcgcccacc gcgtggaggt ggcgctcgct ctcaaggggg tgccgtacga | 180 |
| gctggtcgtg gaggacctag ccaacaagag cgagctgctg ctcacgcaca acccagtcca | 240 |
| ccagtcggtc cctgtcctcc tccacggtga ccgcgctgtc tgcgagtccc tcgtcatcgt | 300 |
| cgagtacgtc gacgagacct tccaccatgg cgcggcgccg gggatcctcc cggccgaccc | 360 |
| ctacgaccgc gccaccgccc gcttctgggc tgacttcatc gacaacaagt gcttgaagcc | 420 |
| gatgtggctc tcgatgtgga cggacggcga ggcgcaggcg cggttcgtca gggagacgaa | 480 |
| ggagagcctg ggggtgctgg acgcgcaact ccaggggaag aggttcttcg ccggcgacgc | 540 |
| gctcggcttc gtcgacctcg ccgcctgcac gctggctcac tggctaggcg tgctggagga | 600 |
| agtggccgga gtgcacctga tagcggcgga cggcgagtac cccgctctgc gccgctgggc | 660 |
| caaggagtac gtctccgatg aggtcgtgag ccggtcgctg ccggacaggg acgagctcgt | 720 |
| cgccttcttc accgccagca aggagaggta caagtcgtgg gtcagggcag aggtggagcg | 780 |
| acattgatcg ctaaaaatga cgctggttgt tgaactctgt acgttctctt gtagtcgaat | 840 |
| aatgtgtgga tcgttatgta tacgtactac gtatttcatc gtgttatata catctaataa | 900 |
| gacatgcaag ctcgatcaaa aaaaaaaaaa aaaaaaa | 937 |

<210> SEQ ID NO 38
<211> LENGTH: 238
<212> TYPE: PRT
<213> ORGANISM: maize

<400> SEQUENCE: 38

```
Met Ser Ser Pro Gln Ser Ala Ala Pro Val Lys Leu Ile Thr Ala
  1               5                  10                  15
Phe Gly Ser Pro Phe Ala His Arg Val Glu Val Ala Leu Ala Leu Lys
                20                  25                  30
Gly Val Pro Tyr Glu Leu Val Val Glu Asp Leu Ala Asn Lys Ser Glu
            35                  40                  45
```

Leu Leu Leu Thr His Asn Pro Val His Gln Ser Val Pro Val Leu Leu
        50                  55                  60

His Gly Asp Arg Ala Val Cys Glu Ser Leu Val Ile Val Glu Tyr Val
 65                  70                  75                  80

Asp Glu Thr Phe His His Gly Ala Ala Pro Gly Ile Leu Pro Ala Asp
                 85                  90                  95

Pro Tyr Asp Arg Ala Thr Ala Arg Phe Trp Ala Asp Phe Ile Asp Asn
                100                 105                 110

Lys Cys Leu Lys Pro Met Trp Leu Ser Met Trp Thr Asp Gly Glu Ala
            115                 120                 125

Gln Ala Arg Phe Val Arg Glu Thr Lys Glu Ser Leu Gly Val Leu Asp
        130                 135                 140

Ala Gln Leu Gln Gly Lys Arg Phe Phe Ala Gly Asp Ala Leu Gly Phe
145                 150                 155                 160

Val Asp Leu Ala Ala Cys Thr Leu Ala His Trp Leu Gly Val Leu Glu
                165                 170                 175

Glu Val Ala Gly Val His Leu Ile Ala Ala Asp Gly Glu Tyr Pro Ala
            180                 185                 190

Leu Arg Arg Trp Ala Lys Glu Tyr Val Ser Asp Glu Val Val Ser Arg
        195                 200                 205

Ser Leu Pro Asp Arg Asp Glu Leu Val Ala Phe Phe Thr Ala Ser Lys
210                 215                 220

Glu Arg Tyr Lys Ser Trp Val Arg Ala Glu Val Glu Arg His
225                 230                 235

<210> SEQ ID NO 39
<211> LENGTH: 773
<212> TYPE: DNA
<213> ORGANISM: maize

<400> SEQUENCE: 39
cgggagccga cgacctgaag gtgctgggcc tgtggacgag cccgttcgtg atccgggtcc        60
gcatcgtgct caacctcaag ggcctggcgt acgagtacgt ggaggacgac ctcggcaaca       120
agagcgcgct cctgctcagc tccaacccgg tgcacaagac cgtgcccgtg ctgctccacg       180
cgggtcgccc cgtaaacgag tcccagatca tcctgcagta catcgacgag gtctgggcgg       240
ggaccgggcc ggccgtgctg ccgcgcgacc cctatgagcg cgcggccgcg cggttctggg       300
cggcctacat cgacgacaag gtgaagtccg cgtggctggg catgctgttc gagtgcaggg       360
acgaggggga gcgggcggag gcggtggcgc gggccggcga ggcgctcggg acgctggagg       420
gcgcgctcag ggggaagccc ttcttcggcg gcgacggcgt cggcttcgtg gacgccgtgc       480
tcggcgggta cctcggctgg ttcggggccg tcggcaggat catcggccgc aggctgatcg       540
acccgactaa gacgccgctg ctggccgcgt gggaggaccg gttccgcgcc gccgacgtgg       600
ccaagggcgt cgtaccggac gacgtcgaca agatgctcgc gttcctggag accctgctcg       660
cgaactacta ctccaagtga ctgtactgag agcgaactac tgctccaagt gactaaataa       720
gaagggctgc ttaattaata attacagtat ataaaaaaaa aaaaaaaaa aaa              773

<210> SEQ ID NO 40
<211> LENGTH: 225
<212> TYPE: PRT
<213> ORGANISM: maize

<400> SEQUENCE: 40

```
Gly Ala Asp Asp Leu Lys Val Leu Gly Leu Trp Thr Ser Pro Phe Val
  1               5                  10                  15

Ile Arg Val Arg Ile Val Leu Asn Leu Lys Gly Leu Ala Tyr Glu Tyr
                 20                  25                  30

Val Glu Asp Asp Leu Gly Asn Lys Ser Ala Leu Leu Leu Ser Ser Asn
             35                  40                  45

Pro Val His Lys Thr Val Pro Val Leu Leu His Ala Gly Arg Pro Val
         50                  55                  60

Asn Glu Ser Gln Ile Ile Leu Gln Tyr Ile Asp Glu Val Trp Ala Gly
 65                  70                  75                  80

Thr Gly Pro Ala Val Leu Pro Arg Asp Pro Tyr Glu Arg Ala Ala Ala
                 85                  90                  95

Arg Phe Trp Ala Ala Tyr Ile Asp Asp Lys Val Lys Ser Ala Trp Leu
                100                 105                 110

Gly Met Leu Phe Glu Cys Arg Asp Glu Gly Glu Arg Ala Glu Ala Val
            115                 120                 125

Ala Arg Ala Gly Glu Ala Leu Gly Thr Leu Glu Gly Ala Leu Arg Gly
130                 135                 140

Lys Pro Phe Phe Gly Gly Asp Gly Val Gly Phe Val Asp Ala Val Leu
145                 150                 155                 160

Gly Gly Tyr Leu Gly Trp Phe Gly Ala Val Gly Arg Ile Ile Gly Arg
                165                 170                 175

Arg Leu Ile Asp Pro Thr Lys Thr Pro Leu Leu Ala Ala Trp Glu Asp
            180                 185                 190

Arg Phe Arg Ala Ala Asp Val Ala Lys Gly Val Val Pro Asp Asp Val
            195                 200                 205

Asp Lys Met Leu Ala Phe Leu Glu Thr Leu Leu Ala Asn Tyr Tyr Ser
210                 215                 220

Lys
225

<210> SEQ ID NO 41
<211> LENGTH: 860
<212> TYPE: DNA
<213> ORGANISM: maize

<400> SEQUENCE: 41
agaaaaaagc ataagctgag catccatcaa tggcggatgc tgcaacgag gccgagggtc      60 tgacgctgtt gggcctgcac gtgagcccct tcgcgttgcg cgtgcgcatg gcgctgagcc     120
tcaagggcct gagctacgag tacatcgagc aggacctgtt ccacaagggc gagctcctcc     180
tcagctcaaa ccccgtgcac aagaaggtgc ccgtgctcat ccaccacggc aagcccatct     240
gcgagtccct cgccgtcgtg gagtacgtcg atgaggtctg gccggcgcc gccgccacca     300 tcctccccgc cgacccccac ggtcgcgcca ccgctcgctt ctgggccgcc tacatcgacg     360
gcaagctgtt tccggcgtgg acagggatca tgaaggcggc gacggaggaa gcgagggcgg     420
ataagctgag ggagacgcac gccgcggtcc tcaacctgga aaggccttc gccgagatca     480 gctctagctc cagcaacgac ggcgcggcct tcttcggcgg cgactccgtc gggtacctgg     540
acctcgcgct cggtgctcc ctgccgtggt tcggggcgct gcgcgccatg ctcggcgtcg     600
agatcatcga cgccgcccag gctccgctcc tggtggcgtg ggccgagcga tttggggaga     660
ccccggtggc caaggaggtg ctgccgcagc cggacgaggc tgtggcctac gccaagaaga     720
ttcaggccta ctgggcttct gctaagaact gatgagcacc gaatcctgtc atgatgaaat     780
```

-continued

```
tgaagcagca atacttgtat aacactccaa tcatggtgaa taaaggcctc taaactgttg    840
gttaataaaa aaaaaaaaaa                                                860
```

<210> SEQ ID NO 42
<211> LENGTH: 240
<212> TYPE: PRT
<213> ORGANISM: maize

<400> SEQUENCE: 42

```
Met Ala Asp Ala Gly Asn Glu Ala Glu Gly Leu Thr Leu Leu Gly Leu
 1               5                  10                  15

His Val Ser Pro Phe Ala Leu Arg Val Arg Met Ala Leu Ser Leu Lys
            20                  25                  30

Gly Leu Ser Tyr Glu Tyr Ile Glu Gln Asp Leu Phe His Lys Gly Glu
        35                  40                  45

Leu Leu Leu Ser Ser Asn Pro Val His Lys Lys Val Pro Val Leu Ile
    50                  55                  60

His His Gly Lys Pro Ile Cys Glu Ser Leu Ala Val Val Glu Tyr Val
65                  70                  75                  80

Asp Glu Val Trp Pro Gly Ala Ala Thr Ile Leu Pro Ala Asp Pro
                85                  90                  95

His Gly Arg Ala Thr Ala Arg Phe Trp Ala Ala Tyr Ile Asp Gly Lys
            100                 105                 110

Leu Phe Pro Ala Trp Thr Gly Ile Met Lys Ala Ala Thr Glu Glu Ala
        115                 120                 125

Arg Ala Asp Lys Leu Arg Glu Thr His Ala Ala Val Leu Asn Leu Glu
    130                 135                 140

Lys Ala Phe Ala Glu Ile Ser Ser Ser Ser Asn Asp Gly Ala Ala
145                 150                 155                 160

Phe Phe Gly Gly Asp Ser Val Gly Tyr Leu Asp Leu Ala Leu Gly Cys
                165                 170                 175

Ser Leu Pro Trp Phe Gly Ala Leu Arg Ala Met Leu Gly Val Glu Ile
            180                 185                 190

Ile Asp Ala Ala Gln Ala Pro Leu Leu Val Ala Trp Ala Glu Arg Phe
        195                 200                 205

Gly Glu Thr Pro Val Ala Lys Glu Val Leu Pro Gln Pro Asp Glu Ala
    210                 215                 220

Val Ala Tyr Ala Lys Lys Ile Gln Ala Tyr Trp Ala Ser Ala Lys Asn
225                 230                 235                 240
```

<210> SEQ ID NO 43
<211> LENGTH: 1228
<212> TYPE: DNA
<213> ORGANISM: maize

<400> SEQUENCE: 43

```
gtcgtcactg ctgaccatag gtggccggcc ggccgaacaa accctcggca cgatcgcctg     60
cctccataaa tctccctctt cacttcaggc gaaaaggatc aaccaaaccc tctaatccat    120
ttcggcattt ccaacgcctt cgccctacca gccacgtcgc ttcgaggccg atcgaccgag    180
cagctggtgg caatggcggc ggcggcggag gtcgtgctgc tggacttctg ggtgagcccc    240
ttcgggcagc gctgccggat cgcgctggcg gagaagggcg tggcctacga gtaccgcgag    300
caggacctcc tggacaaggg cgagctgctc ctccgctcca accccatcca agaagatc     360 cccgtcctgc tccacgccgg caggcccgtc tgcgagtcgc tcgtcatcct ccagtacatc    420
```

-continued

```
gacgaggcct ggccggacgt cgcgccgctc ctccccaagg acgaccccta cgcccgcgcg      480
caggcgcgtt tctgggccga ttacatcgac aagaagatct atgacagcca gactcggctg      540
tggaagttcg agggcgaggc gcgggagcag gcgaagaagg acctggtgga ggtcctggag      600
acctggaggg ggagctcgcc gacaagcctt tcttcggcgg cggcgccctc ggcttcgtgg      660
acgtggctct ggtgcccttc acgtcctggt tcctcgccta cgagaagctg gcgggttca       720 gcgtccagga gcactgcccc aggatcgtgg cctgggccgc gcgctgcagg gagcgggaga      780
gcgtggccaa ggccatgtcc gaccctgcca aggtgctcga gttcgtccag ttcctccaga      840
gcaagttcgg ggccaagtga tcggaagcat tgcgtgtgct gctagcctgc tatgccctat      900
gcaggccagg ctggtgcttt gatctgctcg atcagctcta tgcccatgct agcgttgcat      960
agcgcagttg atgtgtgatg tgtctggttg gttgtagctg ctctttgcct ggtttcgtac     1020
gtcagtgtaa ggtttcaggt tttcagtgtc tggggtagct ctgcgttgcc cttgccctg       1080 ccccctacct agcggctctt gagctcttcg gctcgccagc aataaagttg cagaggcttt     1140
agctaaaagt ttctgtattt tttagttgac gattattggt ccaatgtatt cggaattttt     1200
gttctctcta aaaaaaaaaa aaaaaaaa                                        1228
```

<210> SEQ ID NO 44
<211> LENGTH: 230
<212> TYPE: PRT
<213> ORGANISM: maize

<400> SEQUENCE: 44

```
Met Ala Ala Ala Glu Val Val Leu Leu Asp Phe Trp Val Ser Pro
 1               5                  10                  15

Phe Gly Gln Arg Cys Arg Ile Ala Leu Ala Glu Lys Gly Val Ala Tyr
                20                  25                  30

Glu Tyr Arg Glu Gln Asp Leu Leu Asp Lys Gly Glu Leu Leu Leu Arg
            35                  40                  45

Ser Asn Pro Ile His Lys Lys Ile Pro Val Leu Leu His Ala Gly Arg
        50                  55                  60

Pro Val Cys Glu Ser Leu Val Ile Leu Gln Tyr Ile Asp Glu Ala Trp
    65                  70                  75                  80

Pro Asp Val Ala Pro Leu Leu Pro Lys Asp Asp Pro Tyr Ala Arg Ala
                85                  90                  95

Gln Ala Arg Phe Trp Ala Asp Tyr Ile Asp Lys Lys Ile Tyr Asp Ser
            100                 105                 110

Gln Thr Arg Leu Trp Lys Phe Glu Gly Glu Ala Arg Glu Gln Ala Lys
        115                 120                 125

Lys Asp Leu Val Glu Val Leu Glu Thr Trp Arg Gly Ser Ser Pro Thr
    130                 135                 140

Ser Leu Ser Ser Ala Ala Ala Pro Ser Ala Ser Trp Thr Trp Leu Trp
145                 150                 155                 160

Cys Pro Ser Arg Pro Gly Ser Ser Pro Thr Arg Ser Trp Ala Gly Ser
                165                 170                 175

Ala Ser Arg Ser Thr Ala Pro Gly Ser Trp Pro Gly Pro Arg Ala Ala
            180                 185                 190

Gly Ser Gly Arg Ala Trp Pro Arg Pro Cys Pro Thr Leu Pro Arg Cys
        195                 200                 205

Ser Ser Ser Ser Ser Ser Arg Ala Ser Ser Gly Pro Ser Asp Arg
    210                 215                 220

Lys His Cys Val Cys Cys
```

<210> SEQ ID NO 45
<211> LENGTH: 840
<212> TYPE: DNA
<213> ORGANISM: maize

<400> SEQUENCE: 45

| | | | | | |
|---|---|---|---|---|---|
| caagctaagc | aagtgccaac | caacgagtag | caggaaacat | gtctccgccc | gtcaagatcc | 60 |
| tcggccacta | cgcgagcccg | tactcgcacc | gcgtcgaggc | cgctctgcgg | ctcaagggcg | 120 |
| tgccgtacga | gctggtccag | gaagacctgg | gcaacaagag | cgagctgctg | ctcgccaaga | 180 |
| accctgtcca | agaaggtg | cccgtgctcc | tccatggcga | cagggccgtc | tgcgagtccc | 240 |
| tcctcatcgt | cgagtacgtc | gacgaggcct | tcgacgggcc | gtccatcctg | ccggccgacc | 300 |
| cccacgaccg | tgccgtcgcc | cgtttctggg | cgaacttctt | ggacaccaag | ttctcccagc | 360 |
| cgttctggct | ggcgtactgg | gcggagggcg | aggcgcagaa | ggccgtggtg | aaggaggcca | 420 |
| aggagaacct | ggcgctcctg | gaggcgcagc | tcggcgggaa | gaggttcttc | ggcggcgaca | 480 |
| cgcccgggta | cctcgacata | gccgcgtgca | cgttgggtcc | ttggatcggc | gtgctcgagg | 540 |
| aggtgactgg | agtggccttg | ctggacgccg | acgagttccc | cgctctatgc | cagtgggcca | 600 |
| gggactacag | ctccagtgaa | gcgctcaggc | catgcctgcc | ggacagggac | cgactcgttg | 660 |
| cctacttcac | cgagaacaag | gagaagtaca | agacatttgc | caaggcaacg | ttgcatcagt | 720 |
| agctgctagt | tgggtgcaaa | ccgcttgttt | atctctgtgt | ggaataatgt | atacgtacgt | 780 |
| gctccctcga | tatcaaataa | atcagctacc | ggagttgact | gtagtcaaaa | aaaaaaaaa | 840 |

<210> SEQ ID NO 46
<211> LENGTH: 227
<212> TYPE: PRT
<213> ORGANISM: maize

<400> SEQUENCE: 46

Met Ser Pro Pro Val Lys Ile Leu Gly His Tyr Ala Ser Pro Tyr Ser
 1               5                  10                  15

His Arg Val Glu Ala Ala Leu Arg Leu Lys Gly Val Pro Tyr Glu Leu
            20                  25                  30

Val Gln Glu Asp Leu Gly Asn Lys Ser Glu Leu Leu Leu Ala Lys Asn
        35                  40                  45

Pro Val His Lys Lys Val Pro Val Leu Leu His Gly Asp Arg Ala Val
    50                  55                  60

Cys Glu Ser Leu Leu Ile Val Glu Tyr Val Asp Glu Ala Phe Asp Gly
65                  70                  75                  80

Pro Ser Ile Leu Pro Ala Asp Pro His Asp Arg Ala Val Ala Arg Phe
                85                  90                  95

Trp Ala Asn Phe Leu Asp Thr Lys Phe Ser Gln Pro Phe Trp Leu Ala
            100                 105                 110

Tyr Trp Ala Glu Gly Glu Ala Gln Lys Ala Val Val Lys Glu Ala Lys
        115                 120                 125

Glu Asn Leu Ala Leu Leu Glu Ala Gln Leu Gly Gly Lys Arg Phe Phe
    130                 135                 140

Gly Gly Asp Thr Pro Gly Tyr Leu Asp Ile Ala Ala Cys Thr Leu Gly
145                 150                 155                 160

Pro Trp Ile Gly Val Leu Glu Glu Val Thr Gly Val Ala Leu Leu Asp
                165                 170                 175

```
Ala Asp Glu Phe Pro Ala Leu Cys Gln Trp Ala Arg Asp Tyr Ser Ser
            180                 185                 190

Ser Glu Ala Leu Arg Pro Cys Leu Pro Asp Arg Asp Arg Leu Val Ala
            195                 200                 205

Tyr Phe Thr Glu Asn Lys Glu Lys Tyr Lys Thr Phe Ala Lys Ala Thr
            210                 215                 220

Leu His Gln
225

<210> SEQ ID NO 47
<211> LENGTH: 970
<212> TYPE: DNA
<213> ORGANISM: maize

<400> SEQUENCE: 47
acgcaaacgc aagctcccaa gcagctacca accagccggg agagggagcg cacgcactgc      60
gagaatggcc acggccggcg gaggggccgg gcatctgaag ctgctgggcg cgtggccgag     120
ccccttcgtg aaccgtgtac gcatggcgct gcacctcaag gggctggagt acgaaacgt     180 ggaggaggac ctcaccaaca gagcgacct gctcctcgcc tccaaccccg tccacaagct     240
cgttcccgtc ctcctccacg gcgacaagcc catctccgag tcactcgtca tcgtggagta     300
cctcgacgac gccttccccg gcgctggcca ggccgtcctc cccgccgacc cctatgaacg     360
cgccgtcgct cgcttctggg ccaaatacgt cgacggcaag ttgcacggca tgatggtgaa     420
ggcgctcatg ggggcaacgg aggaggagag ggcgacggcg acggtggacg cgctggccgc     480
tatggacacg ctggagggcg cgttcgccga gtgctccggc gggaaaaagt tcttcgccgg     540
cgacgcgccc gggtacctgg acgtcgcgct gggaggcttc atcggctggc tgcgcgcctg     600
ggacaaggtg gggggcgtca agctgctgga cgccggccgg gtcccgcgcc tggccacgtg     660
ggcggagcgc ttcgccgcgc tcgacgtagc caaggaggtc atcccggacc ccgaccacat     720
cgccgagttt gccaaggtgc tgcaggcacg ctccgcggca gctgccacca gcaactgagc     780
tcgcaagtga atgctgctgc tctgccttcc tgataaaatc atatcatggt acccggtttg     840
ttcgtttaat ctggcgcgga aaaacatgg tttgttgtcg taccaaacta agagtatgca     900
tgcatgcttg ttcttaatta tatgtacatt cgttcaagaa aaaaaaaaa aaaaaaaaa     960 aaaaaaaaa                                                            970

<210> SEQ ID NO 48
<211> LENGTH: 237
<212> TYPE: PRT
<213> ORGANISM: maize

<400> SEQUENCE: 48

Met Ala Thr Ala Gly Gly Gly Ala Gly His Leu Lys Leu Leu Gly Ala
  1               5                  10                  15

Trp Pro Ser Pro Phe Val Asn Arg Val Arg Met Ala Leu His Leu Lys
             20                  25                  30

Gly Leu Glu Tyr Glu Asn Val Glu Asp Leu Thr Asn Lys Ser Asp
         35                  40                  45

Leu Leu Leu Ala Ser Asn Pro Val His Lys Leu Pro Val Leu Leu
     50                  55                  60

His Gly Asp Lys Pro Ile Ser Glu Ser Leu Val Ile Val Glu Tyr Leu
 65                  70                  75                  80

Asp Asp Ala Phe Pro Gly Ala Gly Gln Ala Val Leu Pro Ala Asp Pro
                 85                  90                  95
```

```
Tyr Glu Arg Ala Val Ala Arg Phe Trp Ala Lys Tyr Val Asp Gly Lys
            100                 105                 110

Leu His Gly Met Met Val Lys Ala Leu Met Gly Ala Thr Glu Glu Glu
        115                 120                 125

Arg Ala Thr Ala Thr Val Asp Ala Leu Ala Ala Met Asp Thr Leu Glu
    130                 135                 140

Gly Ala Phe Ala Glu Cys Ser Gly Gly Lys Lys Phe Phe Ala Gly Asp
145                 150                 155                 160

Ala Pro Gly Tyr Leu Asp Val Ala Leu Gly Gly Phe Ile Gly Trp Leu
                165                 170                 175

Arg Ala Trp Asp Lys Val Gly Gly Val Lys Leu Leu Asp Ala Gly Arg
            180                 185                 190

Val Pro Arg Leu Ala Thr Trp Ala Glu Arg Phe Ala Ala Leu Asp Val
        195                 200                 205

Ala Lys Glu Val Ile Pro Asp Pro Asp His Ile Ala Glu Phe Ala Lys
    210                 215                 220

Val Leu Gln Ala Arg Ser Ala Ala Ala Thr Ser Asn
225                 230                 235
```

<210> SEQ ID NO 49
<211> LENGTH: 756
<212> TYPE: DNA
<213> ORGANISM: maize

<400> SEQUENCE: 49

```
cggcggtgag gctggtgggc tccttcgcca gcccgttcgt ccaccgcgcc gaggtggccc      60
tgcgcctcaa agggtgccc  tacgagctca tcctggagga cctgggcaac aagagcgagc     120
tgctgctggc acacaacccc gtgcacaaac tcgtgcccgt gctcctccac ggcgacaggg     180
ccatctccga gtcgctcgtc atcctcgagt acgtcgacga ggccttcgac gggccgcctc     240
tcctccccgc ggaaccccac gcgagggcgg acgcgcggtt ctgggcccac ttcatcgacc     300
aaaagttcgc gcggccgttc tggatgtcgt tctggacgga cgacgaggag cgcagggagg     360
ctatggcgaa ggaggccaag gagaacctgg ctctgctcga ggcgcagctc aggggcaga     420
ggttcttcgg cggcgaggcc atcggcttcg tcgacatcgc cgcctgtgcg ctggcgcact     480
gggtcggggt catcgaggag gctgccgggg tggtcctcgt cggcggcgag gagttcccag     540
cgctccgcga gtgggccgac gcctacgtca cgacgccac cgtgaagcag tgcttgagga      600
gccgcgacga gctcgtcgat tacttctccg ccaggaagga gatgtacttg ctgcgagcga     660
gggccactcc gcgcagctga tctggacccc atgtttcctt ccgttcgcaa taagccaata     720
ataaagacta gtttggtaaa aaaaaaaaaa aaaaaa                               756
```

<210> SEQ ID NO 50
<211> LENGTH: 225
<212> TYPE: PRT
<213> ORGANISM: maize

<400> SEQUENCE: 50

```
Ala Val Arg Leu Val Gly Ser Phe Ala Ser Pro Phe Val His Arg Ala
 1               5                  10                  15

Glu Val Ala Leu Arg Leu Lys Gly Val Pro Tyr Glu Leu Ile Leu Glu
            20                  25                  30

Asp Leu Gly Asn Lys Ser Glu Leu Leu Leu Ala His Asn Pro Val His
        35                  40                  45
```

-continued

```
Lys Leu Val Pro Val Leu Leu His Gly Asp Arg Ala Ile Ser Glu Ser
 50                  55                  60

Leu Val Ile Leu Glu Tyr Val Asp Glu Ala Phe Asp Gly Pro Pro Leu
 65                  70                  75                  80

Leu Pro Ala Glu Pro His Ala Arg Ala Asp Ala Arg Phe Trp Ala His
                 85                  90                  95

Phe Ile Asp Gln Lys Phe Ala Arg Pro Phe Trp Met Ser Phe Trp Thr
                100                 105                 110

Asp Asp Glu Glu Arg Arg Glu Ala Met Ala Lys Glu Ala Lys Glu Asn
                115                 120                 125

Leu Ala Leu Leu Glu Ala Gln Leu Arg Gly Gln Arg Phe Phe Gly Gly
130                 135                 140

Glu Ala Ile Gly Phe Val Asp Ile Ala Ala Cys Ala Leu Ala His Trp
145                 150                 155                 160

Val Gly Val Ile Glu Glu Ala Ala Gly Val Val Leu Val Gly Gly Glu
                165                 170                 175

Glu Phe Pro Ala Leu Arg Glu Trp Ala Asp Ala Tyr Val Asn Asp Ala
                180                 185                 190

Thr Val Lys Gln Cys Leu Arg Ser Arg Asp Glu Leu Val Asp Tyr Phe
                195                 200                 205

Ser Ala Arg Lys Glu Met Tyr Leu Leu Arg Ala Arg Ala Thr Pro Arg
    210                 215                 220

Ser
225

<210> SEQ ID NO 51
<211> LENGTH: 967
<212> TYPE: DNA
<213> ORGANISM: maize

<400> SEQUENCE: 51
cagccacggc gagcaagcga tgatgagcgg cggcgcggtg aaggtgatcg gcgccctgga      60
cagcccgttc agccaccgcg cggaggcggc gctgcgcctc aagggagtcc cctacgagct     120
tgtcctggag aaggacctgc gcgacaaaag cgagctgctg ctgcggcaca ccccgtcca     180 caagaaggtg cccgtgctcc ttcacggcgg ccgccgcgcc gtctgcgagt cgctcgtcat     240
cgtcgagtac gttgacgagg cattccgcgg cccgccactc ctccccgccg accctccgc     300 ccgcgccgcc gcccgcttct gggcccgctt catcgacgac aagtgctcga cgcccttctg     360
gctggcgatg tggacggagg gcgaggcgca gaggggttc gtgaaggaga tcaaggagaa     420
cctgaagctg ctggaggggc aggtgaaggg caagcggttc ttcggcggcg cgacgtggg     480 ctacctcgac gtcgccgcca gcgtgttcgc gcactggctt ccggtctgcg aggaggtcgc     540
gggcgtcagc ctggtcacgg ccgaggagta cccggacctg tgccggtggg cgagggagta     600
cacctcccac gacgccgtca gcggtgcct gcctggcagg gaggagctgc tcgcccgttt     660
cagcgccagg aaggactcgt tgtggccgc ggcgaggtca atggcgccgg cgccggagaa     720
gtaatctatg ggaattcaac tgggtgcatg gatagcataa atttaagtat tgtgacaagt     780
ggtcaggact gctgtcacgt accgtcgagc ccgggagata tgtactctcc ggctcaggca     840
aatgccatct gtcctgatgc atgtgttttg ttcctacttt gtttgactgc ttgttgaata     900 aaaaagata tccggttgtg ttcaaaaaaa aaaaaaaaaa aaaaaaaaaa aaaaaaaaa      960 aaaaaaa                                                              967
```

```
<210> SEQ ID NO 52
<211> LENGTH: 234
<212> TYPE: PRT
<213> ORGANISM: maize

<400> SEQUENCE: 52

Met Met Ser Gly Gly Ala Val Lys Val Ile Gly Ala Leu Asp Ser Pro
 1               5                  10                  15

Phe Ser His Arg Ala Glu Ala Ala Leu Arg Leu Lys Gly Val Pro Tyr
                20                  25                  30

Glu Leu Val Leu Glu Lys Asp Leu Arg Asp Lys Ser Glu Leu Leu Leu
            35                  40                  45

Arg His Asn Pro Val His Lys Lys Val Pro Val Leu Leu His Gly Gly
        50                  55                  60

Arg Arg Ala Val Cys Glu Ser Leu Val Ile Val Glu Tyr Val Asp Glu
 65                 70                  75                  80

Ala Phe Arg Gly Pro Pro Leu Leu Pro Ala Asp Pro Ser Ala Arg Ala
                85                  90                  95

Ala Ala Arg Phe Trp Ala Arg Phe Ile Asp Asp Lys Cys Ser Thr Pro
            100                 105                 110

Phe Trp Leu Ala Met Trp Thr Glu Gly Glu Ala Gln Arg Gly Phe Val
        115                 120                 125

Lys Glu Ile Lys Glu Asn Leu Lys Leu Leu Glu Gly Gln Val Lys Gly
    130                 135                 140

Lys Arg Phe Phe Gly Gly Gly Asp Val Gly Tyr Leu Asp Val Ala Ala
145                 150                 155                 160

Ser Val Phe Ala His Trp Leu Pro Val Cys Glu Glu Val Ala Gly Val
                165                 170                 175

Ser Leu Val Thr Ala Glu Glu Tyr Pro Asp Leu Cys Arg Trp Ala Arg
            180                 185                 190

Glu Tyr Thr Ser His Asp Ala Val Lys Arg Cys Leu Pro Gly Arg Glu
        195                 200                 205

Glu Leu Leu Ala Arg Phe Ser Ala Arg Lys Asp Ser Phe Val Ala Ala
    210                 215                 220

Ala Arg Ser Met Ala Pro Ala Pro Glu Lys
225                 230

<210> SEQ ID NO 53
<211> LENGTH: 1100
<212> TYPE: DNA
<213> ORGANISM: maize

<400> SEQUENCE: 53
acctcagaca ctctgcatat atcctctgcg cgtgtatctc gtcgaacaga gccgaaagct     60
ggagcttcca atggcgggag caacgacct gaaggtgctc ggcgtgtgga cgagcccgtt    120
cgtgatccgg gtccgcatcg tgctcaacct gaagggcctg gcgtacgagt acgtggagga    180
ggacctcggc aacaagagcg cgctcctcct gggatccaac ccggtgcaca agagcgtgcc    240
ggtgctcctc cacgccggcc gcgccataaa cgagtcccag gtcatcctgc agtacatcga    300
cgaggtgtgg gcggggacgg ggccggccgt gcttccggcc gaccctacg agcgcgcggt     360 ggcgcggttc tggggcgcgt acatcgacga caaggtggag tcggcgtggc tggggatgct    420
gttcaggtgc gcgaacgagg aggagagggc ggcggcggtg gcgcgcgccc gcaggcgct     480 cgacgcgctg gagggcgcgt tccgggactg ctccaggggg aggccgttct tcggcggcga    540
cgacatcggg ttcgtggacg ccgttctcgg cgggtacctc ggctggttcg gggccgtcgg    600
```

```
caggatcatc gggagcaggc tcatcgaccc ggcccggacg ccgctgctgg ccgcgtggga    660
ggaccggttc cgcgccgccg acgtggccaa gggcgtcgtg cccgacgacc tcgacaagat    720
gctcgcgttc ctgcagaccc tgcgcgctat gaactacgcc aagtgagagt gtttcgtcgc    780
atgaacgtgt gccgtgccgt gcacgaccta tgatcagttc atgtcgatac gtctatcact    840
cagttttgct tcttccgtca ataatcggtg tgctgaatac atgtacaaca gctgcctata    900
attttgcttc tttcttctaa tacctccgtt tttaatttga tagttcaact ttataataac    960
aaatgtcaaa tttaaaaaaa aaatcggaag gagtattttt ttaatacatc caagtccatc   1020
caataaaagt gctcgtgggg ctttctatta aaaaaaaaaa aaaaaaaaaa aaaaaaaaa    1080 aaaaaaaaaa aaaaaaaaaa                                               1100
```

<210> SEQ ID NO 54
<211> LENGTH: 231
<212> TYPE: PRT
<213> ORGANISM: maize

<400> SEQUENCE: 54

```
Met Ala Gly Gly Asn Asp Leu Lys Val Leu Gly Val Trp Thr Ser Pro
 1               5                  10                  15

Phe Val Ile Arg Val Arg Ile Val Leu Asn Leu Lys Gly Leu Ala Tyr
            20                  25                  30

Glu Tyr Val Glu Glu Asp Leu Gly Asn Lys Ser Ala Leu Leu Leu Gly
        35                  40                  45

Ser Asn Pro Val His Lys Ser Val Pro Val Leu Leu His Ala Gly Arg
    50                  55                  60

Ala Ile Asn Glu Ser Gln Val Ile Leu Gln Tyr Ile Asp Glu Val Trp
65                  70                  75                  80

Ala Gly Thr Gly Pro Ala Val Leu Pro Ala Asp Pro Tyr Glu Arg Ala
                85                  90                  95

Val Ala Arg Phe Trp Gly Ala Tyr Ile Asp Asp Lys Val Glu Ser Ala
            100                 105                 110

Trp Leu Gly Met Leu Phe Arg Cys Ala Asn Glu Glu Glu Arg Ala Ala
        115                 120                 125

Ala Val Ala Arg Ala Arg Glu Ala Leu Asp Ala Leu Glu Gly Ala Phe
    130                 135                 140

Arg Asp Cys Ser Arg Gly Arg Pro Phe Phe Gly Gly Asp Asp Ile Gly
145                 150                 155                 160

Phe Val Asp Ala Val Leu Gly Gly Tyr Leu Gly Trp Phe Gly Ala Val
                165                 170                 175

Gly Arg Ile Ile Gly Ser Arg Leu Ile Asp Pro Ala Arg Thr Pro Leu
            180                 185                 190

Leu Ala Ala Trp Glu Asp Arg Phe Arg Ala Ala Asp Val Ala Lys Gly
        195                 200                 205

Val Val Pro Asp Asp Leu Asp Lys Met Leu Ala Phe Leu Gln Thr Leu
    210                 215                 220

Arg Ala Met Asn Tyr Ala Lys
225                 230
```

<210> SEQ ID NO 55
<211> LENGTH: 934
<212> TYPE: DNA
<213> ORGANISM: maize

-continued

```
<400> SEQUENCE: 55
acgacggaaa cagtagtgct gccagtagag agctctcaga actcgggaaa aaaatgtcag      60
aggccgccgt gcgtgtgatc ggcctatggc cgagcccgtt cgtgatccgc gtcctgatcg     120
ccctgaagct gaagggcgtc gagttcgagt tcgtggagga ggtggtgggc aggaagagcg     180
agctgctgct gaggtcgaac ccggtgcaca agaagatccc cgtcctgctc caccacggca     240
agcccatctc cgagtctctg atcgtcgtcc agtacatcga cgaggtctgg tcctccggcg     300
cgccggcctt cctccccgtc gacgctcacg cccgcgccgt ccagcggttc tgggcgcagt     360
acgtcgacga caagctgcct tgggcgatcc gcatactgaa gggaacggac gacggggggca    420 tggagcaggc ggcggggcag ctgtccgcgg ccctgcagct cctagaggag ctttcgcgc      480 agctcagcca ggggaagcgc tacttcggcg gggacagcgt cgggtacctg gacatcgctc     540
tggtgtcgca tgtcggctgg gtgaaggcgt ggagaagat cgccggggtc accctgctgg      600
acaaggccaa ggtcccgaac ctggtggcgt gggctgatcg tctgtgtgcc cacccggccg     660
tggtcgacgc catccctgac gcggacaagt tcgttgagtt cagcgtcacc tatggctcct     720
tttcgaagcc tatcaatgct cccgccaagt gagcaaaaag ggtccgtgca tgctttcgtc     780
attttcactt tcactgcgcg tgtgccggtg cgtgtcaaaa ttgcatagca agggattct      840 tctcccacat agatcttctt gtgatcatag tcaccaaatc agctctgaaa atgaagattt     900
tctgcccttc caaggaaaaa aaaaaaaaaaa aaaa                                934

<210> SEQ ID NO 56
<211> LENGTH: 232
<212> TYPE: PRT
<213> ORGANISM: maize

<400> SEQUENCE: 56

Met Ser Glu Ala Ala Val Arg Val Ile Gly Leu Trp Pro Ser Pro Phe
  1               5                  10                  15

Val Ile Arg Val Leu Ile Ala Leu Lys Leu Lys Gly Val Glu Phe Glu
                 20                  25                  30

Phe Val Glu Glu Val Val Gly Arg Lys Ser Glu Leu Leu Leu Arg Ser
             35                  40                  45

Asn Pro Val His Lys Lys Ile Pro Val Leu Leu His His Gly Lys Pro
         50                  55                  60

Ile Ser Glu Ser Leu Ile Val Val Gln Tyr Ile Asp Glu Val Trp Ser
 65                  70                  75                  80

Ser Gly Ala Pro Ala Phe Leu Pro Val Asp Ala His Ala Arg Ala Val
                 85                  90                  95

Gln Arg Phe Trp Ala Gln Tyr Val Asp Asp Lys Leu Pro Trp Ala Ile
            100                 105                 110

Arg Ile Leu Lys Gly Thr Asp Asp Gly Gly Met Glu Gln Ala Ala Gly
        115                 120                 125

Gln Leu Ser Ala Ala Leu Gln Leu Leu Glu Glu Ala Phe Ala Gln Leu
    130                 135                 140

Ser Gln Gly Lys Arg Tyr Phe Gly Gly Asp Ser Val Gly Tyr Leu Asp
145                 150                 155                 160

Ile Ala Leu Val Ser His Val Gly Trp Val Lys Ala Val Glu Lys Ile
                165                 170                 175

Ala Gly Val Thr Leu Leu Asp Lys Ala Lys Val Pro Asn Leu Val Ala
            180                 185                 190

Trp Ala Asp Arg Leu Cys Ala His Pro Ala Val Val Asp Ala Ile Pro
```

```
                195                 200                 205
Asp Ala Asp Lys Phe Val Glu Phe Ser Val Thr Tyr Gly Ser Phe Ser
    210                 215                 220

Lys Pro Ile Asn Ala Pro Ala Lys
225                 230

<210> SEQ ID NO 57
<211> LENGTH: 960
<212> TYPE: DNA
<213> ORGANISM: maize

<400> SEQUENCE: 57
aaccgcagct gaagctgctg gccatgtggg cgagcccgtt tgccctacgg gcgaagctag      60
cgctcaactt caagggcctg gcctacgagt acgtagagga ggacctccgc agcaagagcg     120
acctcctgct gagctcgaac ccggtgcaca agaaggtgcc cgtcctcatc cacaacggcg     180
tgcccgtctg tgagtcgcgg gtcatcgtgg agtacctcga cgaagtctac agcgccacgg     240
gcccccgctt cctccctgcc gacccatacg agcgtgccat ggcgcgcttc tgggcctcat     300
tcatcgacga aaagttcttg gcgtcgtggc taaaggcagg aaggggcaag acggacgagg     360
agaaggccga agggttgaag ctgacactcg cggccgtaga aaccttggaa ggggcgttca     420
tggagtgctc caaggggaag cccttctttg gaggcgatag tgtcggctac ctggacatcg     480
cgctcggggc cctggtagcg tggatgcgcg ccaccgaggc gcgtcatggt ctcaggctct     540
tcgacgcctc cagagtccgc tgctggagaa gtgggtggag cgcttcagcg agctggacga     600
ggtcgtggcg gtcatgccgg acatcgaccg gctagtagag ctcggcaagg tgagggaggc     660
tgctgcggct gcagcagctg ccgtaaacag ctgaacggaa cgcatctcgc ggtattgagg     720
cggtcaataa gtcggagaaa gatcttgata cctgtgtgta acaagcgaat ggtgtaataa     780
agaatacaat tagggtgtcg tttagttcac atgtcggtaa cgtaatggat aaccgataac     840
attaaatcat gtttgttata agtccaatcg taatcgatct catactacaa aaaaaaaaa     900 aaaaaaaaaa aaaaaaaaaa aaaaaaaaaa aaaaaaaaaa aaaaaaaaaa aaaaaaaaaa     960

<210> SEQ ID NO 58
<211> LENGTH: 203
<212> TYPE: PRT
<213> ORGANISM: maize

<400> SEQUENCE: 58

Met Trp Ala Ser Pro Phe Ala Leu Arg Ala Lys Leu Ala Leu Asn Phe
  1               5                  10                  15

Lys Gly Leu Ala Tyr Glu Tyr Val Glu Glu Asp Leu Arg Ser Lys Ser
                 20                  25                  30

Asp Leu Leu Leu Ser Ser Asn Pro Val His Lys Lys Val Pro Val Leu
             35                  40                  45

Ile His Asn Gly Val Pro Val Cys Glu Ser Arg Val Ile Val Glu Tyr
         50                  55                  60

Leu Asp Glu Val Tyr Ser Ala Thr Gly Pro Arg Phe Leu Pro Ala Asp
 65                  70                  75                  80

Pro Tyr Glu Arg Ala Met Ala Arg Phe Trp Ala Ser Phe Ile Asp Glu
                 85                  90                  95

Lys Phe Leu Ala Ser Trp Leu Lys Ala Gly Arg Gly Lys Thr Asp Glu
                100                 105                 110

Glu Lys Ala Glu Gly Leu Lys Leu Thr Leu Ala Ala Val Glu Thr Leu
            115                 120                 125
```

Glu Gly Ala Phe Met Glu Cys Ser Lys Gly Lys Pro Phe Phe Gly Gly
            130                 135                 140

Asp Ser Val Gly Tyr Leu Asp Ile Ala Leu Gly Ala Leu Val Ala Trp
145                 150                 155                 160

Met Arg Ala Thr Glu Ala Arg His Gly Leu Arg Leu Phe Asp Ala Ser
                165                 170                 175

Arg Val Arg Cys Trp Arg Ser Gly Trp Ser Ala Ser Ala Ser Trp Thr
            180                 185                 190

Arg Ser Trp Arg Ser Cys Arg Thr Ser Thr Gly
            195                 200

<210> SEQ ID NO 59
<211> LENGTH: 967
<212> TYPE: DNA
<213> ORGANISM: maize

<400> SEQUENCE: 59
gggctagcta gtcttgcaga ctcggagata cgactagctt gttataacaa gccaagcaga      60
gcggtgggga aaacaatggc gggcaatgag ggtcttaagg tccttggcct gcaggtgagc     120
ccgttcgtgc tccgcgtgtg catggcgttg aacacaaaag gagtgagcta cgagtacgtt     180
gaggaggacc tatccaacaa gagtgagctc ctgcttaagt ccaacccggt gcacaagaag     240
gtacccgtgc tcatccacaa cggtaagccc atctgtgagt cactcgtcat catgcagtac     300
gtcgacgagc tgttcgccgg ccggtcgatc ctaccaaccg accctacga gcgcgccact     360
gctcgcttct gggctgccta cgccgacgac aagttgttgc agcgtggta cggcatggtg     420
aaggcccagt cggcggagga gagagcggag aaggtggagg agacgctttc gcgatccag     480
cacatggaag tggccttcgc caagtgctcc ggcggcaacg ccgccttctt cggcggcgac     540
tccattggct acgtcgacat cgtgctcggc tccttcttgt tctggttcga ggcggtgcgc     600
agggtttacg acttggagat cattaacgct agcaatactc cgctcttggc tgcgtgggcg     660
gagcggtttg tagggactgt agaagcaaag gaggtggtgc cggtgcccga cgtggacatg     720
gccgtacagt gcatcaataa gcttcatgcc cctgccgccg ccataagttc acaatgagtc     780
gtgtaagtgt aataaccagg aaaaggtaaa tggtgcggtg ctatggtcca aattccaacc     840
gaataatgtt caaagcttac attgataggc ttgggttgtt gtcatcaaat aatgtggttc     900
agtcgtctcc tctgcaataa atataaatat gattgtttta gtgtgtaaaa aaaaaaaaa     960
aaaaaaa                                                               967

<210> SEQ ID NO 60
<211> LENGTH: 233
<212> TYPE: PRT
<213> ORGANISM: maize

<400> SEQUENCE: 60

Met Ala Gly Asn Glu Gly Leu Lys Val Leu Gly Leu Gln Val Ser Pro
1               5                   10                  15

Phe Val Leu Arg Val Cys Met Ala Leu Asn Thr Lys Gly Val Ser Tyr
            20                  25                  30

Glu Tyr Val Glu Glu Asp Leu Ser Asn Lys Ser Glu Leu Leu Leu Lys
        35                  40                  45

Ser Asn Pro Val His Lys Lys Val Pro Val Leu Ile His Asn Gly Lys
    50                  55                  60

Pro Ile Cys Glu Ser Leu Val Ile Met Gln Tyr Val Asp Glu Leu Phe

```
            65                  70                  75                  80
Ala Gly Arg Ser Ile Leu Pro Thr Asp Pro Tyr Glu Arg Ala Thr Ala
                        85                  90                  95
Arg Phe Trp Ala Ala Tyr Ala Asp Asp Lys Leu Leu Pro Ala Trp Tyr
                100                 105                 110
Gly Met Val Lys Ala Gln Ser Ala Glu Glu Arg Ala Glu Lys Val Glu
            115                 120                 125
Glu Thr Leu Ser Ala Ile Gln His Met Glu Val Ala Phe Ala Lys Cys
        130                 135                 140
Ser Gly Gly Asn Ala Ala Phe Phe Gly Gly Asp Ser Ile Gly Tyr Val
145                 150                 155                 160
Asp Ile Val Leu Gly Ser Phe Leu Phe Trp Phe Glu Ala Val Arg Arg
                165                 170                 175
Val Tyr Asp Leu Glu Ile Ile Asn Ala Ser Asn Thr Pro Leu Leu Ala
                180                 185                 190
Ala Trp Ala Glu Arg Phe Val Gly Thr Val Glu Ala Lys Glu Val Val
            195                 200                 205
Pro Val Pro Asp Val Asp Met Ala Val Gln Cys Ile Asn Lys Leu His
        210                 215                 220
Ala Pro Ala Ala Ala Ile Ser Ser Gln
225                 230

<210> SEQ ID NO 61
<211> LENGTH: 900
<212> TYPE: DNA
<213> ORGANISM: maize

<400> SEQUENCE: 61
ggccaagaac tcgatccgag caaaaaaatg tcggaggccg ccgtgcgagt gatcggccta      60
tggccgagcc cgttcgtgat ccgcgtcctg atcgcgctga agctgaagca tgtggagtac     120
gagttcgtgg aggaggtggt gggcagcaag agcgagctgc tgctcgcgtc gaacccggtg     180
cacaagaaga tccccgtcct gctccaccac ggcaagcccc tctccgagtc cctaatcatc     240
gttcagtaca tcgacgaggt ctggtcctcc ggcgcgccgg cggccatcct cccgccgac     300
ccttacgcgc gcgctgtcca gcggttctgg gcgcagtacg tcgacgacaa gatgcacccg     360
gcgatccgcg tactgaaggg aacgtacgac ggggacaagg agcaggcggc ggggcagctg     420
tccgcggccc tgcagctcct ggaggaggct ttcgcgcagc tcggccaggg gaagcgctac     480
ttcggcgggg acagcgtcgg gtacctggac atcgccctgg tgtcgcacgt cggctgggtg     540
aaggcggtgg agaagatcgc gggggtcact ctgctggacg aggcgaaggt tcccaacctg     600
gtggcgtggg ctgaccggct gtgcgcccac ccggccgtgg tggacgcgat ccctgacgcc     660
gacaagttcg ttgagttcag cgtgacctat gggtcgttct cttaatccta tcaatgctcc     720
caaagtgagc aaaatggctc cgcattgcgc tttgtgattt tcactgcgca tgtgccggtg     780
catgtcaccg tcaatagcat gtagtttgta tacatgtcct tctgtgaaaa taaagctttg     840
ctgcccgtca agggaaatc gacataaaaa aaaaaaaaa aaaaaaaaa aaaaaaaaa     900

<210> SEQ ID NO 62
<211> LENGTH: 225
<212> TYPE: PRT
<213> ORGANISM: maize

<400> SEQUENCE: 62

Met Ser Glu Ala Ala Val Arg Val Ile Gly Leu Trp Pro Ser Pro Phe
```

```
               1               5                  10                15
          Val Ile Arg Val Leu Ile Ala Leu Lys Leu Lys His Val Glu Tyr Glu
                           20                  25                  30

Phe Val Glu Glu Val Val Gly Ser Lys Ser Glu Leu Leu Leu Ala Ser
                       35                  40                  45

Asn Pro Val His Lys Lys Ile Pro Val Leu Leu His His Gly Lys Pro
                   50                  55                  60

Leu Ser Glu Ser Leu Ile Ile Val Gln Tyr Ile Asp Glu Val Trp Ser
          65                  70                  75                  80

Ser Gly Ala Pro Ala Ala Ile Leu Pro Ala Asp Pro Tyr Ala Arg Ala
                           85                  90                  95

Val Gln Arg Phe Trp Ala Gln Tyr Val Asp Asp Lys Met His Pro Ala
                       100                 105                 110

Ile Arg Val Leu Lys Gly Thr Tyr Asp Gly Asp Lys Glu Gln Ala Ala
                       115                 120                 125

Gly Gln Leu Ser Ala Ala Leu Gln Leu Leu Glu Glu Ala Phe Ala Gln
                   130                 135                 140

Leu Gly Gln Gly Lys Arg Tyr Phe Gly Gly Asp Ser Val Gly Tyr Leu
          145                 150                 155                 160

Asp Ile Ala Leu Val Ser His Val Gly Trp Val Lys Ala Val Glu Lys
                           165                 170                 175

Ile Ala Gly Val Thr Leu Leu Asp Glu Ala Lys Val Pro Asn Leu Val
                       180                 185                 190

Ala Trp Ala Asp Arg Leu Cys Ala His Pro Ala Val Asp Ala Ile
                       195                 200                 205

Pro Asp Ala Asp Lys Phe Val Glu Phe Ser Val Thr Tyr Gly Ser Phe
                   210                 215                 220

Ser
          225

<210> SEQ ID NO 63
<211> LENGTH: 872
<212> TYPE: DNA
<213> ORGANISM: maize

<400> SEQUENCE: 63
ggaaacaaag aaataaagag agacgatggg cggagaagaa ggcggcgacg ggctgaagct      60
gatcgggcag tacgggagcg cgttcgtgac gagggtgaag cttgctctca gcctcaaggg    120
gctgagctac gagtacgtcg aggaggatct cagaaacaag agcgcgctcc tcctcagctc    180
caacccggtg cacaaggcgg ttccagtgct gatccacaga ggcaagccta tctgcgagtc    240
gcaggtcatc gtgcagtaca tcgacgaggc ctttgccggc atcggcccgc ccctcctccc    300
ggccgacccc tacgaacgct cggtggcccg tttctgggct gccttcattg aagacaagct    360
tgtgtccccg tgggaccgag tgttccgggc gaagacggag gacgagaggg aagaggcgat    420
gaagcagatg cttgcggcag tggacgctct ggagggagca ctgaaggagg ggagacccag    480 accccttcttc ggcggcgaca cgtcgggta cgtggacgtc gttctgggcg gtgccgtctc    540
gtacgccaag gggcacgacg cgctcttcgg ttccgagctc atcgacgccg ccaagacgcc    600
gctcctggcc gcgtggatgg agcgcttctg cgagctcgac gcggccaagg cggtcctgca    660
ggacgtcgat agagtggtcc agtacggcaa gatgctgatc gccaagaatg ctgctgccac    720
tcgtcaggcg tagtgttttt ctgatcgatc agcttgtatg tatatgaatt gaacttgtaa    780
aaccaaatcg ttcaagtttg atggtaagtt ccatgttaga aaaaaaaaaa aaaaaaaaa    840
```
aaaaaaaaaa aaaaaaaaaa aaaaaaaaaa aa                                  872

<210> SEQ ID NO 64
<211> LENGTH: 235
<212> TYPE: PRT
<213> ORGANISM: maize

<400> SEQUENCE: 64

Met Gly Gly Glu Glu Gly Gly Asp Gly Leu Lys Leu Ile Gly Gln Tyr
  1               5                  10                  15

Gly Ser Ala Phe Val Thr Arg Val Lys Leu Ala Leu Ser Leu Lys Gly
                 20                  25                  30

Leu Ser Tyr Glu Tyr Val Glu Glu Asp Leu Arg Asn Lys Ser Ala Leu
             35                  40                  45

Leu Leu Ser Ser Asn Pro Val His Lys Ala Val Pro Val Leu Ile His
         50                  55                  60

Arg Gly Lys Pro Ile Cys Glu Ser Gln Val Ile Val Gln Tyr Ile Asp
 65                  70                  75                  80

Glu Ala Phe Ala Gly Ile Gly Pro Pro Leu Leu Pro Ala Asp Pro Tyr
                 85                  90                  95

Glu Arg Ser Val Ala Arg Phe Trp Ala Ala Phe Ile Glu Asp Lys Leu
            100                 105                 110

Val Ser Pro Trp Asp Arg Val Phe Arg Ala Lys Thr Glu Asp Glu Arg
        115                 120                 125

Glu Glu Ala Met Lys Gln Met Leu Ala Ala Val Asp Ala Leu Glu Gly
    130                 135                 140

Ala Leu Lys Glu Gly Arg Pro Arg Pro Phe Phe Gly Gly Asp Ser Val
145                 150                 155                 160

Gly Tyr Val Asp Val Val Leu Gly Gly Ala Val Ser Tyr Ala Lys Gly
                165                 170                 175

His Asp Ala Leu Phe Gly Ser Glu Leu Ile Asp Ala Ala Lys Thr Pro
            180                 185                 190

Leu Leu Ala Ala Trp Met Glu Arg Phe Cys Glu Leu Asp Ala Ala Lys
        195                 200                 205

Ala Val Leu Gln Asp Val Asp Arg Val Val Gln Tyr Gly Lys Met Leu
    210                 215                 220

Ile Ala Lys Asn Ala Ala Ala Thr Arg Gln Ala
225                 230                 235

<210> SEQ ID NO 65
<211> LENGTH: 971
<212> TYPE: DNA
<213> ORGANISM: maize

<400> SEQUENCE: 65
gtgactgtga tctatactat aaggtgaaca agatctcttt gtctactgta gttgcagcac      60
cagcagcagc agcagaagag cagcgcctga gctccagcaa taatggccga agggcgtg       120 aaggtgttgg ggatgtgggc gagccccatg gtgatcaggg tggagtgggc gctgcggctg     180
aagggcgtcg agtacgagta cgtcgacgag gacctcgcca acaagagcgc cgacctgctc     240
cgccacaacc cggtgaccaa gaaggtgccc gtgctcgtcc acgacggcaa gccggtcgcg     300
gagtccacca tcatcgtgga gtacatcgac gaggtctgga agggcggcta cccccatcatg    360 ccgggcgacc cctacgagcg cgcccaggcg aggttctggg ccaggttcgc ggaagacaag     420
tgcaacgctg ctctgtaccc gatcttcacc gcgaccggcg aggcgcagcg caaggcggtg     480

-continued

```
cacgaggccc agcagtgcct caagaccctg agacggcct tggaggggaa gaagttcttc      540
ggcggcgacg ccgtgggcta cctcgacatc gtcgtcgggt ggttcgcgca ctggctcccc      600
gtcatcgagg aggtgaccgg cgccagcgtc gtcacccacg aggagctgcc gctgatgaag      660
gcctggttcg gtcggttcct cgcccttgac gtggtgaagg cggccctgcc cgacagggac      720
aggctcctcg ccgccaacaa ggcccgccgt gagcagctcc tctccgcgta gatatggcta      780
gtaattctgg agcagctagt ttcaccgccg acgctcatat attgctgaat aaggactggt      840
tgcacttttg cacgttgtgc agtgcagccc gaggtttgga tgacctctgc ccctctgttc      900
catttcagaa tggtagtccc ataataatgc atatacatca tgcaaaaaaa aaaaaaaaa       960 aaaaaaaaaa a                                                          971
```

<210> SEQ ID NO 66
<211> LENGTH: 222
<212> TYPE: PRT
<213> ORGANISM: maize

<400> SEQUENCE: 66

```
Met Ala Glu Lys Gly Val Lys Val Leu Gly Met Trp Ala Ser Pro Met
  1               5                  10                  15

Val Ile Arg Val Glu Trp Ala Leu Arg Leu Lys Gly Val Glu Tyr Glu
             20                  25                  30

Tyr Val Asp Glu Asp Leu Ala Asn Lys Ser Ala Asp Leu Leu Arg His
         35                  40                  45

Asn Pro Val Thr Lys Lys Val Pro Val Leu Val His Asp Gly Lys Pro
     50                  55                  60

Val Ala Glu Ser Thr Ile Ile Val Glu Tyr Ile Asp Glu Val Trp Lys
 65                  70                  75                  80

Gly Gly Tyr Pro Ile Met Pro Gly Asp Pro Tyr Glu Arg Ala Gln Ala
                 85                  90                  95

Arg Phe Trp Ala Arg Phe Ala Glu Asp Lys Cys Asn Ala Ala Leu Tyr
            100                 105                 110

Pro Ile Phe Thr Ala Thr Gly Glu Ala Gln Arg Lys Ala Val His Glu
        115                 120                 125

Ala Gln Gln Cys Leu Lys Thr Leu Glu Thr Ala Leu Glu Gly Lys Lys
    130                 135                 140

Phe Phe Gly Gly Asp Ala Val Gly Tyr Leu Asp Ile Val Val Gly Trp
145                 150                 155                 160

Phe Ala His Trp Leu Pro Val Ile Glu Glu Val Thr Gly Ala Ser Val
                165                 170                 175

Val Thr His Glu Glu Leu Pro Leu Met Lys Ala Trp Phe Gly Arg Phe
            180                 185                 190

Leu Ala Leu Asp Val Val Lys Ala Ala Leu Pro Asp Arg Asp Arg Leu
        195                 200                 205

Leu Ala Ala Asn Lys Ala Arg Arg Glu Gln Leu Leu Ser Ala
    210                 215                 220
```

<210> SEQ ID NO 67
<211> LENGTH: 1074
<212> TYPE: DNA
<213> ORGANISM: maize

<400> SEQUENCE: 67

```
gctctaacac agcgcaagcc atggcaggac gagtagcgga caaagaccca gagctgaagg      60
```

-continued

```
tgctcggagt gtggtcgagc ccgttcgtta tcagggcccg cgtcgcgcta aacctcaagg    120
gcctggccta ccgatacgtg gaggacaacc tggacagcaa gagcgagctc ctcctcgcct    180
ccaacccccgt gcacgggaag gtgccggtgc tcctccacga cggcaggccc gtctgcgagt   240
cccgggtcat cgtggagtat atcgacgagg ccttcccggc cagcggcccc tgcctcctcc    300
ccgccgaccc gtaccgccgc gccgtcgacc gcttctgggc ctcctacgcc gacgacaagc    360
tctttcccac ctggataccc gtctacaacg gcaggacgag cgaggacagg gtcgcggcgg    420
cgaggcaggt cgtggccgtg ctggagaagt ttgagcaggc gttcgatgag tgctccgggt    480
ccggggggcaa ggcgttcttc ggcggggacg ctgctggcct cgtggacgtc gtgctaggcg    540
gcttcctcgg gtggctgcgc gcgtctgagg cgatgtgtgg cgtgagggtc atcgaccccg    600
ccaagacgcc gctgctggcg gcgtgggcgg accggttcgc cgcgctcgac ggcgtcaggg    660
aggtgatacc tgacgtgcag aggctgctgg agtataacaa gattaggcga gctcgtcgtg    720
ggctgccgta ggtgctgggc cttgggccat ctatctgtca ccatgtggtc agtcaactct    780
aagcaggaga ctttgacaag gttgaaagtt agttcatgaa ggtgggcaat ctaattagga    840
tgctcatgct ttagctagga gtgccattag ttttcctgtt gaaaggcatg tttggttcct    900
ctttcctact gaaagagttt gtaatataat ctatgatgct ttgagtttga gaaagaact    960
atgaataaaa catggatatc ttccgatatt tcagttcaaa ttaaaaaaaa aaaaaaaaaa   1020
aaaaaaaaaa aaaaaaaaaa aaaaaaaaaa aaaaaaaaaa aaaaaaaaaa aaaa         1074
```

<210> SEQ ID NO 68
<211> LENGTH: 236
<212> TYPE: PRT
<213> ORGANISM: maize

<400> SEQUENCE: 68

```
Met Ala Gly Arg Val Ala Asp Lys Asp Pro Glu Leu Lys Val Leu Gly
  1               5                  10                  15

Val Trp Ser Ser Pro Phe Val Ile Arg Ala Arg Val Ala Leu Asn Leu
                 20                  25                  30

Lys Gly Leu Ala Tyr Arg Tyr Val Glu Asp Asn Leu Asp Ser Lys Ser
             35                  40                  45

Glu Leu Leu Leu Ala Ser Asn Pro Val His Gly Lys Val Pro Val Leu
         50                  55                  60

Leu His Asp Gly Arg Pro Val Cys Glu Ser Arg Val Ile Val Glu Tyr
     65                  70                  75                  80

Ile Asp Glu Ala Phe Pro Ala Ser Gly Pro Cys Leu Leu Pro Ala Asp
                 85                  90                  95

Pro Tyr Arg Arg Ala Val Asp Arg Phe Trp Ala Ser Tyr Ala Asp Asp
            100                 105                 110

Lys Leu Phe Pro Thr Trp Ile Pro Val Tyr Asn Gly Arg Thr Ser Glu
        115                 120                 125

Asp Arg Val Ala Ala Ala Arg Gln Val Val Ala Val Leu Glu Lys Phe
    130                 135                 140

Glu Gln Ala Phe Asp Glu Cys Ser Gly Ser Gly Lys Ala Phe Phe
145                 150                 155                 160

Gly Gly Asp Ala Ala Gly Leu Val Asp Val Val Leu Gly Gly Phe Leu
                165                 170                 175

Gly Trp Leu Arg Ala Ser Glu Ala Met Cys Gly Val Arg Val Ile Asp
            180                 185                 190

Pro Ala Lys Thr Pro Leu Leu Ala Ala Trp Ala Asp Arg Phe Ala Ala
```

```
            195                 200                 205
Leu Asp Gly Val Arg Glu Val Ile Pro Asp Val Gln Arg Leu Leu Glu
    210                 215                 220

Tyr Asn Lys Ile Arg Arg Ala Arg Arg Gly Leu Pro
225                 230                 235
```

<210> SEQ ID NO 69
<211> LENGTH: 904
<212> TYPE: DNA
<213> ORGANISM: maize

<400> SEQUENCE: 69

```
gacaccacag gcataacaga acagaaccat cgatcgagct tggttgctcg gcagcagcta    60
gcaatggccg ccaatggagg tgatgagctg aagctgctgg gcgtgtggga cagcccgtac   120
gtcaacaggg tccagatcgt gctcaacctc aagggcctca gctacgagta cgtggaggag   180
gacctcctca gcaagagcga gctcctcctc aattccaacc cggtgcacaa gaaagtgccc   240
gtgctcatcc acgccggcaa gccggtcgcc gagtcgcagg ccatcgttca gtacctcgac   300
gaggctttcc ccagcggcac gttcccgtcg gtcctcccag ccgaacccta cgcacgcgcc   360
accgcccgct tctgggccgc cttcgtcgac gacaaggtcg gtctccatg gcacacggtc     420
ctgttcgcgc gggagcacgg gaagaaggcg gacgcggcgt cgcggatcgt cgcggcgctg   480
gagacgctgg agggtgcgtt cgaggactgc tccggcggga gggactactt cggcggcgac   540
gccatcggct tcgtggacgt ggtcctcggc agctacctgg gctggttcaa ggtgttcgag   600
aagatggtcg gcgtcagggt cctggacgtg gcgaggacgc cgctcctcgc gcgcgtgggg   660
gagcgtttcg cggcggcgga agcggccaag gacgtcctgc cggatgacgt tgacaaggtg   720
ctcgagttcc ttcagaagtt cctggattag atgcgcgcca ccatgtgctc cggtgtccaa   780
ctcccaatgt ttgtttgctt tggtcatttt cggtgcgctg ttaatgggcc tcggatgttt   840
gccagttgat taacttgatt ttatagaatc ttaataatat tctaaaacaa aaaaaaaaa    900
aaaa                                                                904
```

<210> SEQ ID NO 70
<211> LENGTH: 228
<212> TYPE: PRT
<213> ORGANISM: maize

<400> SEQUENCE: 70

```
Met Ala Ala Asn Gly Gly Asp Glu Leu Lys Leu Leu Gly Val Trp Asp
  1               5                  10                  15

Ser Pro Tyr Val Asn Arg Val Gln Ile Val Leu Asn Leu Lys Gly Leu
                 20                  25                  30

Ser Tyr Glu Tyr Val Glu Glu Asp Leu Leu Ser Lys Ser Glu Leu Leu
            35                  40                  45

Leu Asn Ser Asn Pro Val His Lys Lys Val Pro Val Leu Ile His Ala
     50                  55                  60

Gly Lys Pro Val Ala Glu Ser Gln Ala Ile Val Gln Tyr Leu Asp Glu
 65                  70                  75                  80

Ala Phe Pro Ser Gly Thr Phe Pro Ser Val Leu Pro Ala Glu Pro Tyr
                 85                  90                  95

Ala Arg Ala Thr Ala Arg Phe Trp Ala Ala Phe Val Asp Asp Lys Val
            100                 105                 110

Gly Ser Pro Trp His Thr Val Leu Phe Ala Arg Glu His Gly Lys Lys
        115                 120                 125
```

```
Ala Asp Ala Ala Ser Arg Ile Val Ala Ala Leu Glu Thr Leu Glu Gly
        130                 135                 140

Ala Phe Glu Asp Cys Ser Gly Gly Arg Asp Tyr Phe Gly Gly Asp Ala
145                 150                 155                 160

Ile Gly Phe Val Asp Val Leu Gly Ser Tyr Leu Gly Trp Phe Lys
                165                 170                 175

Val Phe Glu Lys Met Val Gly Val Arg Val Leu Asp Val Ala Arg Thr
                180                 185                 190

Pro Leu Leu Ala Ala Trp Gly Glu Arg Phe Ala Ala Glu Ala Ala
        195                 200                 205

Lys Asp Val Leu Pro Asp Asp Val Asp Lys Val Leu Glu Phe Leu Gln
        210                 215                 220

Lys Phe Leu Asp
225

<210> SEQ ID NO 71
<211> LENGTH: 1013
<212> TYPE: DNA
<213> ORGANISM: maize

<400> SEQUENCE: 71
ctggtctctt gcacagactc ggagcaagat aggcctagct ggttacaagc caagaacaag      60
tagagcggta gagggaaaat atatctggag agggaaacaa tggcgggcga ggagggtctt     120
aaggtcctcg gcctgcaggt gagcccgttc gtgctccgcg tgtgcttggc gctgaacatg     180
aaaggagtga gttacgagta cgtcgaggag gacatatcca acaagagtga gctcctgctc     240
aagtccaacc cggtgcacaa gaaggtgccc gtgctcatcc acaacggtaa gcccatctgc     300
gagtcactcg tcatcatgca gtacgtcgac gagctgttcg ccggccggcc gatcctccca     360
accgacccct acgagcgcgc cactgctcgc ttctgggctg cctacgccga cgacaagttg     420
tttccagcgt ggtacggcat ggtgaaggcc cagccggagg aggagagggc ggagaaggcg     480
aaggagacgc tcgccgccat cgagcacatg gaagtgacct cgccaagtg ctccggcggc     540 aacgccttct tcggtggcga ctccatcggc tacgtcgaca tcgtgctgac gtgctcggct     600
ccttcttgtt ctggttcgag gcggtgcgca gggttttcga cctggagatc attaacgcta     660
gcaagactcc gctgttggct gcgtgggcgg agcggtttgt agggactgta gaagcgaagg     720
aggtggtgcc gttgcccacg gcggacatgg cggtacagta catcaataag cttcatgccc     780
ccctgccgcc gccatgagtt cacaatgagt cgtgtaagtg taaccaagca gggaaaaagg     840
taaatggtgc ggtgctttgg tccaaattcc aaccgaataa tgttcaaagc ttatattgat     900
aggcttgggt tgttgtcatc aaatattgtg gttcagtcgt ctcctctgca ataaatataa     960
atatgattat tactttcttt gccgtaaaaa aaaaaaaaa aaaaaaaaaa aaa             1013

<210> SEQ ID NO 72
<211> LENGTH: 200
<212> TYPE: PRT
<213> ORGANISM: maize

<400> SEQUENCE: 72

Met Ala Gly Glu Glu Gly Leu Lys Val Leu Gly Leu Gln Val Ser Pro
1               5                   10                  15

Phe Val Leu Arg Val Cys Leu Ala Leu Asn Met Lys Gly Val Ser Tyr
            20                  25                  30

Glu Tyr Val Glu Glu Asp Ile Ser Asn Lys Ser Glu Leu Leu Leu Lys
```

|         |         |         |         | 35      |         |         |         | 40      |         |         |         | 45      |         |         |
|---------|---------|---------|---------|---------|---------|---------|---------|---------|---------|---------|---------|---------|---------|---------|

Ser Asn Pro Val His Lys Lys Val Pro Val Leu Ile His Asn Gly Lys
 50                      55                      60

Pro Ile Cys Glu Ser Leu Val Ile Met Gln Tyr Val Asp Glu Leu Phe
 65                  70                      75                      80

Ala Gly Arg Pro Ile Leu Pro Thr Asp Pro Tyr Glu Arg Ala Thr Ala
                 85                      90                      95

Arg Xaa Trp Ala Ala Tyr Ala Asp Asp Lys Leu Phe Pro Ala Trp Tyr
             100                     105                     110

Gly Met Val Lys Ala Gln Pro Glu Glu Arg Ala Glu Lys Ala Lys
             115                     120                     125

Glu Thr Leu Ala Ala Ile Glu His Met Glu Val Thr Phe Ala Lys Cys
 130                     135                     140

Ser Gly Gly Asn Ala Phe Phe Gly Gly Asp Ser Ile Gly Tyr Val Asp
 145                     150                     155                     160

Ile Val Leu Thr Cys Ser Ala Pro Ser Cys Ser Gly Ser Arg Arg Cys
                 165                     170                     175

Ala Gly Phe Ser Thr Trp Arg Ser Leu Thr Leu Ala Arg Leu Arg Cys
             180                     185                     190

Trp Leu Arg Gly Arg Ser Gly Leu
             195                     200

<210> SEQ ID NO 73
<211> LENGTH: 1068
<212> TYPE: DNA
<213> ORGANISM: maize

<400> SEQUENCE: 73
ggcagcacaa acgagcacaa taatggccgg aggaggtgac gatgaactca agctgctggg     60
ggcgtgggcg agcccattcg tcctgcgggt gaagctcgcg ctcagcttca agggcctgag    120
ctacgaggac gtggaggagg acctctccgg cggcaagagc gagctgctcc tcgagtccaa    180
cccggtgcac aagaaggtgc ccgtgctcct ccacaacggc aagcctgtgt gcagtcgca    240
gatcatcgtg cagtacatcg atgaggcctt cgccggcact ggcccgtccc ttctccctgc    300
cgacccgcac cagcgcgccg tggctcgctt ctggggtgcc tacattgacg acaagctcct    360
agccttctgg ctgcaatcag caagggccaa gacgcaggag gaaaaggccg aggcgctgaa    420
gcaggcgctc gccgcggccg agaacctgga ggccgccttc acggagatct ccgagggcaa    480
gcccttcttc ggcggcgaca gcgtcgggta cctggacgtg acgctgggag cgctggtcgc    540
gtgggtgcac gccgccgaga agctgtacgg gatgaggctc ttcgacgcca cgaggacccc    600
gcggctgagc gcgttcgtgg agaggttcgg cgcgctcgga gcggccaagg cggtgctgcc    660
cgacgtcgat ggcctcgtcg aatacgccaa acagaggcag gccgacgcgg cagctgcagc    720
ctcggacagc taaaaaaatg gcaccgcgag tttaccgacg tacggcagtc agtgctggac    780
gaagcaagat tatgggtatt ctgcatatac tattcagctg ctgtcgtgtg tattagctgg    840
ttgttactag attgttggcg tgtgacaaag aaaataaaaa tggatgggcc ggctttcgtt    900
tgtgtttgta ttgtacgttt gccgtttggt gtgtaccgtg tgtcgtaggt cggaaattgc    960
cgcatatcgg catgcctagt gtaaccctgt cgattatgca gtctggtttg ctttatattc   1020
accaaagtaa gtaatctgaa taattttctt gaaaaaaaaa aaaaaaaa                1068

<210> SEQ ID NO 74
<211> LENGTH: 236

```
-continued

<212> TYPE: PRT
<213> ORGANISM: maize

<400> SEQUENCE: 74

Met Ala Gly Gly Gly Asp Asp Glu Leu Lys Leu Leu Gly Ala Trp Ala
 1               5                  10                  15

Ser Pro Phe Val Leu Arg Val Lys Leu Ala Leu Ser Phe Lys Gly Leu
                20                  25                  30

Ser Tyr Glu Asp Val Glu Glu Asp Leu Ser Gly Gly Lys Ser Glu Leu
            35                  40                  45

Leu Leu Glu Ser Asn Pro Val His Lys Lys Val Pro Val Leu Leu His
        50                  55                  60

Asn Gly Lys Pro Val Cys Glu Ser Gln Ile Ile Val Gln Tyr Ile Asp
 65                 70                  75                  80

Glu Ala Phe Ala Gly Thr Gly Pro Ser Leu Leu Pro Ala Asp Pro His
                85                  90                  95

Gln Arg Ala Val Ala Arg Phe Trp Gly Ala Tyr Ile Asp Asp Lys Leu
               100                 105                 110

Leu Ala Phe Trp Leu Gln Ser Ala Arg Ala Lys Thr Gln Glu Glu Lys
           115                 120                 125

Ala Glu Ala Leu Lys Gln Ala Leu Ala Ala Ala Glu Asn Leu Glu Ala
       130                 135                 140

Ala Phe Thr Glu Ile Ser Glu Gly Lys Pro Phe Phe Gly Gly Asp Ser
145                 150                 155                 160

Val Gly Tyr Leu Asp Val Thr Leu Gly Ala Leu Val Ala Trp Val His
               165                 170                 175

Ala Ala Glu Lys Leu Tyr Gly Met Arg Leu Phe Asp Ala Thr Arg Thr
           180                 185                 190

Pro Arg Leu Ser Ala Phe Val Glu Arg Phe Gly Ala Leu Gly Ala Ala
       195                 200                 205

Lys Ala Val Leu Pro Asp Val Asp Gly Leu Val Glu Tyr Ala Lys Gln
   210                 215                 220

Arg Gln Ala Asp Ala Ala Ala Ala Ser Asp Ser
225                 230                 235
```